US008133840B2

(12) United States Patent
Mika et al.

(10) Patent No.: US 8,133,840 B2
(45) Date of Patent: Mar. 13, 2012

(54) STABLE COMPOSITE MATERIAL COMPRISING SUPPORTED POROUS GELS

(75) Inventors: Alicja M. Mika, Hamilton (CA); Maggie Sanju Wang, Hamilton (CA); Ronald F. Childs, Qualicum Beach (CA)

(73) Assignee: Natrix Separations Inc., Burlington, Ontario (CA)

( * ) Notice: Subject to any disclaimer, the term of this patent is extended or adjusted under 35 U.S.C. 154(b) by 984 days.

(21) Appl. No.: 11/628,805

(22) PCT Filed: Jun. 6, 2005

(86) PCT No.: PCT/CA2005/000880
§ 371 (c)(1),
(2), (4) Date: Mar. 11, 2008

(87) PCT Pub. No.: WO2005/120701
PCT Pub. Date: Dec. 22, 2005

(65) Prior Publication Data
US 2008/0264867 A1    Oct. 30, 2008

Related U.S. Application Data

(60) Provisional application No. 60/577,164, filed on Jun. 7, 2004.

(51) Int. Cl.
*B01J 20/26* (2006.01)
(52) U.S. Cl. .............. 502/402; 502/439; 502/526
(58) Field of Classification Search ................ 502/401, 502/402, 439, 526, 515, 516
See application file for complete search history.

(56) References Cited

U.S. PATENT DOCUMENTS

| | | |
|---|---|---|
| 3,209,915 A | 10/1965 | Gutkowski |
| 3,417,870 A | 12/1968 | Bray |
| 3,473,668 A | 10/1969 | Bunyard et al. |
| 3,623,610 A | 11/1971 | Olsen et al. |
| 3,695,444 A | 10/1972 | Iaconelli |
| 3,713,921 A | 1/1973 | Fleischer et al. |
| 3,875,085 A | 4/1975 | Bolto |
| 3,939,105 A | 2/1976 | Jones, Jr. et al. |
| 3,997,482 A | 12/1976 | Turková et al. |
| 4,108,804 A | 8/1978 | Seita et al. |
| 4,133,764 A | 1/1979 | Bardin et al. |
| 4,170,540 A | 10/1979 | Cook, Jr. et al. |
| 4,224,415 A | 9/1980 | Meitzner et al. |
| 4,230,697 A | 10/1980 | Nishida et al. |
| 4,275,056 A | 6/1981 | Takaku et al. |
| 4,397,892 A | 8/1983 | Lorant et al. |
| 4,473,474 A | 9/1984 | Ostreicher et al. |
| 4,525,374 A | 6/1985 | Vaillancourt |
| 4,525,527 A | 6/1985 | Takeda et al. ............ 524/831 |
| 4,601,828 A | 7/1986 | Gershoni |
| 4,678,844 A | 7/1987 | Sakuragi et al. |
| 4,889,632 A | 12/1989 | Svec et al. |
| 4,923,610 A | 5/1990 | Svec et al. |
| 4,944,879 A | 7/1990 | Steuck |
| 4,952,349 A | 8/1990 | Svec et al. ............ 264/45.1 |
| 4,999,171 A | 3/1991 | Kato et al. |
| 5,019,270 A | 5/1991 | Afeyan et al. |
| 5,059,659 A | 10/1991 | Gregor et al. |
| 5,114,585 A | 5/1992 | Kraus et al. |
| 5,130,343 A | 7/1992 | Fréchet et al. |
| 5,137,633 A | 8/1992 | Wang |
| 5,147,541 A | 9/1992 | McDermott, Jr. et al. |
| 5,160,627 A | 11/1992 | Cussler et al. |
| 5,176,832 A | 1/1993 | Dorta et al. |
| 5,228,989 A | 7/1993 | Afeyan et al. |
| 5,268,306 A | 12/1993 | Berger et al. |
| 5,269,931 A | 12/1993 | Hu et al. |
| 5,277,915 A | 1/1994 | Provonchee et al. |
| 5,282,971 A | 2/1994 | Degen et al. |
| 5,316,680 A | 5/1994 | Frechet et al. |
| 5,334,310 A | 8/1994 | Fréchet et al. |
| 5,384,042 A | 1/1995 | Afeyan et al. |
| 5,403,482 A | 4/1995 | Steere et al. |
| 5,422,284 A | 6/1995 | Lau |
| 5,460,720 A | 10/1995 | Schneider |

(Continued)

FOREIGN PATENT DOCUMENTS

CA    1200158    2/1986
(Continued)

OTHER PUBLICATIONS

Ji, Chun-Nuan, et al.; "Studies on synthesis and properties of snake-cage type chelating resin of carboxymethyl cellulose-ethylenediamine-B-62", XP002522863 retrieved from STN Database accession No. 2003:314324 (abstract) & Linchan Huaxue Yu Gongye, 23(1), 35-38 Coden: LHYGD7; Issn: 0253-2417, 2003.

Yonese M., et al ., "Visoelastic Properties of Poly (Vinyl Alcohol)/Alginate Snake-Cage Hyrdrogels and Interpenetrating Hydrogels", Polymer Journal, Society of Polymer Science, Tokyo, JP, vol. 24, No. 4, Apr. 15, 1992, pp. 395-404.

Supplementary EP Search Report for EP 05 75 3128 sent May 8, 2009.

Afeyan, N.B., et al., "Flow-through particles for the high-performance liquid chromatographic separation of biomolecules: perfusion chromatography", J. Chromatogr., (1990) p. 1-29, vol. 519.

Akhtar, S., et al., "Coatings reduce the fouling of microfiltration membranes", J. Memb. Sci., (1995) p. 209-218, vol. 107.

(Continued)

*Primary Examiner* — Edward Johnson
(74) *Attorney, Agent, or Firm* — Foley Hoag, LLP

(57) ABSTRACT

This invention relates to a stable composite material comprising a support member that has a plurality of pores extending through the support member, and a macroporous crosslinked gel that is located in, and fills, the pores of the support member, in which crosslinked gel is entrapped a stabilizing polymer, which stabilizing polymer is neutral, linear or branched, non-crosslinked, and substantially water-insoluble. The presence of the stabilizing polymer is such that it allows the composite material to largely retain its porosity and morphology after being dried. The invention also relates to a process for preparing the stable composite material described above, and to its use. The stable composite material is suitable, for example, for separation of substances, for example by filtration or adsorption, including chromatography, for use as a support in synthesis or for use as a support for cell growth.

18 Claims, 22 Drawing Sheets

U.S. PATENT DOCUMENTS

| | | | |
|---|---|---|---|
| 5,472,606 | A | 12/1995 | Steere et al. |
| 5,593,576 | A | 1/1997 | Girot et al. |
| 5,593,729 | A | 1/1997 | Fréchet et al. |
| 5,599,453 | A | 2/1997 | Girot et al. |
| 5,646,001 | A | 7/1997 | Terstappen et al. |
| 5,648,390 | A | 7/1997 | Banks et al. |
| 5,672,276 | A | 9/1997 | Girot et al. |
| 5,723,601 | A | 3/1998 | Larsson et al. |
| 5,728,457 | A | 3/1998 | Fréchet et al. |
| 5,756,717 | A | 5/1998 | Paliwal et al. |
| 5,780,688 | A | 7/1998 | Hoffmann et al. |
| 5,906,734 | A | 5/1999 | Girot et al. |
| 5,929,214 | A | 7/1999 | Peters et al. |
| 5,972,634 | A | 10/1999 | Tanzi et al. |
| 6,033,784 | A | 3/2000 | Jacobsen et al. |
| 6,045,697 | A | 4/2000 | Girot et al. |
| 6,086,769 | A | 7/2000 | Kilambi et al. |
| 6,143,174 | A | 11/2000 | Graus |
| 6,258,276 | B1 | 7/2001 | Mika et al. |
| 6,271,278 | B1 | 8/2001 | Park et al. ............... 521/150 |
| 6,277,489 | B1 | 8/2001 | Abbott et al. |
| 6,613,234 | B2 | 9/2003 | Voute et al. |
| 6,635,104 | B2 | 10/2003 | Komkova et al. ............ 96/4 |
| 6,635,420 | B1 | 10/2003 | Hosel et al. |
| 6,766,817 | B2 | 7/2004 | da Silva et al. |
| 6,780,582 | B1 | 8/2004 | Wagner et al. |
| 6,824,975 | B2 | 11/2004 | Hubscher et al. |
| 6,911,148 | B1 | 6/2005 | Demmer et al. |
| 6,918,404 | B2 | 7/2005 | Dias da Silva et al. |
| 6,951,880 | B2 | 10/2005 | Roberts et al. |
| 6,984,604 | B2 | 1/2006 | Cobb et al. |
| 7,066,586 | B2 | 6/2006 | da Silva et al. |
| 7,163,803 | B2 | 1/2007 | Hamon et al. |
| 7,285,255 | B2 | 10/2007 | Kadlec et al. |
| 7,316,919 | B2 | 1/2008 | Childs et al. |
| 7,507,420 | B2 | 3/2009 | Ng et al. |
| 7,598,371 | B2 | 10/2009 | Willson et al. |
| 7,824,548 | B2 | 11/2010 | DiLeo et al. |
| 2002/0005383 | A1 | 1/2002 | Voute et al. |
| 2002/0148769 | A1 | 10/2002 | Deuschle et al. |
| 2003/0155243 | A1 | 8/2003 | Sferrazza |
| 2003/0232895 | A1 | 12/2003 | Omidian et al. ............ 521/99 |
| 2004/0203149 | A1 | 10/2004 | Childs et al. |
| 2007/0212281 | A1 | 9/2007 | Kadlec et al. |

FOREIGN PATENT DOCUMENTS

| | | |
|---|---|---|
| CA | 2 173 754 | 4/1995 |
| CA | 2054933 | 8/2000 |
| CA | 2428280 | 5/2002 |
| DE | 199 43 921 | 1/2001 |
| EP | 0 105 629 | 4/1984 |
| EP | 0 304 161 | 2/1989 |
| EP | 0 506 247 | 9/1992 |
| EP | 0 316 642 | 3/1994 |
| EP | 0 320 023 | 9/1994 |
| EP | 0 664 732 | 12/1997 |
| JP | 62-014903 | 1/1987 |
| JP | 62-039636 | 2/1987 |
| JP | 01-070108 | 3/1989 |
| JP | 06-100725 A | 4/1994 |
| JP | 11 033370 | 2/1999 |
| WO | WO-87/06395 A1 | 10/1987 |
| WO | WO 90/04609 | 5/1990 |
| WO | WO 91/00762 | 1/1991 |
| WO | WO 91/14076 | 9/1991 |
| WO | WO-92/05595 A1 | 4/1992 |
| WO | WO 92/07899 | 5/1992 |
| WO | WO 93/07945 | 4/1993 |
| WO | WO 93/19115 | 9/1993 |
| WO | WO 94/08686 | 4/1994 |
| WO | WO 94/08713 | 4/1994 |
| WO | WO 94/09063 | 4/1994 |
| WO | WO-95/10346 | 4/1995 |
| WO | WO 97/17129 | 5/1997 |
| WO | WO 97/18904 | 5/1997 |
| WO | WO 98/01208 | 1/1998 |
| WO | WO 98/17377 | 4/1998 |
| WO | WO 99/20378 | 4/1999 |
| WO | WO 00/12618 | 3/2000 |
| WO | WO 00/50160 | 8/2000 |
| WO | WO 00/50161 | 8/2000 |
| WO | WO 00/54866 | 9/2000 |
| WO | WO 00/69549 | 11/2000 |
| WO | WO 01/08792 | 2/2001 |
| WO | WO-02/05934 | 1/2002 |
| WO | WO 02/28947 | 4/2002 |
| WO | WO 02/38257 | 5/2002 |
| WO | WO 03/008078 | 1/2003 |
| WO | WO 2004/073843 | 9/2004 |

OTHER PUBLICATIONS

Alpert, A. J., et al., "Preparation of a Porous Microparticulate Anion-Exchange Chromatography Support for Proteins", J. Chrom., (1979) p. 375-392, vol. 185.

Altomare, A., et al., "Methacrylic polymers containing permanent dipole azobenzene chromophores spaced from the main chain. $^{13}$C NMR spectra and photochromic properties", Macromol. Chem. Phys., (1999) p. 601-608, vol. 200.

Altomare, A, et al., "Synthesis and polymerization of amphiphilic methacrylates containing permanent dipole azobenzene chromophores", Journal of Polymer Science: Part A: Polymer Chemistry, (2001) p. 2957-2977, vol. 39.

Anderson, J.L., et al., "Model for Hydrodynamic Thickness of Thin Polymer Layers at Solid/Liquid Interfaces", Langmuir, (1991) p. 162-166, vol. 7.

Arshady, R., "In the name of particle formation", Colloids and Surfaces A: Physiochemical and Engineering Aspects, (1999) p. 325-333, vol. 153.

Barton, A.F.M., CRC Handbook of Solubility Parameters and Other Cohesion Parameters, 2nd ed., CRC Press, Boca Raton, FL (1991) Chapter 14.

Barbucci, R., et al., "Synthesis, chemical and rheological characterization of new hyaluronic acid-based hydrogels", J. Biomater. Sci.-Polym. Ed., (2000), p. 383-399, vol. 11.

Boschetti, E., "Advanced sorbents for preparative protein separation purposes", J. Chromatogr. A, (1994) p. 207-236, vol. 658.

Cabasso, I., et al., "Composite Hollow Fiber Membranes", J. Appl. Pol. Sci., (1979) p. 1509-1525, vol. 23.

Chanda, M., et al., "A New Method of Gel-Coating Polyethyleneimine (PEI) on Organic Resin Beads. High Capacity and Fast Kinetics of PEI Gel-Coated on Polystyrene" Ind. Eng. Chem. Res., (2001) p. 1624-1632, vol. 40.

Charcosset, C., "Purification of Proteins by Membrane Chromatography", Journal of Chemical Technology and Biotechnology, (1998) p. 95-110, vol. 71.

Childs, R.F., et al., "Formation of Pore-Filled Microfiltration Membranes Using a Combination of Modified Interfacial Polymerization and Grafting", J. Polym. Sci. Part A: Polym. Chem., (2002) p. 242-250, vol. 40.

Childs, R.F., et al., The design of high performance, gel-filled nanofiltration membranes, in a New Insights into Membrane Science and Technology: Polymeric, Inorganic and Biofunctional Membranes@ Elsevier, Edit. A. Butterfield and D Bhattacharyya, (2003) p. 353-375.

Claesson, P.M., et al., "Adsorption and interaction of a graft copolymer of poly(ethylene imine) and poly(ethylene oxide)", Coll. Surf., (1996) p. 131-139, vol. 112.

Claesson, P.M., et al., "Surface properties of poly(ethylene imine)-coated mica surfaces—salt and pH effects", Coll. Surf., (1997) p. 341-353, vol. 123-124.

Dickson, J.M., et al., "Development of a coating technique for the internal structure of polypropylene microfiltration membranes", J. Memb. Sci., (1998) p. 25-36, vol. 148.

Dudley, L.Y., et al., "Coatings for the Prevention of Fouling of Microfiltration Membranes", Chem. Eng. Res. Des., (1993) p. 327-328, vol. 71, Part A.

Eisenbach, C. D., "Isomerization of aromatic azo chromophores in poly(ethyl acrylate) networks and photomechanical effect", Polymer, (1980) 1175-1179, vol. 21.

Erim, F. B., et al., "Performance of a physically adsorbed high-molecular-mass polyethyleneimine layer as coating for the separation of basic proteins and peptides by capillary electrophoresis", J. Chromatography, (1995) p. 356-361, vol. 708.

Erim, F. B., "Separation of Phenols by Capillary Electrophoresis in a Polyethyleneimine-Coated Capillary" Microchemical. J., (1997) p. 283-287, vol. 57.

Ghosh, R., et al., "Analysis of protein transport and polarization through membranes using pulsed sample injection technique", Journal of Membrane Science, (2000) p. 75-84, vol. 175, No. 1.

Ghosh, R., "Bioseparation using supported liquid membrane chromatography", Journal of Membrane. Science, (2001) p. 243-247, vol. 192.

Ghosh, R., "Fractionation of biological macromolecules using carrier phase ultrafiltration", Biotechnology and Bioengineering, (2001) p. 1-11, vol. 74, No. 1.

Ghosh, R., et al., "Parameter scanning ultrafiltration: rapid optimisation of protein separation", Biotechnology and Bioengineering, (2003), p. 673-682, vol. 81.

Ghosh, R., "Protein separation using membrane chromatography: opportunities and challenges", Journal of Chromatography, (2002) p. 13-27, vol. 952.

Grulke, E.A., Polymer Handbook, 4th ed., (1999) Brandrup, J., et al., Wiley-Interscience, New York, Chapter VII, p. 675, 697 and 711.

Happel, J., et al., "Low Reynolds Number Hydrodynamics", Noordhof International Publishing, Leyden, (1973) p. 393.

Hatch, et al., "Preparation and use of snake-cage polyelectrolytes", Industrial and Engineering Chemistry, (1957) p. 1812-1819, vol. 49.

Hoffer, E., et al., "Hyperfiltration in Charged Membranes: The Fixed Charge Model", Desalination, (1967) p. 25-39, vol. 2.

Hvid, K.B., et al., "Preparation and Characterization of a New Ultrafiltration Membrane", J. Memb. Sci., (1990) p. 189-202, vol. 53.

Idol, W. K., et al., "Effects of Adsorbed Polyelectrolytes on Convective Flow and Diffusion in Porous Membranes", J. Memb. Sci., (1986) p. 269-286, vol. 28.

Inukai, M., et al., "Preparation and Characterization of Hyaluronic—Hydroxyethyl Acrylate Blend Hydrogel for Controlled Release Device", Chem. Pharm. Bull., (2000) p. 850-854, vol. 48.

Iritani, E., et al., "Concentration of proteinaceous solutions with superabsorbent hydrogels", Separation Science and Technology, (1993) p. 1819-1836, vol. 28, No. 10.

Jacobsen, C., et al., "Soft X-ray spectroscopy from image sequences with sub-100 nm spatial resolution", J. Microscopy, (2000) p. 173-184, vol. 197, Pt. 2.

Jensen, M., et al., "Loading into and electro-stimulated release of peptides and proteins from chondroitin 4-sulphate hydrogels", Eur. J. Pharm. Sci., (2002) p. 139-148, vol. 15.

Jiang, W., et al., "Pore-filled cation-exchange membranes containing poly(styrenesulfonic acid) gels", Desalination, (2003) p. 253-266, vol. 159.

Kagatani, S., et al., "Electroresponsive pulsatile depot delivery of insulin from poly(dimethylaminopropylacrylamide) gel in rats", J. Pharm. Sci., (1997) p. 1273-1277, vol. 86, No. 11.

Kapur, et al., "Hydrodynamic permeability of hydrogels stabilized within porous membranes", Ind. Eng. Chem. Res., (1996) p. 3179-3185, vol. 35.

Kapur, V., "Transport in Polymer/Gel-Modified Micropores", Ph.D. Thesis, (1995) Carnegie-Mellon University, p. 229, vol. 56.

Kawai, T., et al., "Extension and Shrinkage of Polymer Brush Grafted onto Porous Membrane Induced by Protein Binding", Macromolecules, (2000) p. 1306-1309, vol. 33.

Kim, J.T., et al., "Diffusion and Flow through Polymer-Lined Micropores", Ind. Eng. Chem. Res., (1991) p. 1008-1016, vol. 30.

Kim, J.T., et al., "Hindered Transport Through Micropores with Adsorbed Polyelectrolytes", J. Memb. Sci., (1989) p. 163-182, vol. 47.

Kim, J.H., et al., "Rapid temperature/pH response of porous alginate-g-poly(N-isopropylacrylamide) hydrogels", Polymer, (2002) p. 7549-7558, vol. 43.

Kontturi, K., et al., Modeling of the Salt and pH Effects on the Permeability of Grafted Porous Membranes, Macromolecules, (1996) p. 5740-5746, vol. 29.

Kumar, G. S., et al., "Chelating copolymers containing photosensitive functionalities. 3. Photochromism of cross-linked polymers", Macromolecules, (1985) p. 1525-1530, vol. 18.

Liu, H.C., et al., "Breakthrough of lysozyme through an affinity membrane of cellulose-Cibacron Blue", AIChE Journal, (1994), p. 40-49, vol. 40.

Liu, Q., et al., "Preparation of macroporous poly(2-hydroxyethyl methacrylate) hydrogels by enhanced phase separation", Biomaterials, (2000) p. 2163-2169, vol. 21.

McNeff, C., et al., "High-performance anion exchange of small anions with polyethyleneimine-coated porous zirconia" J. Chrom. A, (1994) p. 201-211, vol. 684.

Mika, A.M., et al., "Acid/base properties of poly(4-vinylpyridine) anchored within microporous membranes", J. Memb. Sci., (1998) p. 129-140, vol. 152.

Mika, A.M., et al., "A new class of polyelectrolyte-filled microfiltration membranes with environmentally controlled porosity", J. Memb. Sci., (1995) p. 37-56, vol. 108.

Mika, A.M., et al., "Calculation of the hydrodynamic permeability of gels and gel-filled microporous membranes", Ind. Eng. Chem. Res., (2001) p. 1694-1705, vol. 40.

Mika, A.M., et al., "Chemical valves based on poly(4-vinylpyridine)-filled microporous membrane", J. Memb. Sci., (1999) p. 45-56, vol. 153.

Mika, A.M., et al., "Poly(4-vinylpyridine)-filled microfiltration membranes: physiochemical properties and morphology", J. Memb. Sci., (1977) p. 221-232, vol. 136.

Mika, A.M., et al., "Porous, polyelectrolyte-filled membranes: Effect of cross-linking on flux and separation", J. Memb. Sci., (1997) p. 81-92, vol. 135.

Mika, A.M., et al., "Salt separation and hydrodynamic permeability of a porous membrane filled with pH-sensitive gel", J. Memb. Sci., (2002) p. 19-30, vol. 206.

Mika, A.M., et al., "Ultra-low pressure water softening: a new approach to membrane construction", Desalination, (1999) p. 149-158, vol. 121.

Mika, A. M., et al., "Ultra-low-pressure water softening with pore-filled membranes", Desalination, (2001) p. 265-275, vol. 140.

Murakami, R., et al., "Properties of poly(vinyl alcohol)/silica hybrid gel particles", Journal of Materials Science Letters, (1995) p. 937-938, vol. 14.

Murdan, S., "Electro-responsive drug delivery from hydrogels", J. Control. Release, (2003) p. 1-17, vol. 92.

Nagaoka, S., "Mechanical properties of composite hydrogels", Polymer Journal, (1989) p. 847-850, vol. 21.

Nakanishi, K., et al., "Porous gel coatings obtained by phase separation in ORMOSIL system", Mater. Res. Soc. Symp. Proc., (2000) p. CC7.6.1-CC7.6.11, vol. 628.

Oxley, H. R., et al., "Macroporous hydrogels for biomedical applications: Methodology and morphology", Biomaterials, (1993) p. 1064-1072, vol. 14, No. 14.

Padmavathi, N.Ch., et al., "Structural Characteristics and Swelling Behavior of Poly(ethylene glycol) Diacrylate Hydrogels", Macromolecules, (1996) p. 1976-1979, vol. 29.

Pandey, A.K., et al., "Formation of Pore-Filled Ion-Exchange Membranes with in-situ Crosslinking: Poly(vinylbenzyl ammonium salt)-Filled Membranes", J. Polym. Sci. Part A Polymer Chemistry, (2001) p. 807-820, vol. 39.

Petsch, D., et al., "Selective adsorption of endotoxin inside a polycationic network of flat-sheet microfiltration membranes", J. Mol. Recog., (1998) p. 222-230, vol. 11.

Rabelo, D., et al., Polym. Bull., (1994) p. 479, 487 and 493, vol. 33.

Rounds, M. A., et al., "Poly(Styrene-Divinylbenzene)-Based Strong Anion-Exchange Packing Materila for High-Performance Liquid Chromatography of Proteins", J. Chrom., (1987) p. 25-38, vol. 397.

Saito, K., "Charged Polymer Brush Grafted onto Porous Hollow-Fiber Membrane Improves Separation and Reaction in Biotechnology" Sep. Sci. Tech., (2002) p. 535-554, vol. 37(3).

Sata, T., et al., "Modification of properties of ion exchange membranes", Coll. Sci., (1978) p. 757-769, vol. 256.

Schaefer, D. W., et al., "Dynamics of Semiflexible Polymers in Solution", Macromolecules, (1980) p. 1280-1290, vol. 13.

Smets, G., et al., "Chemical Reactions in Solid Polymeric Systems. Photomechanical Phenomena", Pure Appl. Chem., (1974) p. 225-238, vol. 39.

Smets, G., et al., "Photochromic Phenomena in the Solid Phase", Adv. Polym. Sci., (1983) p. 17-44, vol. 50.

Smets, G., et al., "Photomechanical Effects in Photochromic Systems", Pure Appl. Chem. (1978) vol. 50, p. 845-856.

Stachera, D., et al., "Acid recovery using diffusion dialysis with poly(4-vinylpyridine)-filled microporous membranes", J. Memb. Sci., (1998) p. 119-127, vol. 148.

Svec, F., et al., "Kinetic Control of Pore Formation in Macroporous Polymers. Formation of "Molded" Porous Materials with High Flow Characteristics for Separations or Catalysis", Chem. Mater., (1995) p. 707-715, vol. 7.

Svec, F., et al., "Molded Rigid Monolithic Porous Polymers: An Inexpensive, Efficient, and Versatile Alternative to Beads for the Design of Materials for Numerous Applications", Industrial and Engineering Chemistry Research, (1999) p. 34-48, vol. 38, No. 1, ACS Publishers, US.

Svec, F., et al., "Reactive macroporous membranes based on glycidyl methacrylate-ethylene dimethacrylate copolymer for high-performance membrane chromatography", Angew. Makromol. Chem., (1991) p. 167-176, vol. 188.

Tennikov, M.B., et al., "Effect of porous structure of macroporous polymer supports on resolution in high-performance membrane chromatography of proteins", Journal of Chromatograph A, (1998) p. 55-64, vol. 798.

Tennikov, T.B., et al., "High-performance membrane chromatography. A novel method of protein separation", J. Liquid Chromatography, (1990), p. 63-70, vol. 13.

Tennikov, T.B., et al., "High-performance membrane chromatography: highly efficient separation method for proteins in ion-exchange, hydrophobic interaction and reversed-phase modes", J. Chromatography, (1993) p. 279-288, vol. 646.

Tennikov, T.B., et al., "High-performance membrane chromatography of proteins, a novel method of protein separation", Chromatography, (1991) p. 97-107, vol. 555.

Van Krevelen, D.W., Properties of Polymers, 2nd ed., (1976) Elsevier, Amsterdam, Chapter 7, p. 129.

Viklund, C., et al., Fast ion-exchange HPLC of proteins using porous poly(glycidyl methacrylate-co-ethylene dimethacrylate) monoliths grafted with poly(2-acrylamido-2-methyl-1-propanesulfonic acid), Biotechnol. Progress, (1977) p. 597-600, vol. 13.

Von Gottberg, A., "Von Gottberg A. New high-performance spacers in electrodialysis reversal (EDR) systems", Proceedings—Annual Conference, American Water Works Association (1998) p. 215-229, vol. B, Water Resources.

Wang, L., "Internal surface coating and photochemical modification of polypropylene microfiltration membrane", Ph.D. Thesis, McMaster University, Hamilton, ON, Canada, (1997).

Wang, Q.C., et al., "Polymeric Porogens Used in the Preparation of Novel Monodispersed Macroporous Polymeric Separation Media for High-Performance Liquid Chromatography", Analytical Chemistry, (1992) p. 1232-1238, vol. 64, No. 1, ACS Publishers., US.

Warwick, T., et al., "Soft X-ray spectromicroscopy development for materials science at the Advanced Light Source", J. Electron Spectrosc, (1977) p. 85-98, vol. 84.

Warwick, T., et al., "A scanning transmission x-ray microscope for materials science spectromicroscopy at the advanced light source", Rev. Sci. Inst., (1998) p. 2964-2973, vol. 69, No. 8.

Webber, R.M., et al., "Hydrodynamic Studies of Adsorbed Diblock Copolymers in Porous Membranes", Macromolecules, (1990) p. 1026-1034, vol. 23.

Yang, H., "Analysis of Protein Purification Using Ion-Exchange Membranes", Industrial and Engineering Chemistry, (1999) p. 4044-4050, vol. 38.

Zhang, H.-Q., et al., "Synthesis and Characterization of Novel Photochromic Side-chain Liquid Crystalline Polymethacrylates Containing Para-nitroazobenzene Group", Eur. Polymer J., (1998) p. 1521-1529, vol. 34, No. 10.

Brandrup et al. (edited by), Polymer Handbook Chapter VII, Wiley and Sons, New York (1999).

Kabra et al., "Synthesis of fast response, temperature-sensitive poly (N-isopropylacrylamide) gel," Polymer Communications, 32(11):322-323 (1991).

Lozinsky, Vladimir I., et al.; "The potential of polymeric cryogels in bioseparation," Bioseparation 10:163-188 (2002).

Okano et al., "Intelligent biointerface: remote control for hydrophilic-hydrophobic property of the material surfaces by temperature," presented at the Third ICIM/ECSSM '96, Lyon '96, pp. 34-41 (1996).

Park et al., "Estimation of Temperature-Dependent Pore Size in Poly(N-isopropylacrylamide) Hydrogel Beads," Biotechnology Prog., 10:82-86 (1994).

"The Water Molecule," Martin Chaplin, Apr. 3, 2001; printed from the internet on Apr. 21, 2011; <<http://xnet.rrc.mb.ca/rcharney/the%20water%20molecule.htm>>.

Ultrafiltration, Nanofiltration and Reverse Osmosis, SDWF, <<www.safewater.org>>; cited by Examiner on Apr. 20, 2010, during prosecution of U.S. Appl. No. 11/547,736; no date provided.

International Search Report dated Jun. 21, 2005 (mailed Jul. 20, 2005) from PCT/CA05/000518.

International Search Report dated Aug. 5, 2005 (mailed Aug. 23, 2005) from PCT/CA05/000880.

Supplementary European Search Report dated Apr. 26, 2007 (mailed May 8, 2007) from EP 05 732 196.0.

STABLE COMPOSITE MATERIAL COMPRISING SUPPORTED POROUS GELS

FIELD OF THE INVENTION

This invention relates to a stable composite material comprising a supported macroporous crosslinked gel, which gel entraps a stabilising polymer.

BACKGROUND OF THE INVENTION

The combination of polymer chains and gels, commonly referred to as "snake-in-a cage" or "snake-cage" systems, has been reported previously, and such combinations have been used to achieve various purposes.

In 1957, Hatch et al. disclosed a new type of ion-exchange resin, which they termed a snake-cage polyelectrolyte (Hatch et al., *Industrial and Engineering Chemistry* (1957), vol. 49, 1812-19). This compound consisted of a crosslinked polymer network carrying a fixed charge, in which was contained a physically trapped linear polyelectrolyte of the opposite charge. The crosslinked network used in this work was a commercial cationic resin, Dowex 1, constituting the "cage", in which the linear anionic polymer "snake" was trapped. Amphoteric polymeric compositions prepared from snake-cage resins were later disclosed in U.S. Pat. No. 3,875,085.

The snake-cage polyelectrolytes have some unusual properties through which they differ from conventional ion-exchangers. One of these properties is that they reversibly absorb both anions and cations simultaneously from aqueous solutions of electrolytes. The absorbed electrolytes can then be removed by merely washing with water. Unlike conventional ion-exchange resins, the snake-cage resins swell in concentrated solutions and shrink in diluted solutions.

While attempts were made to entrap polyelectrolytes in neutral cages, these attempts all met with failure unless the polyelectrolyte was grafted into the cage network or unless the polyelectrolyte was crosslinked. In the absence of grafting or crosslinking, the polyelectrolytes could be extracted almost completely from a neutral cage-forming polymer. In one example of such a system, an ionically crosslinked polyelectrolyte was entrapped in a poly(vinyl alcohol) gel to enhance the water vapor transport through a membrane (WO 02/38257). Again, in the absence of crosslinking, the polyelectrolyte could be extracted from the neutral poly(vinyl alcohol) gel on standing in water.

It is of note that the previously reported snake-in-cage systems consisted of dense polymeric gels, rather than macroporous gels, as will be presently discussed.

Improvement of mechanical properties of hydrogels by encasing a hydrophobic polymer in the gel network was also reported by Nagaoka (*Polymer Journal* (1989), vol 21, 847-850). Hydrogels consisting of hydrophilic crosslinked poly(N-vinyl-2-pyrrolidone) encasing hydrophobic polymers of either cellulose acetate, poly(methyl methacrylate), poly(vinyl chloride), poly(vinyl butyral), polyurethane, or polystyrene, were synthesized and evaluated for use in medical applications (optical lenses), and were compared with poly(2-hydroxyethyl methacrylate), currently used in these applications. The hydrogels were synthesized using the snake-in-cage method, in which a specified amount of the hydrophobic polymer was dissolved in N-vinyl-2-pyrrolidone (monomer) containing diethylene glycol dimethacrylate (crosslinker), and polymerized. Based on measurements of tensile strength, elongation at break, initial tensile modulus, and $H_2O$ content, hydrogels incorporating either cellulose acetate or poly(methyl methacrylate) were superior to poly(2-hydroxyethyl methacrylate). The transmittance of visible light of 500 nm through the hydrogels of thickness 100 µm was greater than 98%, and hydrogels also displayed $H_2O$ permeability of over ten times that of poly(2-hydroxyethyl methacrylate). The high light transparency of these snake-in-cage hydrogels indicates that the gels were homogeneous as they need to be to work as optical lenses. The water permeability given in the paper also confirms this conclusion, as the reported water permeability, converted into Darcy hydrodynamic permeability, was in the order of $1.2 \times 10^{-20}$ m$^2$. Such low permeability is comparable with that of very dense gel-filled membranes that were previously reported by Mika et al. (*Industrial and Engineering Chemistry Research* (2001), vol. 40, 1694-1705), and as such these gels represent a different class of materials than those presently disclosed.

BRIEF SUMMARY OF THE INVENTION

In one aspect, the present invention provides a composite material comprising:
  a support member that has a plurality of pores extending therethrough, and
  a macroporous crosslinked gel that is located in, and fills, the pores of the support member, in which crosslinked gel is entrapped a stabilising polymer that is substantially water-insoluble but water swellable.

The above composite material, which comprises an entrapped stabilising polymer, is referred to herein as a "stable composite material". Mention herein of composite materials comprising "a stabilising polymer" also encompasses the embodiments where two or more stabilising polymers are comprised in the composite material.

In another aspect, the invention provides a process for the separation of substances by means of the stable composite material described herein.

In another aspect, the invention provides a process for solid phase chemical synthesis, wherein the stable composite material serves as the solid phase in the pores of which the chemical synthesis occurs.

In another aspect, the invention provides a process for growth of a microorganism or cell, wherein the stable composite material serves as a solid support in the pores of which the growth occurs.

In yet another aspect, the invention provides a process for preparing a composite material as described herein, the process comprising:
a) introducing into the pores of the support member a solution or suspension of
  i) a monomer and a crosslinking agent that can combine to form a macroporous gel, and a stabilising polymer, or
  ii) a crosslinkable polymer and a crosslinking agent that can combine to form a macroporous gel, and a stabilising polymer, and
b) reacting the monomers and the crosslinking agent or the polymer and the crosslinking agent to form a macroporous crosslinked gel that fills the pores of the support member and entraps the stabilising polymer.

In a further aspect, the invention provides a process for chromatographic filtration of a solution or suspension containing two or more species of different size that are dissolved or suspended in a fluid, which process comprises (a) passing the fluid through a stable composite material as described herein, so that species of the smallest size pass through the composite material but larger species do not pass through the composite material, and (b) changing an environmental condition to increase the size of the pores in the responsive macroporous gel so that species of a next larger size pass through the composite material.

By "entrapped" is meant that the stabilising polymer is held within the macroporous crosslinked gel, without being covalently bonded to the gel. The stabilising polymer that is entrapped also has an affinity for the macroporous gel, by which is meant that the stabilising polymer does not form a separate phase from the macroporous gel, but is incorporated within it.

By "substantially water-insoluble, but water swellable" is meant that the stabilizing polymer is poorly soluble in water or in aqueous solutions, while still retaining enough solubility to display an increased volume when contacted with water. Because of its entrapped state and insolubility in water, the stabilising polymer is substantially retained within the gel when water or an aqueous solution is passed through the composite material.

The macroporous gel fills the pores of the support laterally, i.e. substantially perpendicular to the direction of the flow through the composite material. By "fill" we mean that, in use, essentially all liquid that passes through the composite material must pass through the macroporous gel. A support member whose pores contain macroporous gel to such an amount that this condition is satisfied is regarded as filled. Provided that the condition is met that the liquid passes through the macroporous gel, it is not necessary that the void volume of the support member be completely occupied by the macroporous gel.

The porous support member, or host, may be hydrophilic or hydrophobic and can be, for example, in the form of a membrane, a chromatography bed, or a filtration bed. The support member provides the mechanical strength to support the macroporous gel. The macroporous gel provides a low resistance to hydraulic flow, enabling high flow rates to be achieved with low reductions in pressure across the composite material. The macroporous gel also provides the separating function of the composite material in chromatographic and filtration applications.

A gel is a crosslinked polymer network swollen in a liquid medium. The swelling liquid prevents the polymer network from collapsing and the network, in turn, retains the liquid.

Gels are typically obtained by polymerization of a monomer and a polyfunctional compound (a crosslinker), or by crosslinking a crosslinkable polymer, in a solvent which is a good solvent for the formed polymer network and which swells the polymer network. The polymer chains in such a network can be assumed to be uniformly distributed throughout the whole volume of the network and the average distance between the chains, known as mesh size, is determined by the crosslinking density. As the concentration of the crosslinker is increased, the density of crosslinks in the gel also increases, which leads to a smaller mesh size in the gel. The smaller mesh size results in a higher resistance to the flow of liquids through the gel. As the concentration of the crosslinker is increased further, the constituents of the gel begin to aggregate, which produces regions of high polymer density and regions of low polymer density in the gel. Such gels exhibit what has been called microheterogeneity. This aggregation normally causes the gel to display a higher permeability to liquids, as the flow of liquids takes place primarily through the areas in the gel that have a lower polymer density. The low density areas of the gels are defined as draining regions while the higher density aggregates are called non-draining regions. When the gel is formed in a poor solvent or in the presence of a porogen it can develop regions in which there is essentially no polymer. These regions are referred to as "macropores" in the present specification.

It is possible to compare the hydrodynamic (Darcy) permeability of a particular composite material of the invention with a reference material. The reference material is obtained by filling the pores of a support member identical with that of the composite material with a homogeneous gel of essentially the same chemical composition and the similar mass as the gel of the composite material, that is a gel composed of the same monomers formed in a good solvent, but crosslinked only to such an extent that the gel remains homogeneous and aggregation into regions of high and low polymer density does not occur. Composite materials having macroporous gels display hydrodynamic (Darcy) permeabilities that are at least one order of magnitude higher than those of the corresponding reference materials, and in some instances the permeabilities are more than two or even more than three orders of magnitude higher. In this specification, a composite material of the invention whose hydrodynamic (Darcy) permeability is at least an order of magnitude greater than that of the corresponding reference material is said to have a permeability ratio greater than 10.

The permeability ratio is closely related to the size of the macropores in the composite material. For size-exclusion separations such as ultrafiltration, the permeability ratio can be fairly close to 10. In other applications, for example adsorption, synthesis or cell growth, where larger macropores are used, the permeability ratio can reach, in some embodiments, values of 100 or greater, or even 1000 or greater. In some instances it is possible to calculate the hydrodynamic permeability of homogeneous gels, in accordance with the teachings of Mika A. M. and Childs R. F. Calculation of the hydrodynamic permeability of gels and gel-filled microporous membranes, Ind. Eng. Chem. Res., vol. 40 (2001), p. 1694-1705, incorporated herein by reference. This depends upon data for the particular gel polymer being available.

From the hydrodynamic permeability there can be derived the hydrodynamic radius, defined as the ratio of the pore volume to the pore wetted surface area. It can be calculated from the hydrodynamic (Darcy) permeability using the Carman-Kozeny equation as given, for example, in the book J. Happel and H. Brenner, Low Reynolds Numbers Hydrodynamics, Noordhof of Int. Publ., Leyden, 1973, p. 393, incorporated by reference herein. It is necessary to assume a value for the Kozeny constant and for the purpose of these calculations the inventors assume a value of 5. Composite materials of the invention, containing macroporous gels, are found to have a hydrodynamic radius more than three times as high as the hydrodynamic radius of the corresponding reference material.

From the definition of the hydrodynamic permeability it can be derived that two composite materials of the same thickness will have hydrodynamic fluxes at the same pressure that will have the same ratio as their permeability ratio.

The size of macropores in the gel can be within a broad range, from a few nanometers to several hundred nanometers. Preferably, the porous gel constituent of the composite material has macropores of average size between about 10 and about 3000 nm, has volume porosity between 30 and 80% and a thickness equal to that of the porous support member. In some embodiments, the average size of the macropores is, for example, between 10 ad 1500 nm, preferably between 25 and 1500 nm, more preferably between 50 and 1000 nm, and most preferably the average size of the macropores is about 700 nm.

In the absence of a support member, the macroporous gels used in the present invention may be non-self supporting, and they may change or even lose their porosity when dried. By inserting the macroporous gel within a porous support member, mechanical-strength is conferred upon the macroporous gel. The utilization of macroporous gels creates a composite material that permits larger molecules, such as biological molecules, to enter the macropores and the solution containing such molecules to traverse the gel at a high flux.

By a "responsive composite material" is meant a composite material which comprises a macroporous gel whose pore-size can be controlled by varying specific environmental conditions.

BRIEF DESCRIPTION OF THE DRAWINGS

FIG. 23A displays a sample of the composite material prior to drying while and FIG. 23B displays a sample of the composite material after drying.

FIGS. 24A and 24B provide images of the same material but at different magnifications.

FIGS. 25A and 25B provide images of the same material but at different magnifications.

DETAILED DESCRIPTION OF THE INVENTION

Figure 1:
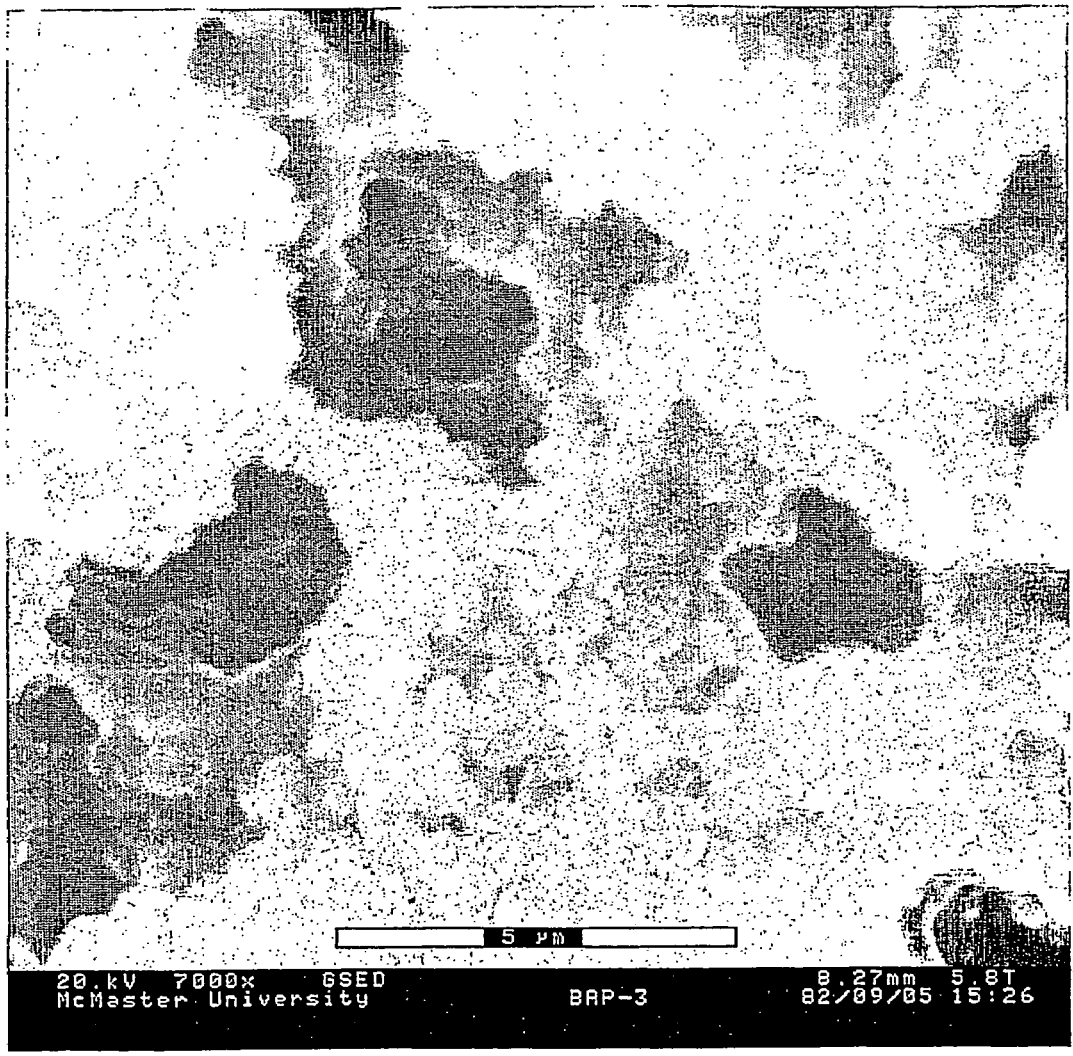
FIG. 1 is an environmental scanning electron microscope (ESEM) image of a macroporous poly(APTAC) gel.

Composite materials comprising supported porous gels have previously been described in U.S. patent application Ser. No. 10/769,953 filed on Feb. 2, 2004, which document is incorporated herein by reference.

General Characteristics

Preferably, the macroporous gel is anchored within the support member. The term "anchored" is intended to mean that the gel is held within the pores of the support member, but the term is not necessarily restricted to mean that the gel is chemically bound to the pores of the support member. The gel can be held by the physical constraint imposed upon it by enmeshing and intertwining with structural elements of the host, without actually being chemically grafted to the host or support member, although in some embodiments, the macroporous gel may become grafted to the surface of the pores of the support member.

It will be appreciated that as the macropores are present in the gel that fills the pores of the support member, the macropores must be smaller than the pores of the support member. Consequently, the flow characteristics and separation characteristics of the composite material are dependent on the characteristics of the macroporous gel, but are largely independent of the characteristics of the porous support member, with the proviso, of course, that the size of the pores present in the support member is greater than the size of the macropores of the gel. The porosity of the composite material can be tailored by filling the support member with a gel whose porosity is primarily controlled by the nature and amounts of monomer or polymer, crosslinking agent, reaction solvent, and porogen, if used. As pores of the support member are filled with the same macroporous gel material, there is achieved a high degree of consistency in properties of the composite material, and for a particular support member these properties are determined largely, if not entirely, by the properties of the macroporous gel. The net result is that the invention provides control over macropore-size, permeability and surface area of the composite materials.

The number of macropores in the composite material is not dictated by the number of pores in the support material. The number of macropores in the composite material can be much greater than the number of pores in the support member, although the macropores are smaller than the pores in the support member. As mentioned above, the effect of the pore-size of the support material on the pore-size of the macroporous gel is generally quite negligible. An exception to this is found in those cases where the support member has a large difference in pore-size and pore-size distribution, and where a macroporous gel having very small pore-sizes and a narrow range in pore-size distribution is sought. In these cases, large variations in the pore-size distribution of the support member are weakly reflected in the pore-size distribution of the macroporous gel. As such it is preferable to use a support member with a somewhat narrow pore-size range in these situations.

The properties of the composite materials can be tuned, by adjusting the average pore diameter of the macroporous gel. For some purposes, for example ultrafiltration by means of size exclusion, small pores may be required. For other purposes, for example use as a solid support for a chemical synthesis involving fast-kinetics, large pores may be required. The size of the macropores is mainly dependent on the nature and concentration of the crosslinking agent, the nature or the solvent or solvents in which the gel is formed, the amount of any polymerization initiator or catalyst and, if present, the nature and concentration of porogen.

Generally, as the concentration of crosslinking agent is increased, the size of the macropores in the gel is also increased. For example, the molar ratio of polyfunctional compound(s)(crosslinking agent) to monomer(s) may be in the range of from about 5:95 to about 70:30, preferably in the range of from about 10:90 to about 50:50, and more preferably in the range of from about 15:85 to about 45:55.

The components of the macroporous gel are introduced into the pores of the support member by means of a liquid vehicle, and solvent selection for in situ polymerization or crosslinking plays a role in obtaining porous gels. Generally, the solvent or solvent mixture should dissolve monomers and polyfunctional compounds, or crosslinkable polymers and crosslinking agents, over a wide range of concentrations. If the solvent is a good solvent for the gel polymer, porosity can only be introduced into the gel by porogen. If, however, there is present a solvent that is a thermodynamically poor solvent or non-solvent, this solvent will act as a porogen. By combining solvents of different affinities to the gel polymer, from a good solvent through a poor solvent to a non-solvent, at different ratios, both porosity and pore dimensions can be altered. In general, the poorer the solvent or the solvent mixture the higher the porosity and the sizes of macropores. Preferably, the solvent or solvent mixture for in situ polymerization contains poor solvent in the range from about 0% to about 100%, more preferably from about 10% to about 90%. Examples of good solvents for poly(2-acrylamido-2-methyl-1-propanesulfonic acid) are water and N,N-dimethylformamide. Examples of poor solvents include dioxane, hydrocarbons, esters, and ketones. An example of a good solvent for poly(acrylamide) is water. Examples of poor solvents include dioxane, alcohols such as methanol, N,N-dimethylformamide, hydrocarbons, esters, and ketones. Preferably, the solvents used are miscible with water.

When the polymerization is carried out using a liquid vehicle that contains non-solvents or poor solvents, the resulting structure is often built of clusters of agglomerated microspheres that form the body of the macroporous gel. The pores in such materials consist of the voids located between clusters (macropores), voids between microspheres in the clusters (mesopores), and pores inside the microspheres themselves (micropores).

Porogens can be broadly described as pore generating additives. Examples of porogens that can be used in the gel-forming reaction include thermodynamically poor solvents or extractable polymers, for example poly(ethyleneglycol), or surfactants, or salts. Porogens are known in the art, and a person skilled can determine, using standard experimental techniques and without exercise of any inventive faculty, which porogens are suitable to prepare macroporous gels for use in a desired composite material.

There is no simple way to predict accurately the structure parameters of porous gels obtained under given conditions, but qualitative rules are available to give some guidance. Generally, the mechanism of porous gel formation via polymerization of one or more monomers and crosslinkers involves, as a first step, an agglomeration of polymer chains to give nuclei. The polymerization continues both in the nuclei and in the remaining solution to form microspheres which grow in size by capturing newly precipitated nuclei and polymers from the solution. At some point, the microspheres become interconnected with each other in large clusters that form the body of the macroporous gel. The poorer the solvent quality the faster nucleation occurs during the gel-forming process. If the number of nuclei formed is very large, as in the case of high concentration of a polymerization initiator, smaller pores may be expected. If, however, the number of nuclei is smaller and the reaction kinetics is such that the nuclei can grow larger, large pores are formed in the gel. High concentration of a crosslinker usually causes early nucleation. The nuclei, however, may be too highly crosslinked to be able to swell with the monomers, grow and coalesce in clusters. This may result in very small pores. Because of the different ways that the polymerization may proceed and the polymerization conditions may affect the gel porous structure, a large variety of structures can be obtained but conditions for each of the structures need to be determined experimentally.

In one embodiment, the composite material comprises
   a support member that has a plurality of pores extending therethrough, and
   a macroporous crosslinked gel that is located in, and fills, the pores of the support member, such that a liquid passing through the composite material must pass through the macroporous cross-linked gel, in which crosslinked gel is entrapped a stabilising polymer that is substantially water-insoluble but water swellable;
wherein said macroporous cross-linked gel is formed by reacting one or more monomers/polymers with a sufficient amount of one or more cross-linking agents such that said macroporous gel comprises regions of high polymer density defined by aggregation of the polymer and regions of essentially no polymer, defining macropores.

In one preferred embodiment, the pores in the support member have an average size of about 0.1 to about 25 µm. In another preferred embodiment, the macropores in the macroporous cross-linked gel have an average size between approximately 25 and approximately 1500 nm, and the macroporous gel has a volume porosity between 30 and 80%.

Separations with the Composite Material

In some embodiments of the invention the composite material is used as a separating medium, for example in filtration operations where a liquid to be filtered is passed through the composite membrane and separation of one or more components from the liquid is effected by size exclusion in an uncharged macroporous gel. The separation can further be enhanced by the Donnan exclusion of charged molecules by use of a charged macroporous gel. If the macroporous gel contains a fixed charge and the charge of the solutes can be appropriately adjusted, the solutes can be separated even against their size gradient. For example with a solution containing a mixture of proteins, if a pH value is selected for which one of the proteins in the mixture is at its isoelectric point while the other proteins retain charge of the same sign as the membrane charge, the other proteins can be held back in the retentate because of the charge repulsion with the membrane. By tailoring the conditions for fractionation, good selectivity, even for proteins of the same size, can be obtained.

Separation can also be achieved by the presence of reactive functional groups in the macroporous gel. These functional groups can be used to bear a ligand or other specific binding site that has an affinity to a molecule or ion, including a biomolecule or biomolecular ion. When a liquid containing the particular molecule or ion is passed through the composite material the ligand or specific binding site interacts with the molecule or ion enough to adsorb it. In some cases it is possible to subsequently desorb the captured molecule or ion when the environment around the composite material is subsequently altered, for example by changing the nature of the solvent passed through the macropores of the gel. The binding sites can also include charged groups.

Composition of the Macroporous Gels

The macroporous gels can be formed through the in-situ reaction of one or more polymerisable monomers with one or more crosslinkers, or of one or more crosslinkable polymers with one or more crosslinker to form a crosslinked gel that has macropores of a suitable size. Suitable polymerisable monomers include monomers containing vinyl or acryl groups. For Donnan exclusion, there can be used vinyl or acryl monomers containing at least one polar and/or ionic functional group, or functional group that can be converted into ionic group. For biological affinity there can be used vinyl or acryl monomers containing at least one reactive functional group. Preferred polymerisable monomers include acrylamide, 2-acryloxyethyltrimethylammonium chloride, N-acryloxysuccinimide, N-acryloyltris(hydroxymethyl)methylamine, 2-aminoethyl methacrylate hydrochloride, N-(3-aminopropyl)methacrylamide hydrochloride, butyl acrylate and methacrylate, N,N-diethylacrylamide, N,N-dimethylacrylamide, 2-(N,N-dimethylamino)ethyl acrylate and methacrylate, N-[3-(N,N-dimethylamino)propyl]methacrylamide, N,N-dimethylacrylamide, n-dodecyl acrylate, n-dodecyl methacrylate, dodecyl methacrylamide, ethyl methacrylate, 2-(2-ethoxyethoxy) ethyl acrylate and methacrylate, 2,3-dihydroxypropyl acrylate and methacrylate, glycidyl acrylate and methacrylate, n-heptyl acrylate and methacrylate, 1-hexadecyl acrylate and methacrylate, 2-hydroxyethyl acrylate and methacrylate, N-(2-hydroxypropyl)methacrylamide, hydroxypropyl acrylate and methacrylate, methacrylamide, methacrylic anhydride, methacryloxyethyltrimethylammonium chloride, 2-(2-methoxy)ethyl acrylate and methacrylate, octadecyl acrylamide, octylacrylamide, octyl methacrylate, propyl acrylate and methacrylate, N-isopropylacrylamide, stearyl acrylate, styrene, 4-vinylpyridine, vinylsulfonic acid, N-vinyl-2-pyrrodinone. Particularly preferred monomers include dimethyldiallylammonium chloride, acrylamido-2-methyl-1-propanesulfonic acid (AMPS), (3-acrylamidopropyl) trimethylammonium chloride (APTAC), acrylamide, methacrylic acid (MAA), acrylic acid (AA), 4-styrenesulfonic acid and its salts, acrylamide, glycidyl methacrylate, diallylamine, and diallylammonium chloride.

The crosslinker may be, for example, a compound containing at least two vinyl or acryl groups. Examples of crosslinkers include bisacrylamidoacetic acid, 2,2-bis[4-(2-acryloxyethoxy)phenyl]propane, 2,2-bis(4-methacryloxyphenyl) propane, butanediol diacrylate and dimethacrylate, 1,4-butanediol divinyl ether, 1,4-cyclohexanediol diacrylate and dimethacrylate, 1,10-dodecanediol diacrylate and dimethacrylate, 1,4-diacryloylpiperazine, diallylphthalate, 2,2-dimethylpropanediol diacrylate and dimethacrylate, dipentaerythritol pentaacrylate, dipropylene glycol diacrylate and dimethacrylate, N,N-dodecamethylenebisacrylamide, divinylbenzene, glycerol trimethacrylate, glycerol tris(acryloxypropyl)ether, N,N'-hexamethylenebisacrylamide, N,N'-octamethylenebisacrylamide, 1,5-pentanediol diacrylate and dimethacrylate, 1,3-phenylenediacrylate, poly(ethylene glycol) diacrylate and dimethacrylate, poly(propylene) diacrylate and dimethacrylate, triethylene glycol diacrylate and dimethacrylate, triethylene glycol divinyl ether, tripropylene glycol diacrylate or dimethacrylate, diallyl diglycol carbonate, poly(ethylene glycol) divinyl ether, N,N'-dimethacryloylpiperazine, divinyl glycol, ethylene glycol diacrylate, ethylene glycol dimethacrylate, N,N'-methylenebisacrylamide, 1,1,1-trimethylolethane trimethacrylate, 1,1,1-trimethylolpropane triacrylate, 1,1,1-trimethylolpropane trimethacrylate, vinyl acrylate, 1,6-hexanediol diacrylate and dimethacrylate, 1,3-butylene glycol diacrylate and dimethacrylate, alkoxylated cyclohexane dimethanol diacrylate, alkoxylated hexanediol diacrylate, alkoxylated neopentyl glycol diacrylate, aromatic dimethacrylate, caprolacone modified neopentylglycol hydroxypivalate diacrylate, cyclohexane dimethanol diacrylate and dimethacrylate, ethoxylated bisphenol diacrylate and dimethacrylate, neopentyl glycol diacrylate and dimethacrylate, ethoxylated trimethylolpropane triacrylate, propoxylated trimethylolpropane triacrylate, propoxylated glyceryl triacrylate, pentaerythritol triacrylate, tris(2-hydroxy ethyl)isocyanurate triacrylate, di-trimethylolpropane tetraacrylate, dipentaerythritol pentaacrylate, ethoxylated pentaerythritol tetraacrylate, pentaacrylate ester, pentaerythritol tetraacrylate, and caprolactone modified dipentaerythritol hexaacrylate. Particularly preferred crosslinking agents include N,N'-methylenebisacrylamide, diethylene glycol diacrylate and dimethacrylate, trimethylolpropane triacrylate, ethylene glycol diacrylate and dimethacrylate, tetra(ethylene glycol) diacrylate, 1,6-hexanediol diacrylate, divinylbenzene, poly(ethylene glycol) diacrylate.

The concentration of monomer in the macroporous gel can have an effect on the resiliency of the macroporous gel prepared. A low monomer concentration can lead to a macroporous gel that is non-self supporting. Such non-self supporting gels might be advantageous as adsorbents, as they could lead to gels having greater adsorption capacity. In some embodiments, the monomer concentration is 60% or less, for example about 60, 50, 40, 30, 20, 10 or 5%.

When a crosslinkable polymer is used, it can be dissolved and reacted in-situ in the support with a crosslinking agent to form the macroporous gel. Suitable crosslinkable polymers include poly(ethyleneimine), poly(4-vinylpyridine), poly(vinylbenzyl chloride), poly(diallylammonium chloride), poly (glycidyl methacrylate), poly(allylamine), copolymers of vinylpyridine and dimethyldiallylammonium chloride, copolymers of vinylpyridine, dimethyladiallylammonium chloride, or (3-acrylamidopropyl)trimethylammonium chloride with glycidyl acrylate or methacrylate, of which poly (ethyleneimine), poly(diallylammonium chloride), and poly (glycidyl methacrylate) are preferred. Use of crosslinkable polymers instead of monomers can, in some instances, require a decrease in the concentration of crosslinking agent. In order to retain the large size of the pores in the gel with a lower crosslinking agent concentration, a porogen can be added to the mixture used to prepare the macroporous gel.

The crosslinking agent for reaction with the crosslinkable polymer is selected from molecules containing two or more reactive groups that can react with an atom or group of atoms in the polymer to be crosslinked, such as epoxy groups or alkyl/aryl halides that can react with nitrogen atoms of polyamines, or amine groups that can react with alkyl/aryl halides or epoxy groups of glycidyl-group-containing polymers to be in situ crosslinked. Suitable crosslinkers include ethylene glycol diglycidyl ether, poly(propylene glycol) diglycidyl ether, 1,3-dibromopropane, 1,4-dibromobutane, 1,5-dibromopentane, 1,6-dibromohexane, $\alpha,\alpha'$-dibromo-p-xylene, $\alpha,\alpha'$-dichloro-p-xylene, 1,4-dibromo-2-butene, piperazine, 1,4-diazabicyclo[2.2.2]octane, 1,2-diaminoethane, 1,3-diaminopropane, 1,4-diaminobutane, 1,5-diaminopentane, 1,6-diaminohexane, 1,7-diaminoheptane. 1,8-diaminooctane.

It is also possible to modify polymers containing reactive groups such as an amino, hydroxyl, carboxylic acid, carboxylic acid ester, or epoxy groups with reagents to introduce vinyl groups that can be subsequently polymerized by treatment with a polymerization initiator to form a macroporous gel. Examples of suitable vinyl groups that can be introduced include vinylbenzene derivatives, allyl derivatives, acroyl and methacrolyl derivatives. The crosslinking of these vinyl substituted polymers can in some instances be facilitated by the introduction of further monomers such as acrylamide, N-vinylpyrrolidone, acrylic and methacrylic acids and their salts.

Macromonomers can also be used as monomers or as crosslinking agents. Macromonomers can be polymers or oligomers that have one (monofunctional) or more (crosslinking agent) reactive groups, often at the ends, which enable them to act as a monomer or a crosslinker. For monomers, each macromonomer molecule is attached to the main chain of the final polymer by reaction of only one monomeric unit in the macromonomer molecule. Examples of macromonomers include poly(ethylene glycol)acrylate and poly(ethylene glycol)methacrylate, while examples of polyfunctional macromonomers include poly(ethylene glycol) diacrylate and poly(ethylene glycol)dimethacrylate. Macromonomers preferably have molecular weights of about 200 Da or greater.

Many macroporous gels can be prepared, including neutral hydrogels, charged hydrogels, polyelectrolyte gels, hydrophobic gels, and neutral and functional gels.

If the gel selected is a neutral hydrogel or a charged hydrogel for which water is the swelling liquid medium, the resulting supported macroporous gel is normally quite hydrophilic. Hydrophilic composite materials are preferred as they provide better flow characteristics and impart anti-fouling tendencies to the membranes. Examples of suitable hydrogels include crosslinked gels of poly(vinyl alcohol), poly(acrylamide), poly(isopropylacrylamide), poly(vinylpyrrolidone), poly(hydroxymethyl acrylate), poly(ethylene oxide), copolymers of acrylic acid or methacrylic acid with acrylamide, isopropylacrylamide, or vinylpyrrolidone, copolymers of acrylamide-2-methyl-1-propanesulfonic acid with acrylamide, isopropylacrylamide, or vinylpyrrolidone, copolymers of (3-acrylamidopropyl) trimethylammonium chloride with acrylamide, isopropylacrylamide, or N-vinylpyrrolidone, copolymers of diallyldimethylammonium chloride with acrylamide, isopropylacrylamide, or vinylpyrrolidone. Preferred hydrogels include crosslinked poly(vinyl alcohol), poly(acrylamide), poly(isopropylacrylamide) and poly(vinylpyrrolidone) and crosslinked copolymers of neutral monomers such as acrylamide or N-vinylpyrrolidone with charged monomers such as acrylamide-2-methyl-1-propanesulfonic acid or diallyldimethylammonium chloride.

The macroporous gels can be selected to comprise polyelectrolytes. Like the charged hydrogels, polyelectrolyte gels give hydrophilic composite material, and they also carry a charge. The polyelectrolyte gel can be selected, for example, from crosslinked poly(acrylamido-2-methyl-1-propanesulfonic acid) and its salts, poly(acrylic acid) and its salts, poly(methacrylic acid) and its salts, poly(styrenesulfonic acid) and its salts, poly(vinylsulfonic acid) and its salts, poly (alginic acid) and its salts, poly[(3-acrylamidopropyl)trimethylammonium] salts, poly(diallyldimethylammonium) salts, poly(4-vinyl-N-methylpyridinium) salts, poly(vinylbenzyl-N-trimethylammonium) salts, poly(ethyleneimine) and its salts. Preferred charged gels include crosslinked poly (acrylic acid) and its salts, poly(methacrylic acid) and its salts, poly(acrylamido-2-methyl-1-propanesulfonic acid) and its salts, poly[(3-acrylamidopropyl)trimethylammonium] salts, poly(diallyldimethylammonium) salts, and poly (4-vinylpyridinium) salts.

One of the differences between charged gels and polyelectrolyte gels is that the repeating monomer in the polyelectrolyte gel bears a charge, while in the charged gel, the charge is found in a co-polymerized unit that is randomly distributed through the polymer. The monomer used to form the polyelectrolyte gel or the co-polymer in the charged gel that bears a charge usually has a charge bearing group, but it can also be a non-charge-bearing group that can become charged in a post-gelation process (e.g. quaternization of nitrogen bearing groups). Examples of polymers that can become charged include poly(4-vinylpyridine) which can be quaternized with various alkyl and alkylaryl halides. Suitable alkyl halides include those having up to 8 carbon atoms, for example methyl iodide, ethyl bromide, butyl bromide, and propyl bromide. Suitable alkylaryl halides include benzyl halides, especially benzyl chloride and benzyl bromide. Another polymer that can become charged is poly(vinylbenzyl chloride), which can be quaternized with various amines, for example, lower alkylamines or aromatic amines such as triethylamine, pyridine, azabicyclo[2.2.2]octane, N-methylpyrrolidine, and N-methylpiperidine, and lower hydroxyalkylamines, for example triethanolamine. Yet another polymer that can become charged is poly(glycidyl methacrylate) or poly(glycidyl acrylate), which can react with various amines, for example lower alkylamines such as diethylamine and triethylamine, azabicyclo[2.2.2]octane, N-methylpyrrolidine, and N-methylpiperidine. Alternatively, glycidyl moieties can be converted to sulfonic acid groups by reaction with, for example alkali metal sulfites such as sodium sulfite. A person skilled in the art will appreciate that there are other polymers that are, or can be rendered, charge-bearing.

The macroporous gel can be selected to comprise hydrophobic monomers to permit separations in organic solvents, for example hydrocarbons, especially liquid paraffins such as hexanes. Hydrophobic monomers, such as styrene and its derivatives, for example an alkyl substituted styrene derivative such as para-tertbutyl styrene, can be used to prepare hydrophobic macroporous gels. Copolymers of these monomers can be used.

A macroporous gel comprising hydrophobic monomers can be used to capture molecules from fluids passing through the pores by hydrophobic interactions.

As stated above, the macroporous gels can also be selected to comprise reactive functional groups that can be used to attach ligands or other specific binding sites. These functional macroporous gels can be prepared from crosslinked polymers bearing functional groups, for example epoxy, anhydride, azide, reactive halogen, or acid chloride groups, that can be used to attach the ligands or other specific binding sites. Examples include crosslinked poly(glycidyl methacrylate), poly(acrylamidoxime), poly(acrylic anhydride), poly(azelaic anhydride), poly(maleic anhydride), poly(hydrazide), poly(acryloyl chloride), poly(2-bromoethyl methacrylate), poly(vinyl methyl ketone). Functionality that can be introduced can take the form of antibodies or fragments of antibodies, or alternatively, chemical mimics such as dyes. Functional gels are attractive in biomolecule purifications or separations, as they can offer preferential binding to certain molecules by binding to active sites, while being non-reactive to other molecules, even when there is no significant difference in size between the molecules, examples being affinity ligands selected to bind with some proteins but not others. Affinity ligands that can be attached to porous gels via reactive groups include amino acid ligands such as L-phenylalanine, tryptophan, or L-histidine to separate γ-globulins and immunoglobulins, antigen and antibody ligands such as monoclonal antibodies, protein A, recombinant protein A, protein G, or recombinant protein G to separate immunoglobulins from different media, dye ligands such as cibaron blue or active red to separate albumins and various enzymes, metal affinity ligands such as complexes of iminodiacetic acid (IDA) ligand with $Cu^{2+}$, $Ni^{2+}$, $Zn^{2+}$, or $Co^{2+}$ to separate various proteins such as histidine, lysozyme, or tryptophan from various media.

Responsive Macroporous Gels

Polymers that change their conformation in response to changes in environmental conditions are known. By incorporating the properties of such polymers in the macroporous gel, a composite material with dynamic pore-size is obtained. These composite materials having responsive characteristics are substantially the same as the composite materials described above, except that at least one of the monomers or polymers that form the macroporous gel has a chemical structure which facilitates changes in pore-size.

The changes in the pore-size of the macroporous gel are due to the physical relationship between the support member and the macroporous gel. The composite material can be described as having three distinct zones: (a) the support member, which ideally does not change shape, (b) the incorporated macroporous gel that "fills" the pores of the support member, and (c) the volume within the macropores of the gel, which volume is filled with water or a solvent and in which is found very little or no gel polymer. Under pressure, hydraulic flow occurs through the macropores of the gel, and the flux through the composite material is related to the number of pores in the macroporous gel, the radius of these pores, and the tortuosity of the path of the pores in the macroporous gel through the composite material.

As the degree of swelling of the macroporous gel is changed by an environmental stimulus, the total volume occupied by the macroporous gel is constrained by the fixed total volume defined by the support member. As the overall volume of the macroporous gel is constrained by the support member, by necessity the volume fraction of the gel expands into the area defined by macropores in the gel. As the number of macropores and their tortuosity remain essentially constant with the change in volume fraction of the macroporous gel, the diameter or radius of the macropores themselves must change. If the macroporous or structured gel were unconfined, the environmentally induced changes would cause the total volume of the swollen gel to change. As such it would not follow in this unconfined case that the changes would result in a controllable change in pore-size of the macroporous gel.

The reason behind the change in volume of the macroporous gel is related to interactions between the polymer structures that form the gels, or the interactions between the polymer chains and the solvents or solutes present in the solvent that diffuse into the gel. The changes in the volume occupied by the gel are linked to the conformation adopted by the polymer chains that form the macroporous gels. The natural tendency of the polymer chains is to coil around themselves, which leads to a gel having a smaller volume. If the polymer chains within the gel can be manipulated to uncoil and form a more rigid backbone, the overall volume of the gel will increase. It is thus this coiling/uncoiling which is affected by the environmental stimuli that are applied to the responsive composite material.

The volume changes of the pores can either be "continuous" or "discontinuous". A continuous volume change takes place over a relatively large change in the triggering environmental condition and where there exists at least one stable volume near the transition between the swollen and collapsed state. Preferably, a continuous volume change will go through a multitude of stable transition volumes between the swollen and the collapsed state. A discontinuous volume change in gels is characterised by the reversible transition from swollen to collapsed state taking place over an extremely small change in the triggering environmental condition, for example, less than 0.1 pH unit or 0.1 degree Celsius. Gels exhibiting discontinuous volume change are called "phase-transition" gels and systems or devices with such gels are often called "chemical valves". Preferably, the responsive macroporous gels according to this embodiment of the invention undergo a "continuous" volume change through discrete stable volumes that can be utilized to control the pore-size of the gel.

Of the environmental stimuli that can be used to change the pore-size in the responsive macroporous, mention is made of pH, specific ions, ionic strength, temperature, light, electric fields, and magnetic fields. The effect of each stimulus, and examples of monomers that react to such a stimulus, will be described in more detail below.

One stimulus that can be utilised to change the pore-size of responsive macroporous gel is the pH of the solution being passed through the pores of the gel. A change in the pH of the solution will affect the pore-size of the gel if the gel comprises weak acids or weak bases. In such cases, the natural tendency of the polymer chain within the gel to coil around itself will be balanced by the repulsion between the charged groups (weak acidic or basic groups) along the length of the polymer chain. Variations in the amount of charge along the chain cause large changes in conformation of the polymer chain, which in turn causes changes in the volume occupied by the gel. Changes in the pH of the solution are effective at controlling the amount of repulsion along the polymer chain, as they change the degree of ionisation of the charged groups. A gel comprising weak acid groups becomes less ionised as the pH is lowered and the gel contracts. Conversely, a weak base becomes more ionised as the pH is lowered and the chain elongates or stretches to give a swollen gel.

Examples of monomers that have weak acid functionality include acrylic acid, methacrylic acid, itaconic acid, 4-vinylbenzoic acid, bisacrylamidoacetic acid, and bis(2-methacryloxyethyl) phosphate. Examples of monomers that have weak base functionality include 2-aminoethyl methacrylate hydrochloride, N-(3-aminopropyl)methacrylamide hydrochloride, 2-(tert-butylamino)ethyl methacrylate, diallylamine, 2-(N,N- diethylamino)ethyl methacrylate, 2-(N,N-dimethylamino) ethyl acrylate, 2-(N,N-dimethylamino)ethyl methacrylate, 1-vinylimidazole, and 4-vinylpyridine. Glycidyl methacrylate derivatized hyaluronate-hydroxyethyl acrylate based hydrogels can also be used to prepare composite materials that are pH responsive [Inukai M., Jin Y., Yomota C., Yonese M., Chem. Pharm. Bull., (2000), 48:850-854; which is hereby incorporated by reference].

Variations in pH have little effect on the degree of ionisation of strong acids and bases, and as such, only drastic variations in pH can effect pore-size changes in gels comprising these functionalities.

Another stimulus that can be utilised for changing the pore-size of a responsive macroporous gel is the salt concentration of the solution being passed through the pores of the gel. Similarly to variations in pH, variations in salt concentration will effect pore-size variations in macroporous gels that comprise weak acidic or weak basic groups. The reason for the changes in pore-size, however, does differ slightly. The addition of an ionic solute has the ability to shield the charged groups found on the polymer chain in the gel by the formation of ion-pairs. This lessens the coulombic repulsion between the adjacent charged groups, which allows the chain to relax into a coiled conformation. An increase in salt concentration will shield both a weak acid group and a weak base group. Therefore, when the salt concentration is increased, for example by adding a concentrated salt solution to the bulk solution being passed through the composite material, the shielding effect of the additional ions leads to an increase in pore size. Alternatively, a decrease in salt concentration, such as obtained by diluting the bulk solution being passed through the composite material, will lead to less shielding and a smaller pore size.

Changes in salt concentration can also be used with macroporous gels that comprise strong acid groups and strong basic groups, as these groups are also shielded by the presence of free ionic species.

Examples of monomers that bear weak acid or base groups are listed above. Examples of monomers that have strong acid functionality include 2-acrylamido-2-methyl-1-propanesulfonic acid, sodium 2-methyl-2-propene-1-sulfonate, sodium styrenesulfonate, and sodium vinylsulfonate. Examples of monomers that have strong basic functionality include 2-acryloxyethyltrimethylammonium chloride, diallyldimethylammonium chloride, methacrylamidopropyltrimethylammonium chloride, and 3-methacryloxy-2-hydroxypropyltrimethylammonium chloride.

Ionic functionality (weak/strong acids and bases) may also be introduced in macroporous gels that do not originally bear charged functionalities but that bear instead reactive groups that can be converted into ionic or ionisable moieties in a post-polymerization treatment. Suitable monomers with reactive groups include acrylic anhydride, allyl glycidyl ether, bromostyrene, chloromethylstyrene, chlorostyrenes, glycidyl acrylate, glycidyl methacrylate, 4-hydroxybutyl methacrylate, 2-hydroxyethyl acrylate, methacryloyl chloride. For example, a macroporous gel comprising a glycidyl acrylate or methacrylate group can be treated with diethylamine to introduce weak base functionality or with sodium sulfite in an iso-propanol/water mixture to introduce strong acid (sulfonic acid) functionality.

Another stimulus that can be used to change the pore-size of a responsive macroporous gel is the temperature of the gel. Various methods are available for changing the temperature of the macroporous gel, one of which includes changing the temperature of a liquid flowing through the pores of the macroporous gel. While the change in overall gel volume for temperature dependant gels is again due to the control of the coiling or uncoiling of the polymer chains that form the gel, the contraction or expansion of the gel is not linked to the presence of charged groups on the polymer chain. For temperature dependant gels, the amount salvation of the polymer chain controls the conformation of the polymer chain. At lower temperatures the chains are solvated, which allows an elongated conformation of the polymer chain. As the temperature is increased, an entropic desolvation takes place causing the chains to coil and contract. Therefore, increases in temperature lead to larger pore sizes in the gel while decreases in temperature lead to smaller pore sizes.

Macroporous gels that comprise hydrophobic monomers are most suitable for use in temperature dependant systems, as salvation effects are markedly observed for polymers that have hydrophobic functionality. Examples of monomers that have hydrophobic functionality include N-(propyl)acrylamide, N-(tert-butyl)acrylamide, butyl acrylates, decyl acrylates, decyl methacrylates, 2-ethylbutyl methacrylate, n-heptyl acrylate, n-heptyl methacrylate, 1-hexadecyl acrylate, 1-hexadecyl methacrylate, n-hexyl acrylate, n-hexyl methacrylate, and N-(n-octadecyl)acrylamide. Gels displaying thermal response can also be prepared from sulphated hyaluronic acid-based gels (see Barbucci R., Rappuoli R., Borzacchiello A., Ambrosio L., J. Biomater. Sci.—Polym. Ed., (2000), 11:383-399), incorporated herein by reference.

Light is another stimulus that can be used to change the pore-size of the responsive macroporous gel. Light induced changes are due to photoisomerizations in the backbone or the side-chains of the polymer chains that form the gel. These photoisomerizations cause a change in either the conformation and local dipole moment, or in the degree of ionisation through light induced electron transfer reactions. One type of monomer that is suitable for use in light controlled systems comprises unsaturated functionalities than can undergo a trans-cis isomerization on irradiation. Examples of photoresponsive monomers that go through cis-trans conformation and dipole changes include 4-(4-oxy-4'-cyanoazobenzene) but-1-yl methacrylate, 6-(4-oxy-4'-cyanoazobenzene)hex-1-yl methacrylate, 8-(4-oxy-4'-cyanoazobenzene)oct-1-yl methacrylate, 4-[ω-methacryloyloxyoligo(ethyleneglycol)]-4'-cyanoazobenzene, 4-methacryloyloxy-4'-{2-cyano-3-oxy-3-[ω-methoxyoligo(ethyleneglycol)]prop-1-en-1-yl}azobenzene, and methacrylate monomers containing a mesogenic group and a photochromic para-nitroazobenzene group. It is also possible to incorporate the photoresponsive moeity in the crosslinker instead of the monomer. Examples of photoresponsive crosslinkers that go through cis-trans conformation and dipole changes include 4,4'-Divinylazobenzene, N,N'-bis(β-styrylsulfonyl)-4,4'-diaminoazobenzene, 4,4'-bis(methacryloylamino)azobenzene, 4,4'-dimethacryloylazobenzene, and bis((methacryloyloxy)methyl)spirobenzopyran.

The pore-size of the gel can also be altered by subjecting the macroporous gel to an electric field or to an electrical current. The response of the gel to electrochemical current changes is closely related to the pH systems described above. This close relationship is due to the fact that the passage of an electrochemical current through an aqueous system causes a "water splitting" reaction, which reaction leads to changes in the pH of the aqueous system. Electrical current can be passed through a composite material of the invention e.g. by placing an electrode at either end of the composite material. When current differential is applied to the electrodes, water molecules will separate and concentrations of $H^+$ and $HO^-$ will increase at their respective electrodes. As described earlier, changes in pH can be used to control the pore-size of macroporous gels that comprise weak acid or weak base functionalities, which control is linked to the relationship between the ionisation of these functionalities and the coiling/uncoiling of the polymer chains that form the gel. Examples of weak acidic and weak basic monomers are given above.

Changes in gel volume due to fluctuations in an electrical field have been previously observed, such as in Murdan S., *J. Control. Release*, (2003), 92:1-17; and in Jensen M., Hansen P. B., Murdan S., Frokjaer S., Florence A. T., *Eur. J. Pharm. Sci.*, (2002), 15:139-148, which are hereby incorporated by reference. While the exact process through which the gel volume is changed by the application of an electrical field is not yet well defined, the volume change itself is well documented. Chondroitin 4-sulphate (CS) is an example of a monomer that is responsive to electrical field fluctuations.

In some embodiments, the various stimuli response systems can be combined to offer gels that respond to more than one stimulus. An example of such a combined system can be prepared by combining a charged polymer (weak/strong acid or base) with a hydrophobic monomer. The macroporous gel resulting from such a combination will display responses to changes in salt concentration, changes in solution pH (when weak acids or bases are used), and changes in temperature. When combining different monomers, it is possible that the responsiveness of the gel to a single of the stimuli will be diminished, as the concentration of the monomer that responds to that particular stimulus will be lowered in the gel.

The magnitude of the response expressed by the macroporous gels, when various stimuli are applied to the gel, depends many different variables, a few of which are discussed below:

The responsiveness of the macroporous gel is dependent on the concentration of the crosslinking agent. Generally, as the concentration of crosslinking agent is increased, the size of the macropores in the responsive gel is also increased, but the range of pore-size changes is decreased. This relationship is fairly straightforward, as a higher concentration of crosslinks within the gel will limit the amount of coiling and uncoiling that will be available to the responsive gel. The molar ratio of crosslinking agent(s) to monomer(s) may be in the range of from about 5:95 to about 40:60, preferably in the range of from about 7.5:92.5 to about 10:90, and more preferably in the range of from about 10:90 to about 25:75.

Certain stimuli naturally evoke a broader range of response in the gel, as they more effectively affect the conformation of the polymer chains that form the gel. For example, variations in pH or temperature evoke a strong response from the appropriate macroporous gels, while changes in salt concentrations and light intensity evoke a slightly smaller response.

The concentration of the responsive monomer in the gel also affects the level of response demonstrated by the gel. Preferably, the responsive macroporous gels are composed of one or more responsive monomers and of one or more neutral monomers. The presence of a neutral monomer is important in those systems that have a very strong response to changes in the environmental conditions, as such systems often display discontinuous responses in pore-size (valve-effects). Addition of a neutral monomer attenuates the response, permitting a more controlled change in pore-size.

Preferably, the molar ratio of the neutral monomers to the molar ratio of responsive monomers in the responsive macroporous gel is in the range from 5:95 to 95:5, more preferably in the range from 25:75 to 75:25, and more preferably in the range from 40:60 to 60:40. Suitable neutral monomers include acrylamide, N-acryloylmorpholine, N-acryloxysuccinimide, 2-acrylamido-2-(hydroxymethyl)-1,3-propanediol, N,N-diethylacrylamide, N,N-dimethylacrylamide, 2-(2-ethoxyethoxy)ethyl acrylate, 2-ethoxyethyl methacrylate, 2,3-dihydroxypropyl methacrylate, 2-hydroxyethyl methacrylate, N-(2-hydroxypropyl)methacrylamide, hydroxypropyl methacrylate, methacrylamide, N-[tris(hydroxymethyl)methyl]-1-methacrylamide, N-methylmethacrylamide, N-methyl-N-vinylacetamide, poly(ethylene glycol) monomethacrylate, N-iso-propylacrylamide, N-vinyl-2-pyrrolidone.

Porous Support Member

A variety of materials can be used to form the support member; however, apart from materials such as cellulose and some of its derivatives, most of these materials are strongly or relatively hydrophobic. Hydrophobic filtration membranes are not usually desired for use with aqueous systems, as they can lead to higher membrane fouling tendencies. The more inert and cheaper polymers such as polyolefins, for example (poly(ethylene), poly(propylene) poly(vinylidene difluoride)) can be used to make microporous membranes, but these materials are very hydrophobic. In some embodiments of the present invention, the hydrophobicity of the support member does not affect the degree of fouling experienced by the composite material as the flow of liquid through the composite material takes place primarily in the macropores of the gel.

In some embodiments, the porous support member is made of polymeric material and contains pores of average size between about 0.1 and about 25 µm, and a volume porosity between 40 and 90%. Many porous substrates or membranes can be used as the support member but the support is preferably a polymeric material, and it is more preferably a polyolefin, which, while hydrophobic, is available at low cost. Extended polyolefin membranes made by thermally induced phase separation (TIPS), or non-solvent induced phase separation are mentioned. Hydrophilic supports can also be used, including natural polymers such as cellulose and its derivatives. Examples of suitable supports include SUPOR® polyethersulfone membranes manufactured by Pall Corporation, Cole-Parmer® Teflon® membranes, Cole-Parmer® nylon membranes, cellulose ester membranes manufactured by Gelman Sciences, Whatman® filter and papers.

In some other embodiments the porous support is composed of woven or non-woven fibrous material, for example a polyolefin such as polypropylene. An example of a polypropylene non-woven material is commercially available as TR2611A from Hollingsworth and Vose Company. Such fibrous woven or non-woven support members can have pore sizes larger than the TIPS support members, in some instances up to about 75 µm. The larger pores in the support member permit formation of composite materials having larger macropores in the macroporous gel. Composite materials with larger macropores can be used, for example, as supports on which cell growth can be carried out. Non-polymeric support members can also be used, such as ceramic-based supports. The porous support member can take various shapes and sizes.

In some embodiments, the support member is in the form of a membrane that has a thickness of from about 10 to about 2000 µm, more preferably from 10 to 1000 µm, and most preferably from 10 to 500 µm. In other embodiments, multiple porous support units can be combined, for example, by stacking. In one embodiment, a stack of porous support membranes, for example from 2 to 10 membranes, can be assembled before the macroporous gel is formed within the void of the porous support. In another embodiment, single support member units are used to form composite material membranes, which are then stacked before use.

Preparation of Composite Materials

The composite materials of the invention can be prepared by simple, single step methods. These methods can, in some instances, use water or other benign solvents, such as methanol, as the reaction solvent. The methods also have the benefit of using rapid processes that lead to easier and continuous manufacturing possibilities. The composite material is also potentially cheap.

The composite materials of the invention can be prepared, for example, by mixing one or more monomers, one or more polymers, or mixtures thereof, one or more crosslinking agents, optionally one or more initiators and optionally one or more porogens, in one or more suitable solvents. The solution produced is preferably homogeneous, but a slightly heterogeneous solution can be used. The mixture is then introduced into a suitable porous support, where a gel forming reaction takes place. Suitable solvents for the gel forming reaction include, for example, water, dioxane, dimethylsulfoxide (DMSO), dimethylformamide (DMF), acetone, ethanol, N-methylpyrrolidone (NMP), tetrahydrofuran (THF), ethyl acetate, acetonitrile, toluene, xylenes, hexane, N-methylacetamide, propanol, and methanol. It is preferable to use solvents that have a higher boiling point, as these solvents reduce flammability and facilitate manufacture. It is also preferable that the solvents have a low toxicity, and they can be readily disposed of after use. An example of such a solvent is dipropyleneglycol monomethyl ether (DPM).

In some embodiments, it is possible to use dibasic esters (esters of a mixture of dibasic acids) as the solvent. Dibasic esters (DBEs) are especially suitable for preparing gels based on polyacrylamide monomers. This solvent system has an unexpected characteristic in that it is poorly soluble in water, which differs from the other solvents used which are essentially completely water miscible. While water miscible solvents offer advantages in terms of solvent removal after fabrication, water immiscible solvents such as DBE's are good replacements, in certain cases, for solvents such as dioxane that are volatile, flammable, and toxic.

In some embodiments, components of the gel forming reaction react spontaneously at room temperature to form the macroporous gel. In other embodiments, the gel forming reaction must be initiated. The gel forming reaction can be initiated by any known method, for example through thermal activation or U.V. irradiation. The reaction is more preferably initiated by U.V. irradiation in the presence of a photoinitiator, as this method has been found to produce larger macropores in the gel, and it accelerates the gel forming reaction more than the thermal activation method. Many suitable photoinitiators can be used, of which 2-hydroxy-1[4-2 (hydroxyethoxy)phenyl]-2-methyl-1-propanone (Irgacure 2959*), and 2,2-dimethoxy-2-phenylacetophenone (DMPA) are preferred. Other suitable photoinitiators include benzophenone, benzoin and benzoin ethers such as benzoin ethyl ether and benzoin methyl ether, dialkoxyacetophenones, hydroxyalkylphenones, α-hydroxymethyl benzoin sulfonic esters. Thermal activation requires the addition of a thermal initiator. Suitable thermal initiators include 1,1'-azobis(cyclohexanecarbonitrile) (VAZO® catalyst 88), azobis(isobutyronitrile) (AIBN), potassium persulfate, ammonium persulfate, and benzoyl peroxide.

If the reaction is to be initiated by U.V. irradiation, a photoinitiator is added to the reactants of the gel forming reaction, and the support member containing the mixture of monomer, crosslinking agent and photoinitiator is subjected to U.V. irradiation at wavelengths of from 250 nm to 400 nm, for a period of a few seconds to a few hours. With certain photoinitiators, visible wavelength light may be used to initiate the polymerization. To permit the initiation, the support material must have a low absorbance at the wavelength used, to permit transmittance of the UV rays through the support. Preferably, the support and macroporous gel reagents are irradiated at 350 nm for a few seconds to up to 2 hours.

Preferably, thermally initiated polymerization is carried out at 60-80° C. for a few minutes up to 16 hours.

The rate at which polymerization is carried out has an effect on the size of the macropores obtained in the macroporous gel. As discussed earlier, when the concentration of crosslinker in a gel is increased to sufficient concentration, the constituents of the gel begin to aggregate to produce regions of high polymer density and regions with little or no polymer, which latter regions are referred to as "macropores" in the present specification. It is this mechanism which is affected by the rate of polymerization. When polymerization is carried out slowly, such as when a low light intensity in the photopolymerization, the aggregation of the gel constituents has more time to take place, which leads to larger-pores in the gel. Alternatively, when the polymerization is carried out at a high rate, such as when a high intensity light source is used, there is less time available for aggregation and smaller pores are produced.

Once the composite materials are prepared, they can be washed with various solvents to remove any unreacted components and any polymer or oligomers that are not anchored within the support. Solvents suitable for the washing of the composite material include water, acetone, methanol, ethanol, and DMF.

Uses of the Composite Material

The composite material of the invention can find use in many different applications, where a liquid is passed through the macropores of the gel. The liquid passed through the macropores can be selected from, for example, a solution or a suspension, such as a suspension of cells or a suspension of aggregates.

In some embodiments, the composite materials can be used to perform separations. Uses include size exclusion separations such as ultrafiltration and microfiltration systems. The composite material of the invention is advantageous in these types of applications because of the wide range of pore-sizes available, and the ease with which composite materials with different pore-sizes can be made. In some embodiments, it is preferred that the composite materials used for size-exclusion separations are not fully occupied, i.e. that while all or substantially all the liquid that flows through the composite material flows through the macroporous gel, the void volume of the support member is not completely occupied by the macroporous gel. Composite materials having a non-fully occupied void volume where the density of the macroporous gel is greater at or adjacent to a first major surface of the support member than the density at or adjacent to a second major surface of the support member are referred to as being asymmetric.

In those embodiments where the macroporous gel bears a charge, the combination of macropore surface charge and of controlled macropore size produces a composite material that can be used in Donnan type exclusion separations. In these instances composite materials are produced that have high charge densities coupled with high hydraulic flows (flux). The high charge densities, coupled with high permeability, can be useful, for example, in adsorption of metal ions by giving composite materials with high ion-exchange capacities. The examples will demonstrate that these composite materials can also be used for the recovery of proteins and other related molecules and that the composite materials of the invention exhibit high binding capacities.

Composite materials of the invention are also suitable for the separation of biomolecules, such as proteins, from solution, as the biomolecules may have specific interactions with ligands or binding sites found in the macropores of the composite materials. The specific interactions may involve electrostatic interactions, affinity interactions of hydrophobic interactions. Examples of molecules or ions, including biological molecules or ions, that can be separated include proteins such as albumins, e.g., bovine serum albumin, and lysozyme, but they can also be used in the separation of supramolecular assemblies such as viruses and cells. Examples of other biomolecules that can be separated include γ-globulins of human and animal origins, immunoglobulins such as IgG, IgM, or IgE of both human and animal origins, proteins of recombinant or natural origin including protein A, polypeptides of synthetic or natural origin, interleukin-2 and its receptor, enzymes such as phosphatase, dehydrogenase, etc., monoclonal antibodies, trypsin and its inhibitor, albumins of different origins, e.g., human serum albumin, chicken egg albumin, etc., cytochrome C, immunoglobulins, myoglobulin, recombinant human interleukin, recombinant fusion protein, nucleic acid derived products, DNA and RNA of either synthetic or natural origin, and natural products including small molecules. Biomolecule separations occur mostly in the macropores of the gel, but they can also take place, albeit at a slower rate, within the gel itself.

Some composite materials can be used as a reversible adsorbent. In these embodiments, a substance, for example a biomolecule, that is adsorbed in the macropores or in the mesh (micropore) of the gel can be released by changing the liquid that flows through the macroporous gel. Variations in the gel composition can be used to control the properties of the gel in terms of uptake and release of adsorbed substances. Another advantage of the composite material of the invention is that it can be made in the form of a membrane, and membrane-based biomolecule recovery is easier to scale up, less labor intensive, more rapid, and has lower capital costs than the commonly used conventional packed column chromatography techniques.

Some composite materials can also be used as solid supports for chemical synthesis or for cell growth. The reactants or nutrients required for these processes can either continuously flow through the macropores of the composite material, or they can be left to reside inside the macropores and then pushed out at a later time. In one embodiment, composite materials can be used in the stepwise production of peptides. In such an application, amino acids are attached to the macropore surface, and amino acid solutions are sequentially passed through the macropores to prepare peptide chains. The formed peptide can then be cleaved from the support by passing a suitable solvent through the macropores. Supports currently used to carry out this type of synthesis consist of beads with small pores that offer slow diffusion characteristics. The composite materials of the invention have a more uniform pore structure, and they have through pores wherein the flow of liquids is not controlled diffusion.

Application areas include but are not limited to pharmaceuticals, including biotechnology, food, beverage, fine chemicals, and the recovery of metal ions.

Uses of Responsive Composite Materials

The composite materials that comprise responsive macroporous gels (responsive composite materials) are preferably used to fractionate fluid components based on a size-exclusion mechanism. By this mechanism, steric hindrance is exerted on the convection and diffusion of a molecule or particle approaching the pores of a filtering device. The impediment to the transport is related to the ratio of the pore radius in the filter to the radius of the molecule or particle. When this ratio approaches to 1:1, molecules or particles will be completely retained by the filtering device. By changing the pore radius, molecules or particles of different sizes are permitted to pass through the pore and fractionation by size is achieved.

The responsive composite materials are well adapted to size exclusion mechanisms as the pores of these materials have a narrow pore-size distribution. This means that size exclusion separations can be achieved for molecules that have molecular weights that are much closer than normally permitted by conventional ultrafiltration/microfiltration membranes. In some embodiments, the size difference between the molecules being separated by the responsive composite materials of the invention can be as low as about 0.9 nm. In other embodiments, the resolution is as low as about 0.5 nm. While some of the known ultrafiltration membranes do have narrow pore-size distributions (e.g. track etched membranes), these membranes have the disadvantage of being costly and of having relatively low fluxes.

In those embodiments where the composite materials are hydrophilic, the composite materials are well adapted to the size-separation of proteins as there is little or no adsorption of molecules to the composite material. Normally, proteins are prone to non-specific binding. Such responsive composite materials are thus suitable for the separation of a multi-component protein mixture into discrete fractions based only on the size of the protein fractions. This separation of proteins through an exclusively size-exclusion method differs from the methods known in the art for separating proteins, where differences in size are used in conjunction with other physicochemical effects such as electrostatic charge, electrostatic double layer, and hydrophobic interaction effects, which physiochemical effects can lead to non-specific binding or even denaturation of the protein. Use of the composite material to separate proteins on a size-exclusion basis thus avoids the denaturation of the protein or its loss due to irreversible binding. The separation of proteins with the responsive composite material of the invention is a very gentle process that does not involve strong interactions between the protein and the separation medium, which permits the recovery of proteins with higher overall efficiencies, a major factor in the economics of therapeutic protein recovery.

One example of separations using the responsive composite materials is the separation of human serum albumin (HSA) (size of 60 kDa) from human immunoglobulin G (IgG) (size of 160 kDa). Size based separations of proteins are possible at fixed environmental conditions. With the responsive macroporous gel in a swollen or partially swollen state, e.g., at a low salt concentration in the feed with gels having weak acid, or base functionalities, the protein with the lower molecular weight (e.g., human serum albumin) can be freely transmitted through the composite material, while the protein with the higher molecular weight (e.g., human immunoglobulin G) can be retained. When operated at a fixed environmental condition, the ultrafiltration process generates two product streams, and the fixed environment mode is suitable for fractionating binary mixtures, i.e. one protein from another.

The responsive composite materials of the invention can also be used to generate more than two product streams through size-based separations utilising the dynamic pore-size capabilities of the responsive composite material. This multi-component separation is possible as the change in membrane pore-size in response to change in environmental condition is gradual. When operated in this mode (i.e. with change in environmental condition), the process is suitable for separating proteins from a multi-protein mixture. In such a process, the environment is changed either in a stepwise fashion or gradually by appropriately altering the environment of the responsive gel. For example, changing the pH of the bulk medium used to carry out the filtration process using binary or ternary buffer systems can bring about a change in pore-size, and hence a sequential size based separation. When operated in the step change mode, each step will generate a fraction, each fraction containing proteins smaller than in the next fraction. If n number of fractions are generated, (n−1) of these will be obtained in the permeate and the $n^{th}$ fraction will be in the retentate.

The multi-component separations presented above represent a completely new use of ultra- and nano-filtration membranes. This type of multi-component separation is also referred to as chromatographic filtration. Some specific applications of this new type of separation include:

(a) fractionation of hen egg white components;
 (i) Lysozyme (MW 14,100);
 (ii) Ovalbumin (MW 47,000);
 (iii) Avidin (MW 68,300)
 (iv) Conalbumin (MW 80,000);
(b) fractionation of human plasma proteins;
 (i) Human serum albumin (HSA, MW 67,000);
 (ii) Human immunoglobulin G (HIgG, MW 155,00);
 (iv) Other human immunoglobulins (e.g. HIgM, MW >300,000);
(c) fractionation of dextran into molecular weight based fractions;
(d) fractionation of PEG into molecular weight based fractions;
(e) fractionation of polymers into molecular weight based fractions; and
(f) fractionation of micron-sized particles into size based fractions.

While the composite materials of the present invention are quite suitable for the separation of bulk materials, they can also be used to separate components on a smaller volume scale. For example, the responsive composite material can be used to separate biochemical substances such as antibodies, other bioactive proteins, hormones, polysaccharides and nucleic acids, prior to analysis. Many of the currently used biospecific analytical methods, e.g. Enzyme Linked Immuno Sorbent Assay (ELISA) are based on the binding of the above substances, or the binding of substances which biospecifically interact with these substances (e.g. antibodies, antigens, ligands, and substrate analogues), onto solid surfaces such as polystyrene (as in ELISA) or onto synthetic membranes (as in immuno-blotting). The detection limits of these tests are frequently limited by the surface area available in devices such as microwell plates or blotted sections of flat sheet membranes. Another limitation imposed by attachment of material onto solid surfaces is the likelihood of steric hindrance affecting the biospecific recognitions on which these tests are based. Biospecific analytical methods which rely on solution phase recognition and binding are also available, e.g. Radio Immuno Assay (RIA). These methods frequently rely on the use of porous synthetic membranes for retaining and enriching substances which are to be analyzed. However, the fixed nature of the permeability of these membranes could prove to be a limiting factor. The use of responsive composite materials would facilitate sequential removal of substance from solutions containing substances to be analyzed and thus facilitate analysis which would not be feasible with fixed permeability membranes. The responsive membranes can also be utilised to facilitate removal from test solutions of substances which are likely to interfere with the assays.

While the responsive composite materials are especially suitable for use in size-exclusion separation, they can nonetheless be used in Donnan type separations and specific binding separations by the incorporation of appropriate monomers or polymers in the macroporous gel.

The responsiveness of composite material also permits the ability to open the pores of a membrane (made from the composite material) after use, and to then return and readjust the pores to their initial values by reversing the environmental change. Opening of the pores facilitates the cleaning of these membranes by removing a fouling material, thereby prolonging the effective use of the membrane.

Stabilising Polymers, and Stable Composite Materials

In some embodiments of the macroporous gel-comprising composite materials, particularly for very hydrophilic macroporous-gels, drying of the macroporous gel leads to a change in the properties of the gel. In some instances, drying of these composite materials causes damage to the gel in the form of cracking, which causes random, uncontrolled changes in the effective pore size of the macroporous gel. As long-term storage, manipulation or transportation of the composite materials is preferably carried out with dried samples, retention of porosity and morphology upon rewetting of the composite materials is desirable. The problem of drying-induced damage to gels has typically been solved by the introduction of humectants such as glycerol to the gel prior to drying. In order to prevent microorganism growth during membrane storage that might result from the presence of a humectant, antimicrobial components are also typically added. These additives are in most cases undesirable, as they need to be washed out prior to use, and some of the antimicrobial additives, e.g. sodium azide, are corrosive to brass fittings. Therefore, there is need for a solution that avoids the known treatments while providing composite materials that can be dried for storage, transportation, and assembly without any damage and changes to their dimensions.

It has now been found that stable composite materials can be obtained by adding a substantially water-insoluble but water swellable stabilising polymer to the crosslinked macroporous gel. This stabilising polymer is entrapped in, but not covalently bonded to, the macroporous gel network. The entrapped polymer chains in the gel network prevent the gel from collapsing and cracking on drying, which permits rapid rewetting of the composite material to its original morphology.

The relative balance between water-insolubility and water swellability of the stabilising polymer can be measured through a three-dimensional cohesion parameter, $\delta_t$, A which is a relationship between solvent and polymer properties (Rabelo, D.; Coutinho, F. M. B. *Polym. Bull.* (1994), 33, 479.; Rabelo, D.; Coutinho, F. M. B. *Polym. Bull.* (1994), 33, 487.; Rabelo, D.; Coutinho, F. M. B. *Polym. Bull.* (1994), 33, 493). The three-dimensional cohesion parameter considers the contributions from dispersive, $\delta_d$, dipolar, $\delta_p$, and hydrogen bonding, $\delta_h$, interactions, according to equation:

$$\delta_t^2 = \delta_d^2 + \delta_p^2 + \delta_h^2$$

In a three-dimensional diagram the solvent and polymer can be represented by two points, and the solvent-polymer affinity can be described by the distance $d_0$ between these two points (Rabelo, D.; Coutinho, F. M. B. *Polym. Bull.* (1994), 33, 479)

$$d_0^2 = 4(\delta_{d1}-\delta_{d2})^2 + (\delta_{p1}-\delta_{p2})^2 + (\delta_{h1}-\delta_{h2})^2$$

The indices 1 and 2 represent the solvent and polymer, respectively.

Many of the cohesion parameters are tabulated in the literature (Barton A. F. M. In *CRC Handbook of Solubility Parameters and Other Cohesion Parameters,* 2nd ed.; CRC Press: Boca Raton, Fla., 1991). Those parameters that are not available can be estimated using a group contribution method according to Hoftyzer-Van Krevelen and Hoy (Grulke, E. A. In *Polymer Handbook,* 4th ed.; Brandrup, J., Immergut E. H., Grulke, E. A., Eds.; Wiley-Interscience: New York, 1999; Chapter VII, p 675.; Van Krevelen. D. W. In *Properties of Polymers,* 2nd ed.; Elsevier: Amsterdam, 1976; Chapter 7, p 129). In case of multifunctional polymers, the average cohesion parameters of n contributing groups can be calculated according to the following equation (Rabelo, D.; Coutinho, F. M. B. *Polym. Bull.* (1994), 33, 487):

$$\delta_i = \phi_1\delta_{1i} + \phi_2\delta_{2i} + \ldots \phi_n\delta_{ni}$$

whereas $\phi$ represents the volume fractions, and the index i, the type of dispersive interaction (d, p, and h).

The literature (Rabelo, D.; Coutinho, F. M. *B. Polym. Bull.* (1994), 33, 479) defines good solvents with $d_o < 10.0$, intermediate solvents with $10.0 < d_0 < 12.7$, and poor solvents with $d_0 > 12.7$.

In the present application, the affinity between the stabilising polymer and water is depicted by the symbol $d_0(H_2O)$, which represents an affinity parameter, as described above, where the solvent is water. Preferably, the stabilising polymer of the invention has a $d_0(H_2O)$ value of from 12 to 40, and more preferably, from 12 to 25.

This balance between water-insolubility and water swellability of the stabilising polymer can be achieved in various polymers by choosing appropriate monomers or co-monomers. In some instances, the sought after balance is achieved by using one or more monomers (co-monomers) which have a weak interaction with water, such as neutral monomers that have strong dipole moments or an ability to form hydrogen-bonds. Neutral monomers bearing amide groups fall within this category. In other instances, a co-monomer having a hydrophobic character can be combined with a hydrophilic monomer, such as a charged monomer, to obtain a polymer that achieves the required balance of water insolubility and water swellability.

Examples of stabilising polymers include cellulose derivatives such as cellulose acetate, cellulose acetate butyrate, cellulose acetate propionate, 2-hydroxyethyl cellulose and ethyl cellulose. Further examples of stabilising polymers include polyesters such as poly(ethylene adipate), polyethylene glycol terephthalate, poly(L-lactide), poly(DL-lactide) and poly(dl-lactide-co-glycolide), poly(ethylene-co-vinyl alcohol) (EVAL) (which can have, for example, an ethylene content of 27, 32, 38, or 44 mol-%), polyamides such as poly(hexamethyleneadipamide) (Nylon 6/6) and poly(hexamethylenesebacamide) (Nylon 6/10), polyacrylates such as poly(2-hydroxyethyl methacrylate) and poly(2-hydroxypropyl methacrylate), polyhydroxystyrene (poly(4-vinylphenol), aromatic poly(ether sulfone), and poly(vinyl alcohol) 40% hydrolyzed (Mowiol 40-88). Still further examples of stabilising polymers include water-insoluble, partially charged polymers such as sulfonated polyetherether ketone (S-PEEK, <86% sulfonation), sulfonated poly(phenylene oxide) (S-PPO, <70% sulfonation), sulfonated polysulfone (S-PS; <70% sulfonation), aminated polysulfone (<70% amination), partially aminated poly(phenylene oxide) (Q-PPO; <70% amination), partially protonated or alkylated poly(4-vintlpyridine) (Q-P4VP; <30% protonation or alkylation), and copolymers of neutral and charged monomers such as poly(ethylene-co-acrylic acid) (which can have, for example, 5, 10, 15, or 20 wt-6 of acrylic acid). Preferably, the stabilising polymer is an ethylene-co-vinyl alcohol copolymer or cellulose acetate.

The water-insolubility/water swellability balance of certain cellulose derivatives, such as cellulose acetate, can be controlled through the degree of acetylation of the polymer. In some instances, a degree of acetylation of from about 29 to about 61 wt-% is preferred.

While the stabilising polymer can be either linear or branched, branched polymers are in some instances preferred as they are more easily retained within the macroporous gel due to an increased amount of entanglement with the gel. In addition, the stabilising polymer preferably has a molecular weight of from 5,000 to 500,000, more preferably of from 40,000 to 150,000. However, these ranges for molecular weight of the stabilising polymer are not meant to be limiting, as the molecular weight and the amount of branching required will be dictated by the nature of the macroporous gel, the nature of the stabilising polymer and the nature of the solvent being eluted through the composite material. As long as the stabilising polymer meets the requirement that it be substantially water-insoluble but water swellable, it is to be included as part of the present invention.

While it is possible for the stabilising polymer to be slightly crosslinked, the level of crosslinking is balanced against the requirement that the stabilising polymer remain in the same phase as the macroporous gel. An increase in the amount of crosslinking leading to the production of a separate phase of stabilising polymers is to be avoided.

Preferably, the stabilising polymer is present in the composite material in an amount of from 5% to 50% by weight, based on the combined weight of monomer, crosslinker and polymer in the macroporous gel. More preferably, the stabilising polymer is present in an amount of from 5 to 30, even more preferably from 10 to 25.

To aid in the preparation of composite materials comprising stabilising polymers, it is preferable that the composite material be soluble in the solvent used to prepare the macroporous gel. As the stabilising polymer is fairly stable to increases in temperature, the solvent used to prepare the macroporous gel can be heated to aid in the dissolution of the stabilising polymer.

It has also been observed that the stabilising polymer plays an additional role in that it not only stabilises the gel mechanically, but it also acts as a porogen. This double role of the stabilising polymeric is particularly attractive in that it reduces the amount of material that has to be washed out and subsequently disposed of prior to using the composite material.

EXAMPLES

The following examples are provided to illustrate the invention. It will be understood, however, that the specific details given in each example have been selected for purpose of illustration and are not to be construed as limiting the scope of the invention. Generally, the experiments were conducted under similar conditions unless noted.

Experimental

Materials Used

The monomers used were acrylamide (AAM), 2-acrylamido-2-methyl-1-propanesulfonic acid (AMPS), (3-acrylamidopropane)trimethylammonium chloride (APTAC), diallyldimethylammonium chloride (DADMAC), ethylene glycol dimethacrylatecrylate (EDMA), glycidyl methacrylate (GIA), N,N'-methylenebisacrylamide (BIS), methacrylic acid (MAA), acrylic acid (AA), trimethylolpropane triacrylate (TRIM), 2-hydroxyethylmethacrylate (HEMA), and N-vinylpyrrolidone (NVP). The crosslinkable polymers used were branched poly(ethylene imine) (BPEI) of an average molecular weight (MW) of 25000 Da, poly(ethylene glycol) (PEG) of average molecular weight of 200, 1000, 2000, 4000 and 10000 Da, and poly(allylammonium hydrochloride) (PAH) of an average molecular weight of 60000 Da. The crosslinker used for BPEI was ethylene glycol diglycidyl ether (EDGE). The stabilising polymers used were ethylene-co-vinyl alcohol copolymers (EVAL) and cellulose acetate (CA). The polymeric porogen used was poly(ethylene glycol) (PEG) of average molecular weight 8000 Da.

The solvents used were acetone (Ac), dipropylene glycol monomethyl ether (DPM), 2-propanol (IPA), cyclohexanol (CHX), methylene chloride ($CH_2Cl_2$), deionized water, 1,4-dioxane, N,N-dimethylformamide (DMF), dodecanol (DDC), glycerol, methanol, 1-octanol, and 1-propanol.

The free radical polymerization initiators used were 2-hydroxy-1-[4-(2-hydroxyethoxy)phenyl]2-hydroxy-2-methyl-1-propane-1-one (Irgacure® 2959), 2,2-dimethoxy-2-phenylacetophenone (DMPA), and 1,1"-azobis(cyclohexanecarbonitrile) (VAZO® catalyst 88).

Proteins used were bovine serum albumin (BSA), lysozyme, human serum albumin (HSA) and human immunoglobulin (HIgG).

Other chemicals used were acryloyl chloride, hydrochloric acid, sodium azide, sodium chloride, sodium hydroxide, triethylamine, tris(hydroxymethyl)aminomethane (TRIS), 4-morpholineethanesulfonic acid (MES) and buffers (Tris Buffer).

The porous supports used were poly(propylene) thermally induced phase separation (TIPS) membranes PP1545-4 with an average pore diameter of 0.45 µm, thickness of 125 µm, and porosity of 85 vol-%, produced by 3M Company, and PP1183-3X of an average pore diameter of 0.9 µm, thickness of 87 µm, and porosity of 84 vol-%, both produced by 3M Company, and non-woven meltblown poly(propylene) TR2611A of a mean pore flow diameter of 6.5 µm, thickness of 250 µm, and porosity of 89.5 vol-1 produced by Hollingworth & Vose Company.

Preparation of Composite Materials

The composite materials of the invention can be prepared according to the following general procedure. A weighed support member was placed on a poly(ethylene terephthalate) (PET) or poly(ethylene) (PE) sheet and a monomer or polymer solution was applied the sample. The sample was subsequently covered with another PET or PE sheet and a rubber roller was run over the sandwich to remove excess solution. In situ gel formation in the sample was induced by polymerization initiated by irradiation with the wavelength of 350 nm for the period of 10 to 120 minutes or by heating the sandwich at 60-80° C. for 2 hours. The irradiation was typically carried out using a system containing four 12" long lamps, approx. 1.5" spaced and emitting light at 365 nm with the output energy of approx. 0.1 Watt/inch. The system was equipped with a small fan to dissipate the heat (no other temperature control). The irradiated sample was located at approx. 5" distance from the lamps. In case when preformed polymer and in situ crosslinking was used to form the gel, the sandwich was left at room temperature until the crosslinking reaction was completed, typically for 2-16 hours. The resulting composite material was thoroughly washed with a suitable solvent or a sequence of solvents and stored in a 0.1 wt-% aqueous solution of sodium azide to prevent bacterial growth. In order to determine the amount of gel formed in the support, the sample was dried in vacuum at room temperature to a constant mass. The mass gain due to gel incorporation was calculated as a ratio of an add on mass of the dry gel to the initial mass of the porous support. Alternatively, the composite materials were also dried in an oven at 70-80° C. for 60 minutes.

In some instances, rewetting of the dried composite materials was studied, and this was carried out placing flat the samples on a water surface and subsequently measuring the time required to completely wet the sample. The samples were left in water for 15 minutes, after which time their mass and dimensions were again measured. The hydrodynamic permeability of the rewetted samples was then re-tested.

Flux Measurements

Water flux measurements through the composite materials were carried out after the samples had been washed with water. As a standard procedure, a sample in the form of a disk of diameter 7.8 cm was mounted on a sintered grid of 3-5 mm thickness and assembled into a cell supplied with compressed nitrogen at a controlled pressure. The cell was filled with deionized water or another feed solution and a desired pressure was applied. The water that passed through the composite material in a specified time was collected in a pre-weighed container and weighed. All experiments were carried out at room temperature and at atmospheric pressure at the permeate outlet. Each measurement was repeated three or more times to achieve a reproducibility of ±5%.

The water flux, $Q_{H2O}$ (kg/m² h), was calculated from the following relationship:

$$Q_{H_2O} = \frac{(m_1 - m_2)}{A \cdot t}$$

where $m_1$ is the mass of container with the water sample, $m_2$ is the mass of container, A is the active membrane surface area (38.5 cm²) and t is the time.

The composite material of the invention may have water flux values that are smaller than those of the unfilled support member, with possible flux reduction of about a factor of two to about a factor of a few hundred depending on the application. For ultrafiltration application, the flux may be reduced by a factor of about ten to about a few hundred.

The hydrodynamic Darcy permeability, k (m²) of the membrane was calculated from the following equation $$k = \frac{Q_{H_2O}\eta\delta}{3600 d_{H_2O}\Delta P}$$

where η is the water viscosity (Pa·s), δ is the membrane thickness (m), $d_{H2O}$ is the water density (kg/m³), and ΔP (Pa) is the pressure difference at which the flux, $Q_{H2O}$, was measured.

The hydrodynamic Darcy permeability of the membrane was used to estimate an average hydrodynamic radius of the pores in the porous gel. The hydrodynamic radius, $r_h$, is defined as the ratio of the pore volume to the pore wetted surface area and can be obtained from the Carman-Kozeny equation given in the book by J. Happel and H. Brenner, Low Reynolds Number Hydrodynamics, Noordhof Int. Publ., Leyden, 1973, p. 393:

$$k = \frac{\varepsilon r_h^2}{K}$$

where K is the Kozeny constant and ε is the membrane porosity. The Kozeny constant K≈5 for porosity 0.5<ε<0.7. The porosity of the membrane was estimated from porosity of the support by subtracting the volume of the gel polymer.

Protein Adsorption/Desorption Experiment

Protein adsorption experiments were carried out with two proteins, namely, bovine serum albumin (BSA) and lysozyme. In the case of experiments with a positively charged composite material in the form of a membrane, the membrane sample was first washed with distilled water and subsequently with a TRIS-buffer solution (pH=7.8). In an adsorption step, a composite material sample in a form of a single membrane disk of diameter 7.8 cm was mounted on a sintered grid of 3-5 mm thickness in a cell used for water flux measurements and described above. A BSA solution, comprising from 0.4 to 0.5 mg BSA per ml of buffer solution, was poured to the cell to give a 5 cm head over the composite material. This hydrostatic pressure of 5 cm was kept constant by further additions of the BSA solution. In a modification of this method, the cell was pressurised with compressed nitrogen. The flow rate was measured by weighing the amount of permeate as a function of time. Typical values varied between 1 and 5 ml/min. Permeate samples were collected at 2-5 min intervals and analyzed by UV analysis at 280 nm. Following the adsorption step, the composite material in the cell was washed with about 200 ml of the TRIS-buffer solution, and desorption was carried out with a TRIS-buffer solution containing 1M NaCl at 5 cm head pressure or under a controlled pressure of compressed nitrogen. The permeate samples were collected at 2-5 min intervals and tested by UV analysis at 280 nm for BSA content.

For negatively charged composite materials, a solution of lysozyme in a MES buffer solution having a pH of 5.5 and a lysozyme concentration of 0.5 g/L was used in a procedure similar to that described above for BSA and positively charged materials. The flow rate during the protein adsorption was again kept within 1-5 ml/min. Prior to the desorption of the protein, the membrane was washed by passing with 200 ml of the buffer solution. The desorption of the protein was carried out using a MES buffer solution (pH=5.5) containing 1M NaCl in the same way as described above for the desorption of BSA. The lysozyme content in the collected samples was determined by UV spectrophotometry at 280 nm.

In other examples, protein adsorption tests involve stacks of several membranes of diameter of 19 mm mounted into a Mustang® Coin Device manufactured by Pall Corporation and the protein solution was delivered to the membrane stack at controlled flow rate using a peristaltic pump. The permeate fractions were collected and analyzed in the same way as described above. The desorption of the proteins was carried in a similar way as described above, with buffered 1M NaCl delivered to the membrane stack by using the pump instead of gravity or compressed nitrogen pressure.

Protein Separation Experiment

The experimental method used to examine the separation properties of the responsive composite materials of this invention in protein-protein fractionation processes is based on the pulsed injection ultrafiltration technique and its derivatives developed by Ghosh and his co-workers and described in the following articles: R. Ghosh and Z. F. Cui, Analysis of protein transport and polarization through membranes using pulsed sample injection technique, Journal of Membrane Science, vol. 175, no. 1 (2000) p. 75-84; R. Ghosh, Fractionation of biological macromolecules using carrier phase ultrafiltration, Biotechnology and Bioengineering, vol. 74, no. 1 (2001) p. 1-11; and R. Ghosh, Y. Wan, Z. F. Cui and G. Hale, Parameter scanning ultrafiltration: rapid optimisation of protein separation, Biotechnology and Bioengineering, vol. 81 (2003) p. 673-682 and incorporated herein by reference. The experimental set-up used was similar to that used for parameter scanning ultrafiltration as described in article by R. Ghosh, Y. Wan, Z. F. Cui and G. Hale, Parameter scanning ultrafiltration: rapid optimisation of protein separation, Biotechnology and Bioengineering, vol. 81 (2003) p. 673-682.

A binary carrier phase system was used in the ultrafiltration experiments. The starting carrier phase in all the responsive composite material experiments was one with a low salt concentration (typically 5-10 mM NaCl). In all these experiments the carried phase was switched to one with a high salt concentration (typically 1 M NaCl). The change in salt concentration within the membrane module could be tracked by observing the conductivity of the permeate stream. The change in transmembrane pressure gave an idea about the change in membrane hydraulic permeability with change in salt concentration.

Example 1

This example illustrates the formation of an unsupported porous gel, which can be used as the macroporous gel to prepare the composite material of the invention.

A solution containing 3.33 g of (3-acrylamidopropane) trimethylammonium chloride (APTAC) monomer as a 75% aqueous solution, 0.373 g of N,N'-methylenebisacrylamide (BIS) crosslinker, and 0.0325 g of Irgacure®2959 photoinitiator dissolved in 25 ml of a dioxane:dimethylformamide:water mixture, with the solvent volume ratio of 71:12:17, respectively, was prepared. In this solvent mixture, dioxane is a poor solvent while DMF and water are good solvents. A total monomer concentration (APTAC and BIS) of 0.58 mol/L was thus obtained. The crosslinking degree was 20 mol %, based on APTAC. 5 ml of this solution was placed in a glass vial and subjected to UV irradiation at 350 nm for 2 hrs. A white gel was formed which was washed thoroughly with de-ionized water to exchange the reaction solvent and remove the unreacted monomer or soluble oligomers.

The gel formed was mechanically very weak. A sample of the gel was examined using an environmental scanning electron microscope (ESEM) with water vapor present in the sample chamber to prevent drying of the gel. The micrograph, shown in FIG. 1, has dark, cavernous areas that indicate that a macroporous gel was formed.

Example 2

This example illustrates a method of preparing a positively charged composite material of the present invention using the monomer solution of composition described in example 1 applied to a sample of the poly(propylene) porous support PP1545-4. The composite material was prepared according to the general procedure described above using UV irradiation at 350 nm for 2 hours. After polymerization, the composite material was washed with de-ionized water for 48 hrs.

Mass gain of the resulting composite material after drying was 107 wt %, water flux was 1643±5 kg/m² h at 50 kPa and Darcy permeability was 9.53×10⁻¹⁶ m².

Figure 2:
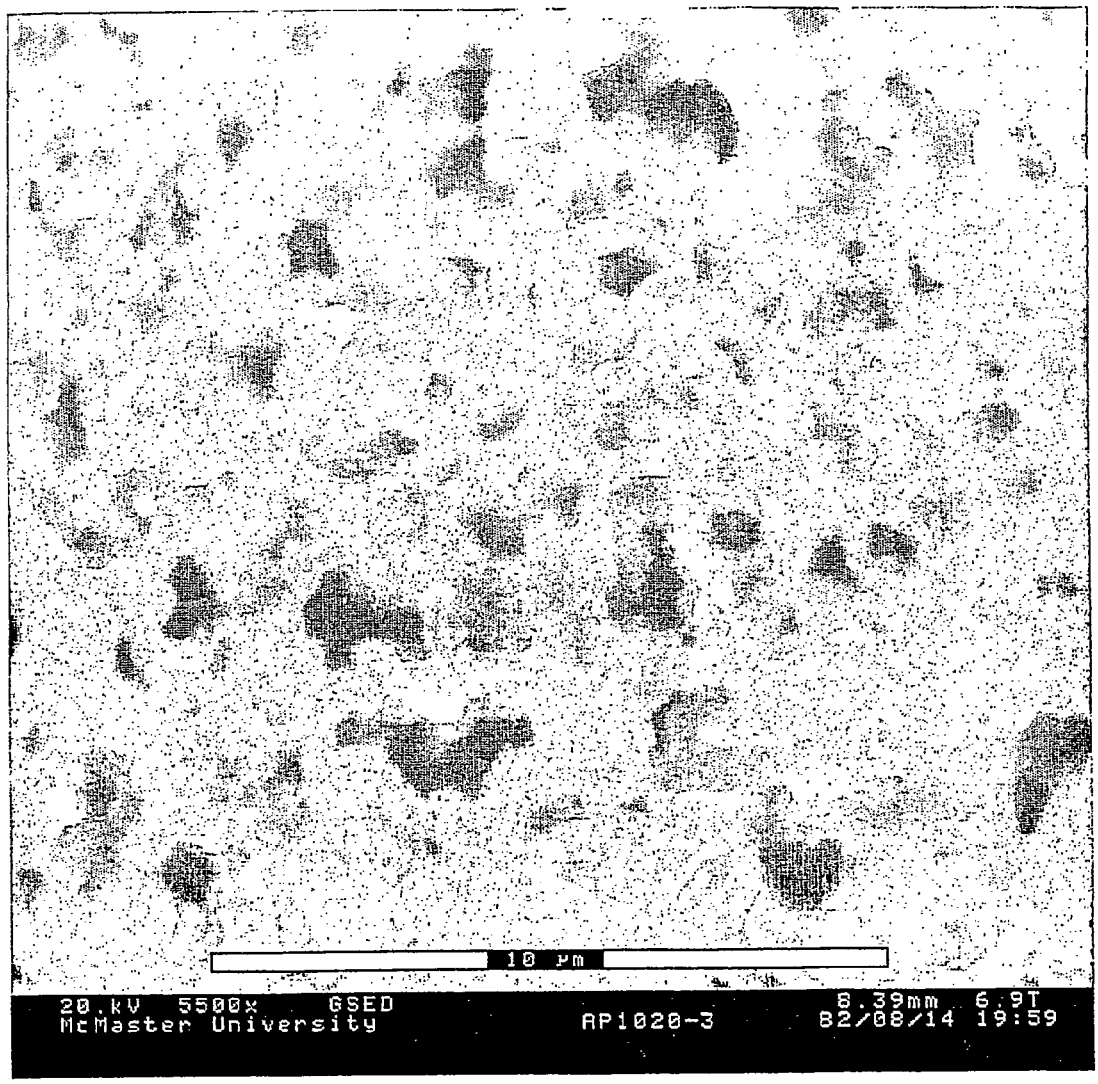
FIG. 2 is an ESEM image of a macroporous poly(APTAC) gel incorporated into a support member in the form of a membrane.

The morphology of the gel-incorporated composite material was examined using ESEM in the same manner as described in Example 1. The ESEM micrograph shown in FIG. 2 shows that the macroporous gel has been incorporated into the host membrane. The micrograph shows a similar structure to that of the unsupported macroporous gel shown in FIG. 1 and little evidence of the microporous support member.

Example 3

This example illustrates a method of preparing a negatively charged composite material of the present invention, with a weak acid functionality.

5.50 g of vacuum-distilled methacrylic acid (MAA) monomer, 0.4925 g of N,N'-methylenebisacrylamide crosslinker and 0.1503 g of Irgacure® 2959 photoinitiator were dissolved in 25 ml of a dioxane:DMF solvent mixture with a volume ratio of 9:1, respectively, to prepare the starting monomer solution. The composite material was prepared using the poly(propylene) PP1545-4 support and the general procedure for the photoinitiated polymerization described above. The irradiation time used was 2 hours and the resulting membrane was washed with DMF for 24 hrs followed by a 48 hr wash with deionized water. The mass gain of the resulting dried membrane was 231 wt %, water flux was 4276±40 kg/m² h at 50 kPa and Darcy permeability was 2.64×10⁻¹⁵ m².

Figure 3:
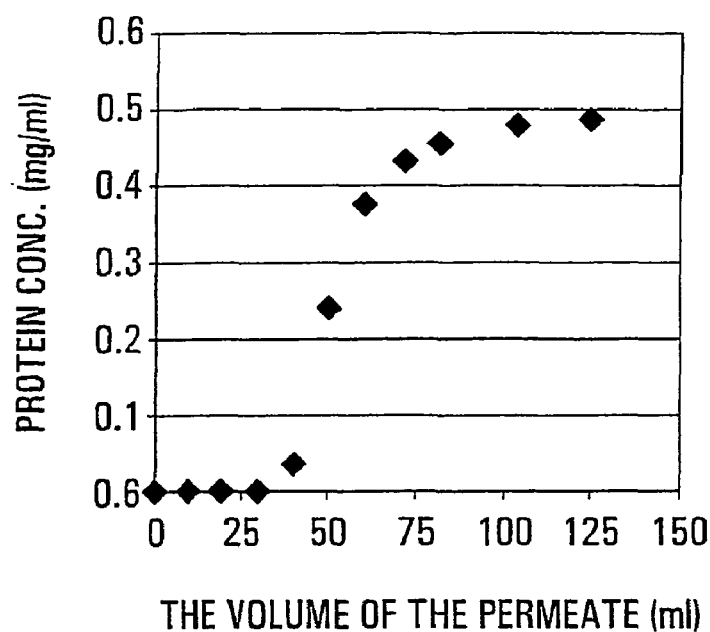
FIG. 3 is a lysozyme adsorption curve of the membrane prepared in Example 3, below. The membrane volume is 0.467 ml.

The protein (lysozyme) absorption/desorption characteristics of the composite material were examined using the general procedure for a single membrane disk outlined earlier. The concentration of the protein used in this experiment was 0.5 g/L in a 10 mM MES buffer at pH 5.5. The flow rate of adsorption experiment was regulated to be 2-4 ml/min. A plot of the concentration of lysozyme in permeate versus the volume of permeate is shown in FIG. 3. It can be seen that even with the single membrane disk, a relatively steep break through curve is obtained indicating a uniform and narrow pore size distribution in the membrane. The composite material has a breakthrough lysozyme binding capacity of 42.8 mg/mL. A desorption experiment with a buffer solution containing 1M NaCl indicated that the recovery of protein was 83.4%.

Example 4

This example illustrates the effect of the total monomer concentration and solvent mixture on the hydraulic flow rate (flux) of composite membranes with weak acid functionality of the type described in Example 3.

A series of composite membranes (MAA1 through MAA5) were prepared using monomer solutions of chemical compositions listed in Table 1 and the porous support PP1545-4. The preparation procedure described in Example 3 was employed.

TABLE 1

The effect of the total monomer concentration and solvent mixture on water flux of composite membranes

| Sample I.D. | Total Monomer Concentration (MAA + BIS) (mol/L) | Crosslinking Degree (mol-%) | Solvent Mixture (volume part) | | Mass Gain (wt %) | Flux at 50 kPa (kg/m² · h) |
|---|---|---|---|---|---|---|
| | | | Dioxane | DMF | | |
| MAA1 | 1.71 | 5 | 8 | 2 | 71 | 12.2 ± 0.1 |
| MAA2 | 2.19 | 5 | 8 | 2 | 153 | 94 ± 14 |
| MAA3 | 2.68 | 5 | 8 | 2 | 177 | 1265 ± 111 |
| MAA4 | 3.66 | 5 | 8 | 2 | 300 | 1800 ± 9 |
| MAA5 | 2.68 | 5 | 9 | 1 | 231 | 4276 ± 40 |

As can be seen from Table 1, the hydraulic flow rate (flux) of composite membranes of the present invention can be tuned by adjusting the monomer loading in the solution contrary to the typical trends found with homogeneous gels, for which an increase in gel density is followed by decrease in permeability, the increase in the mass gain in the membranes of this series results in the flux increase. Further increase in flux is achieved when the concentration of the poor solvent (dioxane) in the solvent mixture is increased (compare samples MAA3 and MAA5).

Example 5

This example illustrates a method of preparing a negatively charged composite material of the present invention that has strong acid functionality.

A solution containing 2.50 g 2-acrylamido-2-methyl-1-propanesulfonic acid (AMPS) monomer, 0.372 g N,N'-methylenebisacrylamide crosslinker and 0.0353 g Irgacure® 2959 photo-initiator, dissolved in 25 ml of a dioxane:H₂O mixture with a volume ratio 9:1, respectively, was used. A composite material was prepared from the solution and the support PP1545-4 using the photoinitiated polymerization according to the general procedure describe above. The irradiation time used was 1 hour at 350 nm. After polymerization, the membrane was extracted with de-ionized water for 48 hrs. The mass gain of the resulting membrane was 74.0 wt %, water flux was 2559±40 kg/m² h at 50 kPa and Darcy permeability was 1.58×10⁻¹⁵ m².

Example 6

This example illustrates further the effect of the solvent mixture composition and the crosslinking degree on the hydraulic flow rate of composite membranes with the strong acid functionality. A series of composite membranes (AMPS1 through AMPS5) was prepared using chemical compositions listed in Table 2 following the general preparation procedure and the irradiation conditions as in example 5.

TABLE 2

The effect of solvent mixture on water flux of the composite membranes

| Sample I.D. | Total Monomer Conc. (mol/L) | Crosslinking Degree (mol %) | Solvent mixture (volume part) | | | Mass gain (wt %) | Flux at 50 kPa (kg/m²h) |
|---|---|---|---|---|---|---|---|
| | | | Dioxane | DMF | H$_2$O | | |
| AMPS1 | 0.48 | 20 | 5 | 5 | 0 | 92 | 3.2 ± 0.0 |
| AMPS2 | 0.48 | 20 | 8 | 2 | 0 | 100 | 575 ± 12 |
| AMPS3* | 0.48 | 20 | 9 | 0 | 1 | 74 | 2559 ± 9 |
| AMPS4 | 0.48 | 10 | 8 | 2 | 0 | 100 | 8.4 ± 0.0 |

AMPS3 is the composite membrane prepared in the previous Example.

As can be seen, a similar pattern to that described in example 4 was observed with regards to the relationship between solubility of polymer in the solvent and water flux of composite membranes comparison of AMPS2 with AMPS 4 shows that hydraulic flow rate (flux) of a composite membrane can also be adjusted by the degree of crosslinking.

Example 7

This example illustrates the effect of introducing a neutral co-monomer into a negatively charged composite material of the present invention.

A solution containing 1.750 g of 2-acrylamido-2-methyl-1-propanesulfonic acid, 0.485 g of acrylamide, 0.868 g of N,N'-methylenebisacrylamide crosslinker, and 0.044 g of Irgacure® 2959 photo-initiator, dissolved in 25 ml of a dioxane:DMF:H$_2$O mixture with a volume ratio 8:1:1, respectively, was prepared. A composite material was prepared from the solution and the support PP1545-4 using the photoinitiated polymerization according to the general procedure describe above. The irradiation time used was 1 hour at 350 nm. After polymerization, the membrane was extracted with de-ionized water for 48 hrs.

The mass gain of the resulting membrane was 103 wt %, water flux was 7132±73 kg/m²·h at 100 kPa, and Darcy permeability was $4.40 \times 10^{-15}$ m².

Example 8

This example illustrates one method of making a positively charged composite material of this invention.

A 15 wt-% solution was prepared by dissolving diallyldimethylammonium chloride (DADMAC) monomer and N,N'-methylenebisacrylamide (BIS) crosslinker in a molar ratio of 5:1, respectively, in a solvent mixture containing 37 wt-% water, 45 wt-% dioxane and 18 wt-% DMF. The photo-initiator Irgacure® 2959 was added in the amount of 1% with respect to the mass of the monomers.

A composite material was prepared from the solution and the support PP1545-4 using the photoinitiated polymerization according to the general procedure describe above. The irradiation time used was 30 minutes at 350 nm. The composite material was removed from between the polyethylene sheets, washed with water and TRIS-buffer solution and stored in water for 24 hrs.

Several samples similar to that described above were prepared and averaged to estimate the mass gain of the composite material. The substrate gained 42.2% of the original weight in this treatment.

The composite material produced by this method had a water flux in the range of 2100-2300 kg/m² hr at 70 kPa and Darcy permeability of $9.87 \times 10^{-16}$ m².

Figure 4:
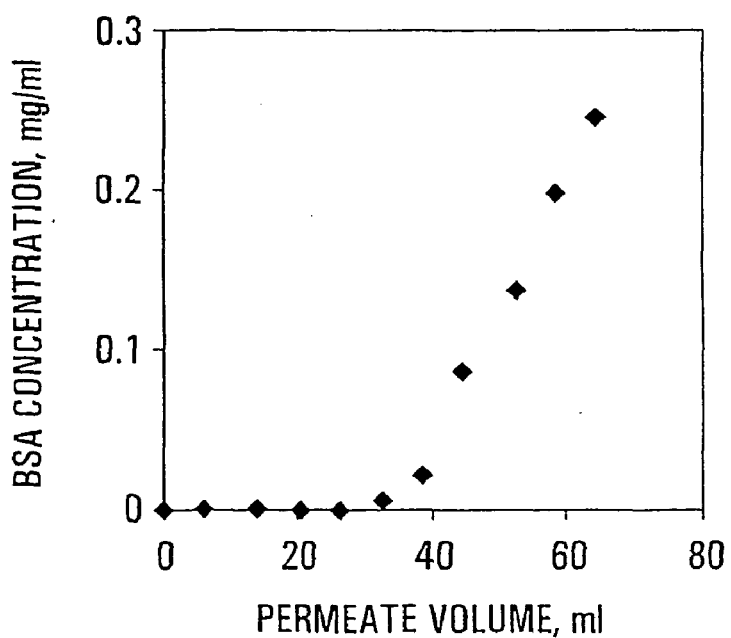
FIG. 4 is a BSA adsorption curve of the membrane prepared in Example 8, below.

The protein (BSA) adsorption characteristic of the composite material was examined using the general procedure for a single membrane disk described above. The concentration of the protein used in this experiment was 0.4 g/L in 50 mM TRIS-buffer. The flow rate was 2-4 ml/min. A plot of the concentration of BSA in the permeate vs. the permeate volume is shown in FIG. 4. The composite material had a BSA binding capacity of 48-51 mg/ml. The BSA desorption was found to be in the range of 78-85%.

Example 9

This example illustrates that by adding a neutral monomer to the charged monomer used in Example 6 the protein binding capacity can be substantially increased.

A 10 wt-% solution was prepared by dissolving diallyldimethylammonium chloride (DADMAC) and acrylamide (AAM), in the ratio 80:20, in a solvent mixture containing 63 wt-% dioxane, 18 wt-% water, 15 wt-% DMF, and 4 wt-% dodecanol. N,N'-methylenebisacrylamide crosslinker was added to the monomer solution to obtain 40% (mol/mol) crosslinking degree. The photoinitiator Irgacure® 2959 was added in the amount of 1% with respect to the total mass of monomers.

A composite material was prepared from the solution and the support PP1545-4 using the photoinitiated polymerization according to the general procedure describe above. The irradiation time used was 20 minutes at 350 nm. The composite material was removed from between the polyethylene sheets, washed with water, TRIS-buffer solution and stored in water for 24 hrs.

A similar sample to that described above was prepared and used to estimate the mass gain of the composite material. The substrate gained 80% of the original weight in this treatment.

The composite material produced by this method had a water flux in the range of 250 kg/m² hr at 70 kPa and Darcy permeability was $1.09 \times 10^{-16}$ m².

The protein (BSA) adsorption characteristic of the composite material was examined using the general procedure for a single membrane disk described above. The protein concentration was 0.4 g/L in a 50 mM TRIS buffer solution. The flow rate of absorption experiment was adjusted to 2-4 ml/min. The composite material had a BSA binding capacity of 104 mg/ml.

Example 10

This example illustrates the formation of a supported porous gel composite material by crosslinking of a preformed polymer.

Three separate solutions were prepared with the following compositions: (A) 20 g of branched poly(ethyleneimine) (BPEI) (25,000 Da) in 50 ml of methanol, (B) 20 g of poly(ethyleneglycol) PEG (~10,000 Da) in 50 ml of methanol, and (C) ethyleneglycol diglycidyl ether (0.324 g) in 5 ml of methanol.

A mixture of the three solutions was prepared consisting of 2 ml of (A), 3 ml of (B), and 5 ml of (C). A portion of this resulting solution was allowed to stand in a vial overnight when a phase separation was observed. Examination of the morphology of the upper clear gel layer indicated that it was macroporous.

The same mixed solution was spread on a sample of poly(propylene) support PP1545-4 using the techniques described in the general procedure. The membrane was sandwiched between two poly(ethyleneterephthalate) sheets and allowed to stand overnight. The composite material was extracted with methanol at room temperature for 24 h, and a mass gain of 95% was observed. The water flux of the composite material was 6194 kg/m$^2$ h at 100 kPa and Darcy permeability was $4.89 \times 10^{-10}$ m$^2$.

The dynamic protein absorption capacity of the composite material was measured using a BSA solution (0.4 mg/mL) in the method for a single membrane disk described in the general section above. It had a capacity of 68 mg/ml before breakthrough.

Example 11

This example illustrates the effect of monomer mixture composition and the polymerization conditions on the hydraulic properties of composite materials prepared by in situ polymerization of glycidyl methacrylate (GMA) with ethylene dimethacrylate (EDMA) used as a crosslinker. The solvents used were dodecanol (DDC), cyclohexanol (CHX), and methanol. A porous polypropylene support membrane PP1545-4 and two modes of initiation of in situ polymerization were used according to the general procedure described above. In the photopolymerization mode, 2,2-dimethoxy-2-phenylacetophenone (DMPA) was used as a photoinitiator while the thermal polymerization was initiated by 1,1'-azobis(cyclohexanecarbonitrile). In both modes, the polymerization was carried out for 2 hours.

The polymerization conditions and properties of the composite materials containing porous poly(glycidyl methacrylate-co-ethylene diacrylate) are presented in Table 3.

Figure 5:
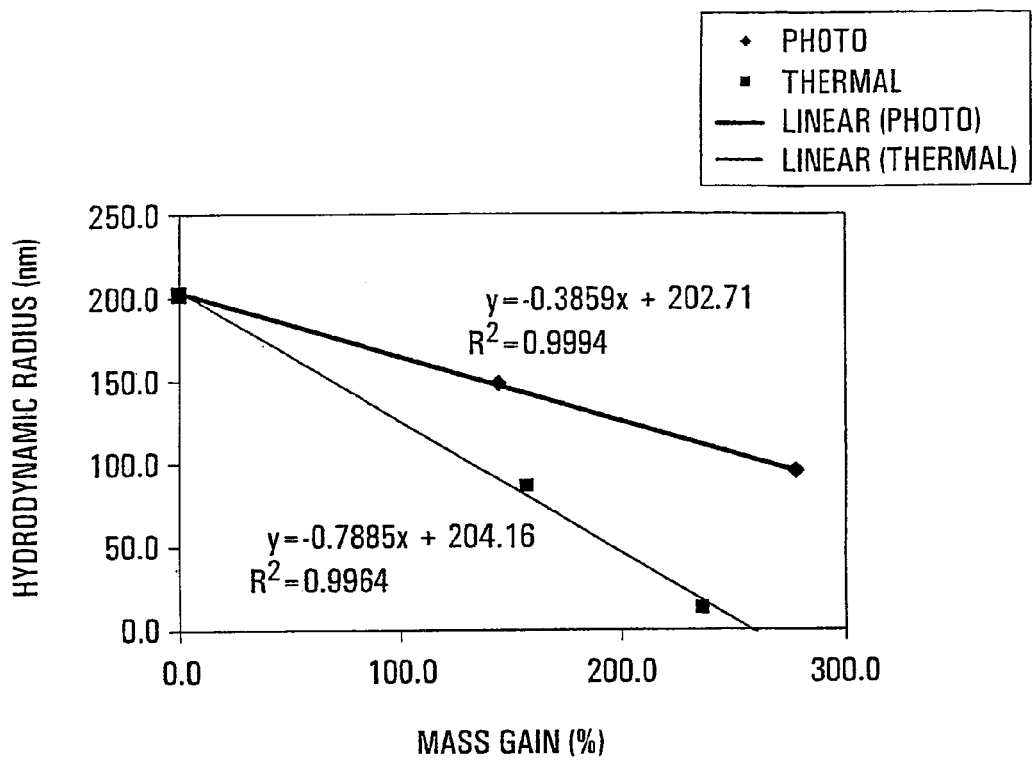
FIG. 5 is a graphical representation of the hydraulic radius as a function of mass gain with photo- and thermally initiated porous gel containing membranes. Gel: poly(glycidyl methacrylate-co-ethylene diacrylate); solvents: dodecanol(DDC)/cyclohexanol(CHX) 9/91.

The high values of the pure water flux measured at 100 kPa of transmembrane pressure (Table 3) indicate that the pore-filling material is macroporous. The pure water flux and, consequently, the hydraulic radius are affected not only by the mass gain but also by the polymerization mode. As shown in FIG. 5, the hydraulic radius is a linear function of the mass gain with the slope depending on the polymerization mode. The absolute value of the negative slope in the thermal polymerization is twice that of the photopolymerized composite materials. This means that photopolymerized composite materials have larger pores than that of the thermally polymerized ones at the same mass gains. Thus, the photo-initiated polymerization, which is faster than the thermally-initiated one, produces larger pores. Since the monomer conversion is practically the same in both cases of polymerization (similar mass gains), the presence of the poly(propylene) substrate either through its hydrophobic nature or by creating microscopic confinements for the polymerization affects the pore formation and the final structure of the pore-filling materials.

By changing the solvents from dodecanol/cyclohexanol 9/91 to methanol, which is cheaper and environmentally more acceptable than the other solvents, a composite material with very high flux was obtained (membrane AM619, Table 3). The composite material was produced from the concentrated monomer mixture and had flux comparable with that of the membrane AM614 which had a mass gain almost twice as low as that of AM619.

This and subsequent examples illustrate a feature of some composite materials of the invention. With the capability to change the composition and concentration of the monomers and solvents, there can be produced stable composite materials with different porous structures. As shown in Table 3, composite materials with larger pores can be made in this way.

Example 12

This example illustrates further the effect of monomer mixture composition on the hydraulic properties of composite materials of this invention.

A series of composite materials have been prepared according to the general procedure described above and containing porous poly(acrylamide) gels formed by in situ photoinitiated polymerization of acrylamide (AAM) and N,N'-methylenebisacrylamide (BIS) as a crosslinker in the pores of

TABLE 3

Porous poly(glycidyl methacrylate-co-ethylene diacrylate)-filled composite materials

| Membrane ID | Total Monomer Concentration wt-% | Solvent | Initiation Mode of Polymerization | Mass Gain wt-% | Darcy Permeability m$^2$ | Hydrodynamic radius nm |
|---|---|---|---|---|---|---|
| AM612 | 43.8 | DDC/CHX 9/91 | Photo | 276.8 | $6.96 \times 10^{-16}$ | 95.1 |
| AM614 | 22.9 | DDC/CHX 9/91 | Photo | 144.3 | $2.77 \times 10^{-15}$ | 148.5 |
| AM615 | 47.6 | DDC/CHX 9/91 | Thermal | 237.0 | $1.66 \times 10^{-17}$ | 13.0 |
| AM616 | 24.9 | DDC/CHX 9/91 | Thermal | 157.5 | $9.15 \times 10^{-16}$ | 86.4 |
| AM619 | 48.6 | Methanol | Photo | 265.0 | $2.48 \times 10^{-15}$ | 163.8 |

The mass gain obtained in this series of composite materials is proportional to the total monomer concentration in the polymerization mixture. Membranes AM612, AM615, and AM619 were prepared using high concentration of monomers while in membranes AM614 and AM616 the monomer concentration was cut approximately by half (Table 3).

a poly(propylene) support membrane. The porous support member used was poly(propylene) TIPS membrane PP1545-4. 2,2-Dimethoxy-2-phenylacetophenone (DMPA) or 1-[4-(2-hydroxyethoxy)phenyl]2-hydroxy-2-methyl-1-propane-1-one (Irgacure® 2959) were used as photoinitiators. Irradiation was carried out at 350 nm for 2 hours. Composition of the pore-filling solutions and the properties of the resulting composite materials are summarized in Table 4.

separated gel covering the member surface with no discernible elements of the support member.

TABLE 4

Composition and properties of poly(acrylamide)-filled composite materials

| Membrane I.D. | Degree of XL Wt-% | Total Monomer Conc. wt-% | Solvent 1 Name | Conc. wt-% | Solvent 2 Name | Conc. wt-% | Mass Gain % | Darcy Permeability $m^2$ | Hydrodynamic Radius nm |
|---|---|---|---|---|---|---|---|---|---|
| AM606 | 18.0 | 13.3 | Water | 86.6 | None | 0.0 | 111.7 | $9.3 \times 10^{-18}$ | 8.0 |
| AM607 | 18.0 | 13.6 | Water | 67.9 | Methanol | 18.4 | 107.8 | $2.5 \times 10^{-18}$ | 4.1 |
| AM608 | 18.0 | 14.4 | Water | 71.8 | Glycerol | 13.7 | 110.4 | $2.1 \times 10^{-18}$ | 3.8 |
| AM609 | 16.8 | 12.0 | Water | 51.9 | Glycerol | 36.0 | 103.3 | $1.6 \times 10^{-18}$ | 3.3 |
| AM610 | 31.8 | 34.5 | DMF | 49.1 | 1-Propanol | 16.4 | 307.2 | $3.9 \times 10^{-17}$ | 20.0 |
| AM611 | 32.0 | 18.7 | DMF | 60.9 | 1-Propanol | 20.5 | 130.3 | $5.3 \times 10^{-16}$ | 62.7 |
| AM617 | 32.2 | 34.9 | DMF | 48.4 | 1-Octanol | 16.7 | 273.3 | $8.6 \times 10^{-17}$ | 29.0 |

Figure 6:
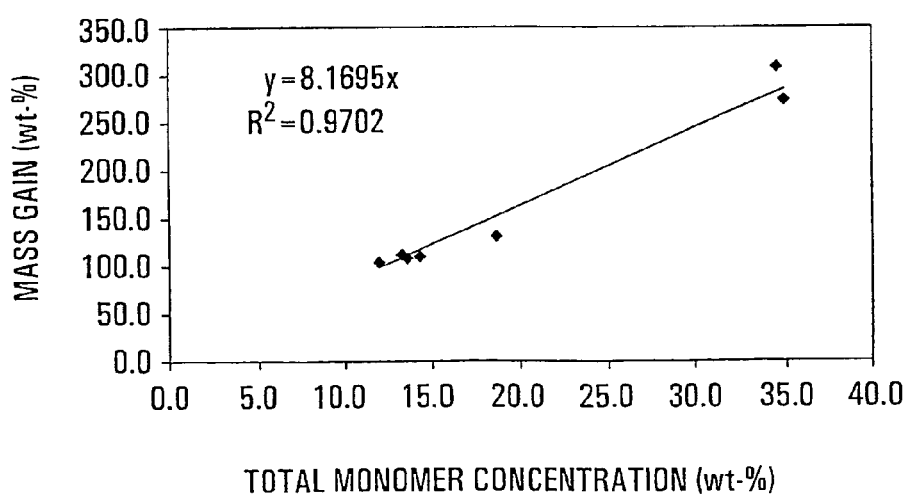
FIG. 6 is a graphical representation of the mass gain as a function of total monomer concentration during the preparation of composite membranes.

Membranes AM606 through AM609 have been prepared using very similar concentration of monomers (12.0-14.4 wt-%) and a similar, relatively high, degree of crosslinking (16.8-18.0 wt-% of monomers). The mass gains obtained with these composite materials are also very similar. As shown in FIG. 6, there is a linear relationship between total monomer concentration in the pore-filling solution and the mass gain achieved after photopolymerization.

The high degree of crosslinking in the composite material prepared from aqueous solution without non-solvent (AM606) leads to relatively high permeability. Surprisingly, the addition of methanol or glycerol, which are poor solvents for linear poly(acrylamide), to water, which is a good solvent for the linear polymer, brings about a substantial reduction in the Darcy permeability and the hydrodynamic radius calculated on its basis. The reduction in permeability is higher with glycerol than with methanol and increases with the amount of glycerol in the solution.

The use of mixtures of poor solvents, such as N,N'-dimethylformamide and 1-propanol or 1-octanol, as well as the further increase of the degree of crosslinking and total monomer concentration have been tested in membranes AM610, AM611, and AM617. As shown in Table 4, substantially higher permeabilities and hydraulic radii are obtained with all these composite materials as compared to the composite materials prepared with water as one of the solvents. This occurred despite an increase of the total monomer concentration; more than double in membranes AM610 and AM617 than that in the membranes prepared with water as one of the solvents. Changing the other solvent from 1-propanol in AM610 to 1-octanol in AM617 also brings about substantial increase in permeability and hydraulic radius.

Figure 7:
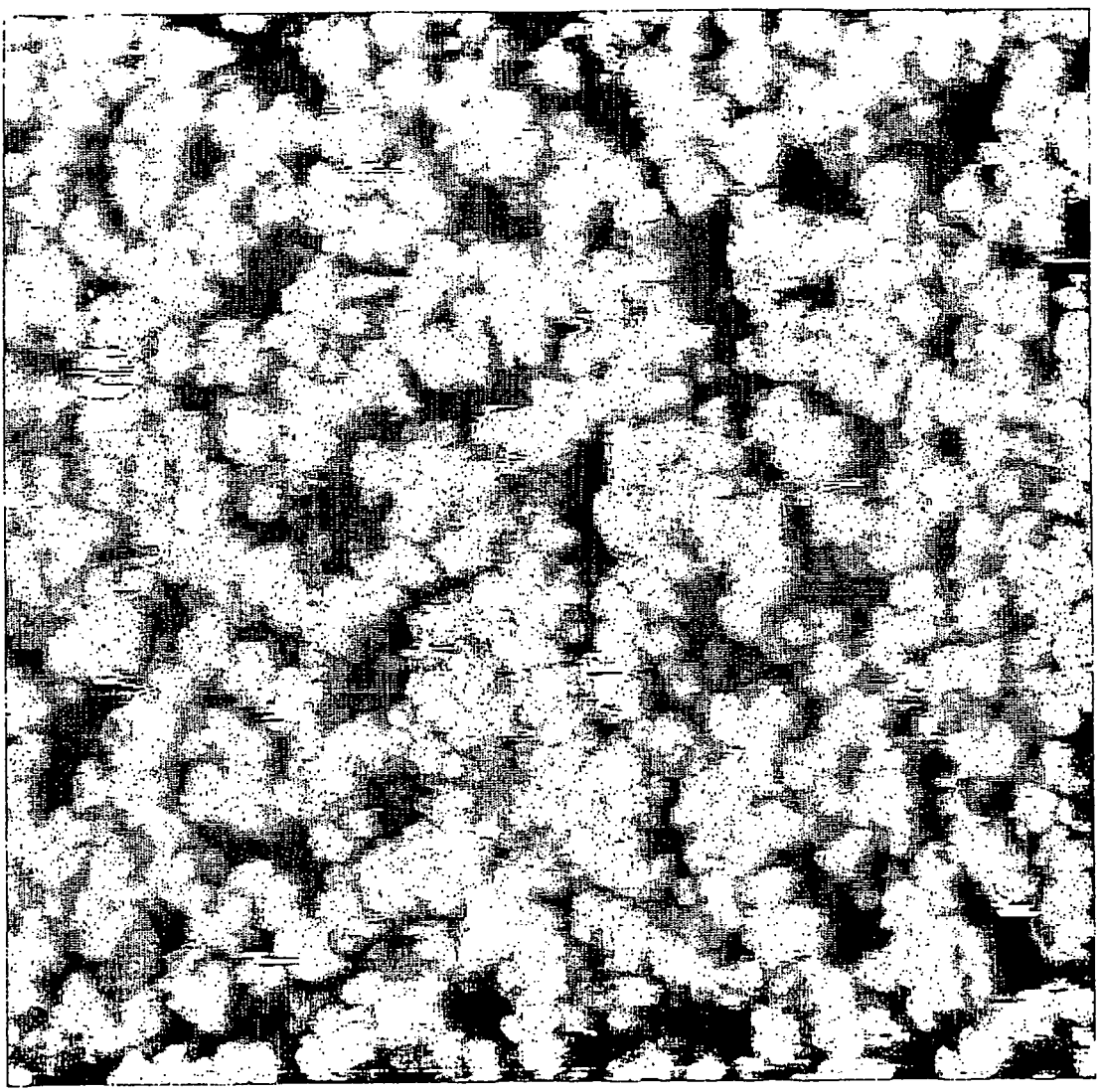
FIG. 7 s an AFM image of the surface of the AM610 membrane; (scanned area: 100 μm$^2$)
Figure 8A:
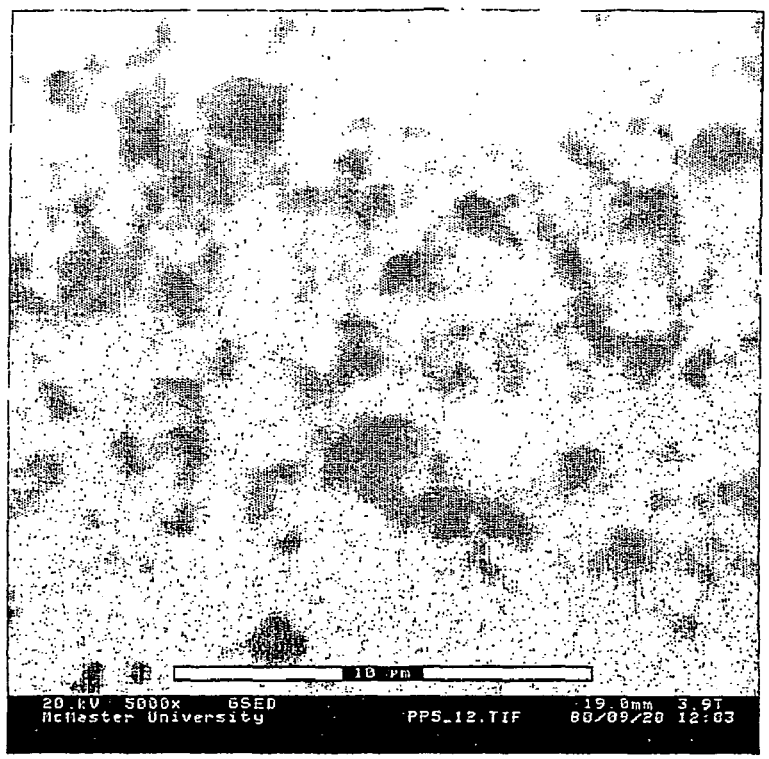
FIG. 8 shows ESEM images of a nascent (top) and AM610 (bottom) surfaces; (magnification: 5000×)
Figure 8B:
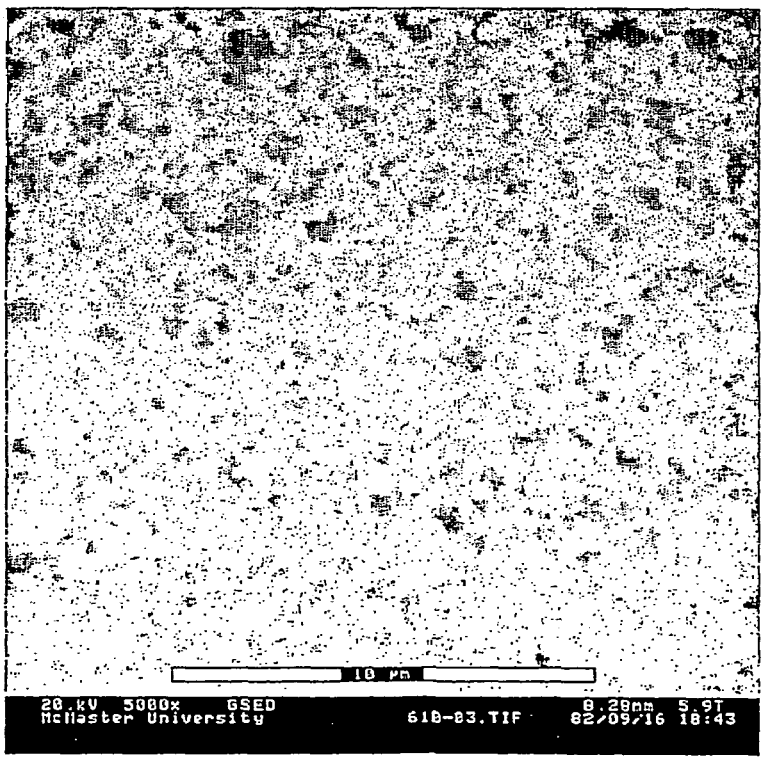

Microscopic images of the surface of membrane AM610 are shown in FIGS. 7 (AFM) and 8 (ESEM). For comparison, an ESEM image of the nascent porous support member is also shown in FIG. 8. Both sets of images show a porous phase-separated gel covering the member surface with no discernible elements of the support member.

Figure 9A:
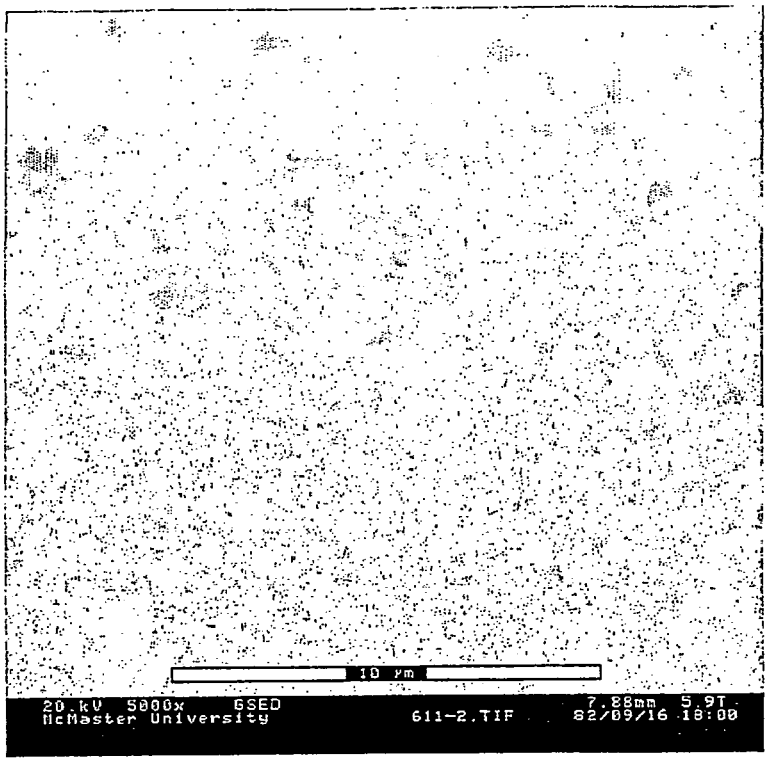
FIG. 9 shows ESEM images of the surface of AM611 membrane; (magnification: top—5000×, bottom—3500×)
Figure 9B:
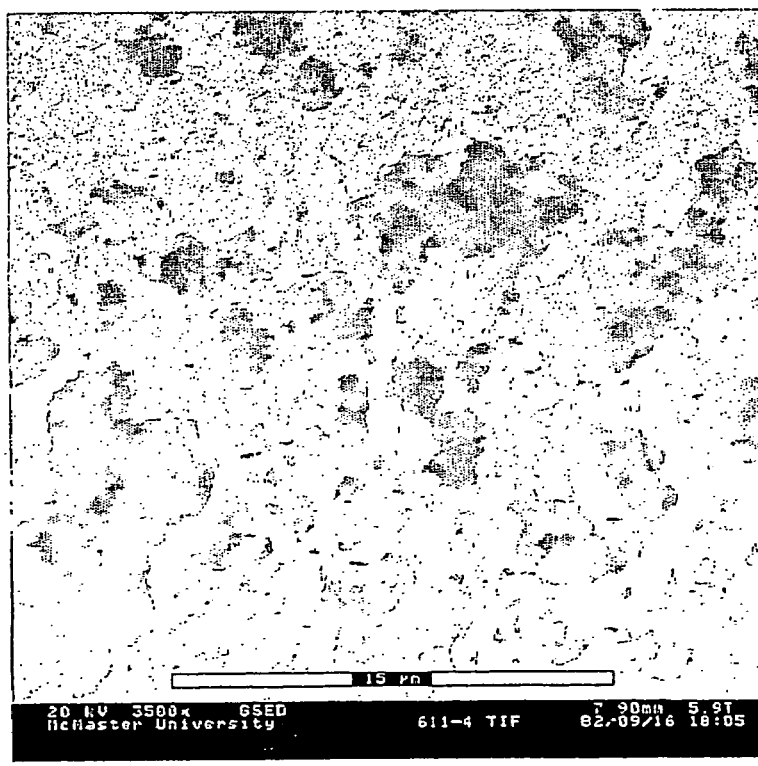

Membrane AM611 was prepared with DMF and 1-propanol but the total monomer concentration was just over half that of AM610. Membrane AM611 shows very high flux and the hydraulic radius three times that of AM610. The ESEM images of the surface of this membrane are presented in FIG. 9. It shows a highly porous gel structure (top image) that resembles the bulk gel formed in some spots on the membrane surface but detached from the membrane (bottom picture).

Figure 10A:
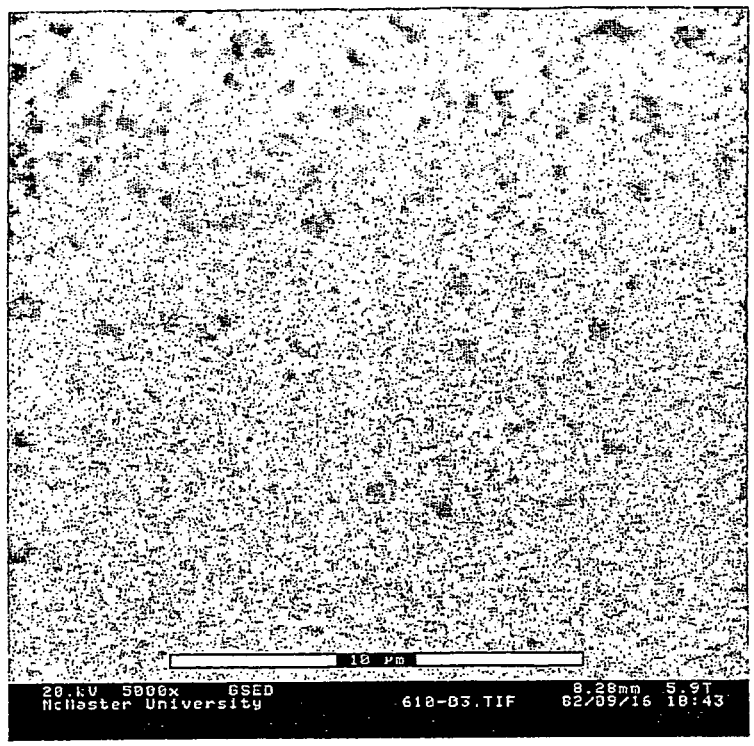
FIG. 10 shows ESEM images of membranes AM610 (top) and AM611 (bottom); (magnification 5000×)
Figure 10B:
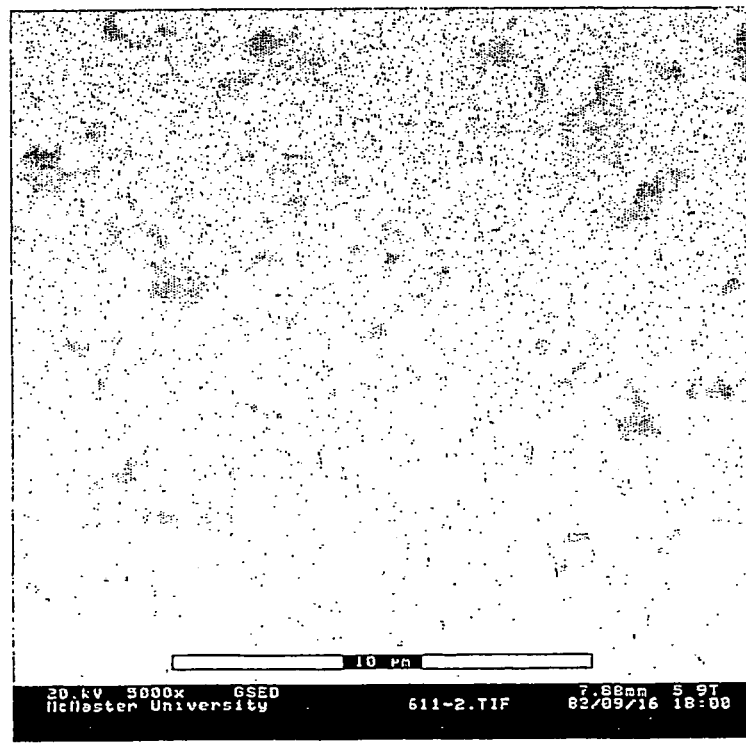

A comparison of surfaces of membranes AM610 and AM611 is presented in FIG. 10. The large difference in the size of the structural elements in these two gels is clearly visible.

The composite materials prepared in this example can serve as ultrafiltration membranes. It has been shown that the pore size of the composite material and, therefore, its separation properties, can be controlled to achieve a wide range of values.

Example 13

This example illustrates the effect of pore size of the support member on the hydraulic flow rate (flux) through composite materials of this invention.

Two polypropylene support membranes of pore size 0.45 µm and 0.9 µm, PP1545-4 and PP1183-3X, respectively, were used to produce composite materials with the same monomer mixture containing 39.4 wt-% of glycidyl methacrylate and 9.2 wt-% of ethylene diacrylate in methanol, thus having 48.6 wt-% of monomers and 18.9 wt-% of ethylene diacrylate (crosslinker) in the monomer mixture. The photoinitiator used was DMPA in the amount of 1.3 wt-% of monomers.

The composite materials were prepared according to the general procedure described above. The irradiation time was 2 hours at 350 nm. The resulting composite materials were washed with methanol followed by deionized water. The composite materials were tested for water flux at 100 kPa to calculate the Darcy permeability and hydraulic radius. The results are presented in Table 5.

TABLE 5

Hydraulic properties of composite membranes produced with substrates of different pore sizes

| Membrane ID | Support pore size (µm) | Mass Gain (wt-%) | Flux at 100 kPa (kg/m²h) | Hydrodynamic radius (nm) | Average hydrodynamic radius (nm) | Standard Deviation (%) |
|---|---|---|---|---|---|---|
| AM619 | 0.45 | 265.0 | 8080.9 | 163.8 | 156.2 | 6.9 |
| AM620 | 0.90 | 296.8 | 7310.1 | 148.5 | | |

The data show that the hydraulic radius in both composite materials is the same within an experimental error, proving that the composite materials contain macroporous gels of similar structure.

Example 14

This Example illustrates the synthesis of poly(ethylene glycol) (PEG, MW's 4000, 2000, 1,000, and 200) diacrylates, which can be used as crosslinkers to prepare the composite material of the invention.

The synthesis procedure used follows that described by N. Ch. Padmavathi, P. R. Chatterji, *Macromolecules*, 1996, 29, 1976, which is incorporated herein by reference. 40 g of PEG 4000 was dissolved in 150 ml of $CH_2Cl_2$ in a 250-ml round bottom flask. 2.02 g of triethylamine and 3.64 g of acryloyl chloride were added dropwise to the flask separately. Initially the reaction temperature was controlled at 0° C. with an ice bath for 3 hrs, and then the reaction was allowed to warm to room temperature and kept for 12 hrs. The reaction mixture was filtered to remove the precipitated triethylamine hydrochloride salt. The filtrate then was poured into an excess of n-hexane. The colorless product, referred to as PEG 4000 diacrylate, was obtained by filtration and drying at room temperature.

The same procedure was used with the PEG's of other molecular weights. The molar ratios of the PEG to acryloyl chloride were kept the same as used above with PEG 4000.

Example 15

This example illustrates a further method of preparing a negatively charged composite material that has a high adsorption capacity for lysozyme.

A solution containing 0.6 g of 2-acrylamido-2-methyl-1-propanesulfonic acid (AMPS), and 0.4 g of acrylamide (AAM) as monomers, 0.25 g of N,N'-methylenebisacrylamide (BIS) and 1.0 g of PEG 4000 diacrylate obtained in Example 14 as crosslinkers, and 0.01 g of Iragure® 2959 as a photoinitiator was prepared in 10 ml of solvent consisting of a 80:10:10 volume ratio of dioxane, dimethylformamide (DMF), and water.

A porous poly(propylene) support member in the form of a membrane (PP1545-4) was used and the composite material was prepared according to the general procedure, with the irradiation carried out at 350 nm for 20 minutes. After polymerization, the composite material was washed thoroughly with de-ionized water for 24 hrs.

Mass gain of the resulting composite material after drying was 113.2 wt %, water flux was 366±22 kg/m$^2$ h at 100 kPa, and Darcy permeability was $2.26 \times 10^{-1}$.

Figure 11:
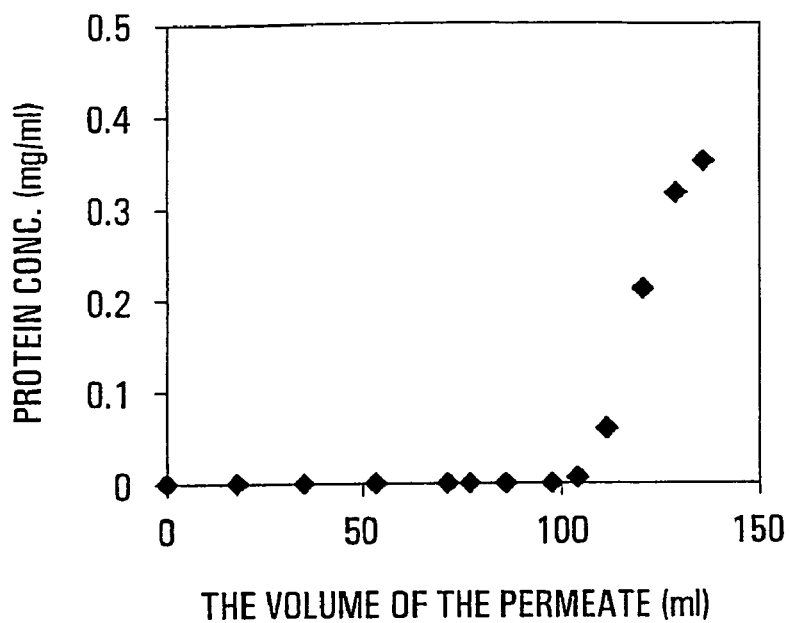
FIG. 11 is a lysozyme adsorption curve of the membrane prepared in Example 15. The membrane volume is 0.501 ml.

The protein (lysozyme) absorption/desorption characteristics of the composite material were examined using the general procedure for a single membrane disk outlined earlier. The concentration of the protein used in this experiment was 0.5 g/L in a 10 mM MES buffer at pH 5.5. The flow rate of adsorption experiment was regulated to be 2-4 ml/min. A plot of the concentration of lysozyme in the permeate versus the volume of permeate is shown in FIG. 11. It can be seen that a relatively steep breakthrough curve is obtained. The composite material had a Lysozyme binding capacity of 103.9 mg/ml. A desorption experiment indicated that the recovery of protein was 64.0%.

Example 16

This example illustrates preparation of a negatively charged composite material with the same nominal polymer composition as in Example 15 but with much higher hydraulic flows (flux) and good lysozyme uptake capacity.

The monomer solution was produced by dilution of the solution formulated in Example 15 with acetone with the mass ratio of 1:1.

A porous poly(propylene) support member in the form of a membrane (PP1545-4) was used and the composite material was prepared according to the general procedure. The irradiation time used was 2 hours. After polymerization, the composite material was washed thoroughly with de-ionized, water for 24 hrs.

The mass gain of the resulting composite material after drying was 51.1 wt % and water flux was 6039±111 kg/m$^2$·h at 100 kPa giving Darcy permeability of $3.73 \times 10^{15}$.

Figure 12:
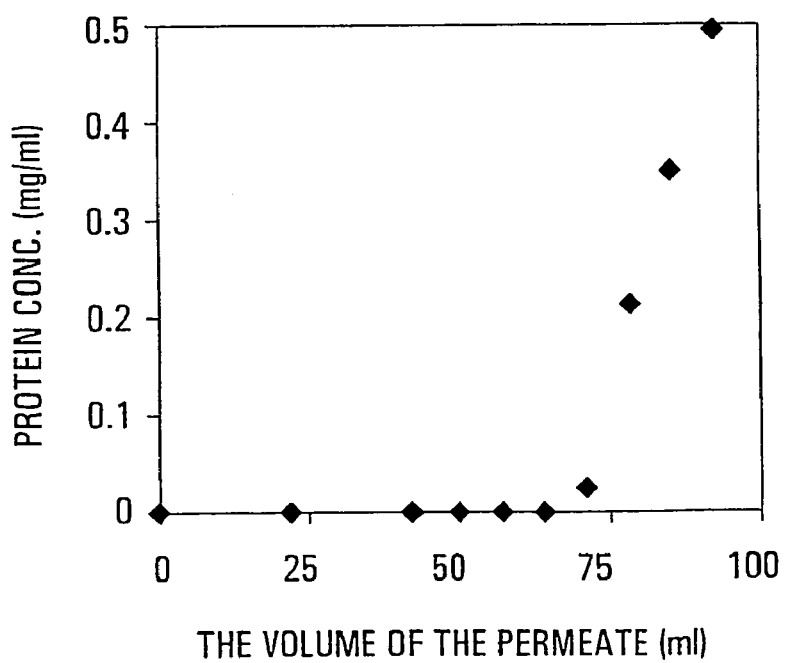
FIG. 12 is a lysozyme adsorption curve of the membrane prepared in Example 16. The membrane volume is 0.470 ml.

The protein (lysozyme) absorption/desorption characteristics of the composite material were examined using the general procedure for a single membrane disk outlined earlier. The concentration of the protein used in this experiment was 0.5 g/L in a 10 mM MES buffer at pH 5.5. The flow rate of adsorption experiment was regulated to be 2-4 ml/min. A plot of the concentration of lysozyme in permeate versus the volume of permeate is shown in FIG. 12. It can be seen that a relatively steep breakthrough curve is obtained. The composite material had a lysozyme binding capacity of 75.4 mg/ml. A desorption experiment indicated that the recovery of protein was 65.0%.

Example 17

This example illustrates a further preparation of a negatively charged composite material that has a very high flux but lower protein binding capacity.

The monomer solution was produced by dilution of the solution formulated in Example 15 with acetone with the mass ratio of 1:2.

A porous poly(propylene) support member in the form of a membrane (PP1545-4) was used and the preparation of composite material was carried out according to the general procedure described above. UV initiated polymerization was carried out for 2 hours. After polymerization, the composite material was washed thoroughly with de-ionized water for 24 hrs.

The mass gain of the resulting composite material after drying was 34.4 wt % and water flux was 12184±305 kg/m$^2$ h at 100 kPa giving Darcy permeability of $7.52 \times 10^{-15}$.

Figure 13:
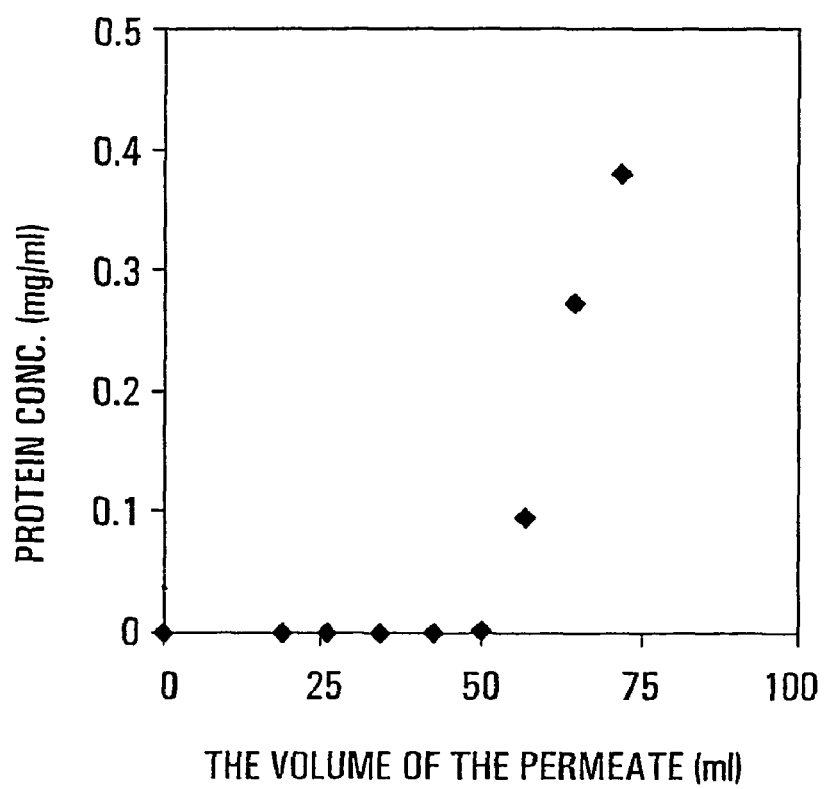
FIG. 13 is a lysozyme adsorption curve of the membrane prepared in Example 17. The membrane volume is 0.470 ml.

The protein (lysozyme) absorption/desorption characteristics of the composite material were examined using the general procedure for a single membrane disk outlined earlier. (The concentration of the protein used in this experiment was 0.5 g/L in a 10 mM MES buffer at pH 5.5. The flow rate of adsorption experiment was regulated to be 2-4 ml/min.) A plot of the concentration of lysozyme in permeate versus the volume of permeate is shown in FIG. 13. It can be seen that a relatively steep breakthrough curve is obtained. The composite material had a lysozyme binding capacity of 53.5 mg/ml. A desorption experiment indicated that the recovery of protein was 99.0%.

Examples 15, 16 and 17 show that it is possible to control the loading of porous gel into the host membrane thereby controlling the water flux at a defined pressure (100 kPa in the data given in the examples) and also that the lysozyme uptake is related to the mass of incorporated porous gel.

Example 18

This example illustrates preparation of a negatively charged membrane that has both good protein adsorption capacity and good flux using a macromonomer.

A monomer solution containing 0.6 g of 2-acrylamido-2-methyl-1-propanesulfonic acid (AMPS), 0.4 g of acrylamide (AAM), 0.25 g of N,N'-methylenebisacrylamide (BIS), 0.01 g of Irgacure® 2959, and 1.0 g of PEG 2000 macromonomer obtained in Example 14, dissolved in 10 ml of a dioxane-(DMF)-water mixture with a volume ratio 80:10:10, respectively, was prepared.

A microporous poly(propylene) support member in the form of a membrane, support PP1545-4, was used together with the general procedure described above. The irradiation time used was 20 minutes. After polymerization, the membrane was washed thoroughly with de-ionized water for 24 hrs.

The mass gain of the resulting membrane after drying was 108.4 wt % and water flux was 1048±4 kg/m² h at 100 kPa giving Darcy permeability of $6.47 \times 10^{-16}$.

The protein (lysozyme) adsorption/desorption characteristics of the membrane were examined using the general procedure for a single membrane disk outlined earlier. A relatively steep break through curve was obtained. The membrane had a lysozyme binding capacity of 88.7 mg/ml. The desorption experiment indicated that the recovery of protein was 64.0%.

Example 19

This example in combination with example 18 above further illustrates that the protein binding capacity and flow characteristics of a membrane can be tuned.

The monomer solution was produced by dilution of the solution formulated in Example 18 with acetone with the mass ratio of 1:1.

A porous poly(propylene) support member in the form of a membrane, support PP1545-4, was used along with the general procedure for the preparation of composite materials described above. The irradiation time used was 90 minutes. After polymerization, the membrane was washed thoroughly with de-ionized water for 24 hrs.

The mass gain of the resulting membrane after drying was 45.7 wt % and water flux was 7319±180 kg/m² h at 100 kPa.

The protein (lysozyme) absorption/desorption characteristics of the membrane were examined using the general procedure for a single membrane disk outlined earlier. A relatively steep break through curve was observed. The membrane had a lysozyme binding capacity of 63.4 mg/ml. The desorption experiment indicated that the recovery of protein was 79.3%.

Example 20

This example illustrates the effect of a neutral co-monomer on the protein binding capacity of composite materials of this invention.

TABLE 6

Chemical composition of stock solutions (amount of monomers in 10 mL of a solution)

| Stock ID | AAM (g) | AMPS (g) | PEG2000XL (g) | BIS (g) | Irgacure® 2959, (g) | Solvents (Dioxane/DMF/H₂O) volumetric ratio |
|---|---|---|---|---|---|---|
| S1 | 0.60 | 0.40 | 1.00 | 0.25 | 0.01 | 8:1:1 |
| S2 | 0.40 | 0.60 | 1.00 | 0.25 | 0.01 | 8:1:1 |

TABLE 6-continued

Chemical composition of stock solutions (amount of monomers in 10 mL of a solution)

| Stock ID | AAM (g) | AMPS (g) | PEG2000XL (g) | BIS (g) | Irgacure® 2959, (g) | Solvents (Dioxane/DMF/H₂O) volumetric ratio |
|---|---|---|---|---|---|---|
| S3 | 0.20 | 0.80 | 1.00 | 0.25 | 0.01 | 8:1:1 |
| S4 | 0 | 1.00 | 1.00 | 0.25 | 0.01 | 8:1:1 |

PEG2000XL: PEG2000 diacrylate prepared in example 14

Monomer solutions were prepared by dilution of stock solutions S1-S4 in Table 6 with acetone with the mass ratio of 1:1.

Composite membranes M1-M4 were prepared by using the corresponding diluted solutions of stocks S1-S4 and following the general preparation procedure described earlier. The porous support used was PP1545-4 and the irradiation time was 90 minutes. Upon completion of polymexization, the composite membranes were washed with de-ionized water for 24 hrs.

The properties and protein binding capacities of composite membranes were examined and the results shown in Table 7. It is evident that the charge density of polyelectrolyte gels influences significantly protein adsorption onto membranes.

TABLE 7

Properties and Lysozyme adsorption capacities of composite membranes

| No. | Flux at 100 kPa (kg/m² · h) | Binding Capacity (mg/ml) |
|---|---|---|
| M1 | 8146 ± 96 | 56.9 |
| M2 | 4273 ± 46 | 76.3 |
| M3 | 7940 ± 303 | 41.5 |
| M4 | 8651 ± 72 | 16.4 |

Example 21

This example illustrates the effect of the chain length of the polyfunctional macromonomers used as crosslinkers (PEG diacrylates) on protein binding capacity of composite materials of this invention.

A series of stock solutions containing 0.6 g of 2-acrylamido-2-methyl-1-propanesulfonic acid (AMPS), 0.4 g of acrylamide (AAM), 0.10 g of N,N'-methylenebisacrylamide (BIS), 0.01 g of Irgacure® 2959, and 1.0 g of PEG diacrylate with different molecular weights (200, 1000, 2000, 4000), obtained in Example 14, dissolved in 10 ml of a dioxane-DMF-water mixture with a volume ratio 80:10:10, respectively, was prepared. The stock solutions were subsequently diluted with acetone at the mass ratio of 1:1. A series of composite membranes were prepared from these solutions using poly(propylene) support PP1545-4 and by following the general preparation procedure described above. The irradiation time used was set to 90 minutes. Upon completion of polymerization, the composite membranes were washed with de-ionized water for 24 hrs.

The properties and protein binding capacities of composite membranes were examined according to the general procedure for a single membrane disk. The results shown in Table 8 clearly indicate that the gel structure of composite membranes has substantial effect on protein adsorption. Possibly, it is related to the gel structure near the macropore surface, where an extremely loose structure may be formed that can allow protein to penetrate into the gel layer at a certain depth. Another possibility is that by using a longer chain PEG diacrylate the surface area is increased owing to some fuzziness at the surface and thus making more adsorption site available to proteins.

TABLE 8

Properties and Lysozyme adsorption capacities of composite membranes

| PEG diacrylate | Flux at 100 kPa (kg/m²h) | Binding Capacity (mg/ml) |
| --- | --- | --- |
| 200 | 8390 ± 218 | 24.4 |
| 1000 | 7275 ± 139 | 58.1 |
| 2000 | 4273 ± 46 | 76.3 |
| 4000 | 6039 ± 111 | 75.4 |

Example 22

This example illustrates the use of fibrous non-woven support to produce a composite material of this invention containing positively charged macroporous gel.

A 10 wt-% solution was prepared by dissolving diallyldimethylammonium chloride (DADMAC) and acrylamide (AAM), which were taken in the ratio 80:20, in a solvent mixture containing 65 wt-% of dioxane, 18 wt-% of water, and 17 wt-% of DMF. N,N'-methylenebisacrylamide (BIS) was added to the monomer solution to obtain 40% (mol/mol) crosslinking degree. The photoinitiator Irgacure® 2959 was added in the amount of 1% with respect to the total mass of the monomers.

A sample of the fibrous non-woven polypropylene substrate TR2611A was placed on a polyethylene sheet and filled with the monomer solution. The substrate was subsequently covered with another polyethylene sheet and the resulting sandwich was run between two rubber rollers to press the monomer solution into the pores and remove excess of solution. The filled substrate was irradiated at 350 nm for 20 min for the polymerization process to occur. The composite material was removed from between the polyethylene sheets, washed with water, TRIS-buffer solution and stored in water for 24 hrs. A duplicate sample was used to estimate the mass gain of the composite material. The substrate gained 45% of the original weight in this treatment.

The composite material produced by this method had a water flux in the range of 2320 kg/m² hr at 70 kPa.

The protein (BSA) adsorption characteristic of a monolayer of the composite material was examined using the general procedures one for a single membrane disk and one for a multi-membrane stack, as described above. The membrane stack contained 7 membrane layers of total thickness 1.75 mm. In both experiments the protein concentration was 0.4 g/L in a 50 mM TRIS buffer solution, and the flow rate of the protein solution used was 3.1±0.1 ml/min, delivered by peristaltic pump. The breakthrough capacity for BSA was 64 mg/ml in the single membrane experiment and 55±2 mg/ml in the multi-membrane stack experiment.

Example 23

This example illustrates the use of a mixture of two monomers in making a positively charged composite material of this invention.

A 10 wt-% solution was prepared by dissolving diallyldimethylammonium chloride (DADMAC) and (3-acrylamidopropyl)trimethylammonium chloride (APTAC), in the ratio 50:50, in a solvent mixture containing 65 wt-% dioxane, 18 wt-% water and 17 wt-% DMF. N,N'-methylenebisacrylamide (BIS) was added to the monomer solution to obtain 40% (mol/mol) crosslinking degree. The photoinitiator Irgacure® 2959 was added in the amount of 1% with respect to the total mass of the monomers.

A sample of the non-woven polypropylene substrate TR2611A was placed on a polyethylene sheet and filled with the monomer solution. The substrate was subsequently covered with another polyethylene sheet and the resulting sandwich was run between two rubber rollers to press the monomer solution into the pores and remove excess of solution. The filled substrate was irradiated at 350 nm for 20 min for the polymerization process to occur. The composite material was removed from between the polyethylene sheets, washed with water, TRIS-buffer solution and stored in water for 24 hrs.

The composite material produced by this method had a water flux in the range of 2550 kg/m² hr at 70 kPa. The mass gain determined with a duplicate sample was found to be 45%.

The protein (BSA) adsorption characteristic of the monolayer composite material was examined using the general procedure for a single membrane disk described above. A solution of BSA concentration of 0.4 g/L in a 50 mM TRIS buffer solution was delivered to the membrane at a flow rate of 2-4 ml/min. The breakthrough capacity of the composite material was 40 mg/ml.

Example 24

This example illustrates the effect of addition of a neutral monomer to the mixture of charged monomers used in example 23.

A 15 wt-% solution was prepared by dissolving diallyldimethylammonium chloride (DADMAC), (3-acrylamido-propyl)trimethylammonium chloride (APTAC), and acrylamide (AAM), which were taken in the ratio 40:40:20, in a solvent mixture containing of 65 wt-% dioxane, 17 wt-% of water, and 18 wt-% of DMF. N,N'-methylenebisacrylamide (BIS) was added to the monomer solution to obtain 20% (mol/mol) crosslinking degree. The photoinitiator Irgacure® 2959 was added in the amount of 1% with respect to the total mass of the monomers.

A sample of the non-woven polypropylene substrate TR2611A was placed on a polyethylene sheet and filled with the monomer solution. The substrate was subsequently covered with another polyethylene sheet and the resulting sandwich was run between two rubber rollers to press the monomer solution into the pores and remove excess of solution. The filled substrate was irradiated at 350 nm for 20 min for the polymerization process to occur. The composite material was removed from between the polyethylene sheets, washed with water, TRIS-buffer solution and stored in water for 24 hrs.

The composite material produced by this method had a water flux of 550 kg/m² hr at 70 kPa and a mass gain (determined using a duplicate samples) of 65 wt-%.

The protein (BSA) adsorption characteristic of the monolayer composite material was examined using the general procedure for a single membrane disk described above. A solution of BSA concentration of 0.4 g/L in a 50 mM TRIS buffer solution was delivered to the membrane at a flow rate of 3.5-4 ml/min. The breakthrough capacity of the composite material was 130 mg/ml.

Example 25

This example illustrates the formation of unsupported positively charged macroporous gel by crosslinking of a preformed polymer.

A 10% solution of poly(allylamine hydrochloride) PAH was prepared by dissolving the polymer in a solvent mixture containing 60% water and 40% iso-propanol (2-propanol). The polymer was partially deprotonated (40%) by adding 6.67 N NaOH. Ethylene glycol diglycidyl ether (EDGE) was added to this solution to obtain 40% (mol/mol) degree of crosslinking. The solution was kept at room temperature for 3 hours for gel formation by the crosslinking reaction between the amine groups of PAH and epoxy groups of EDGE. After 3 hours, the gel was placed in a water bath for all un-reacted chemicals to leach out.

Figure 14:
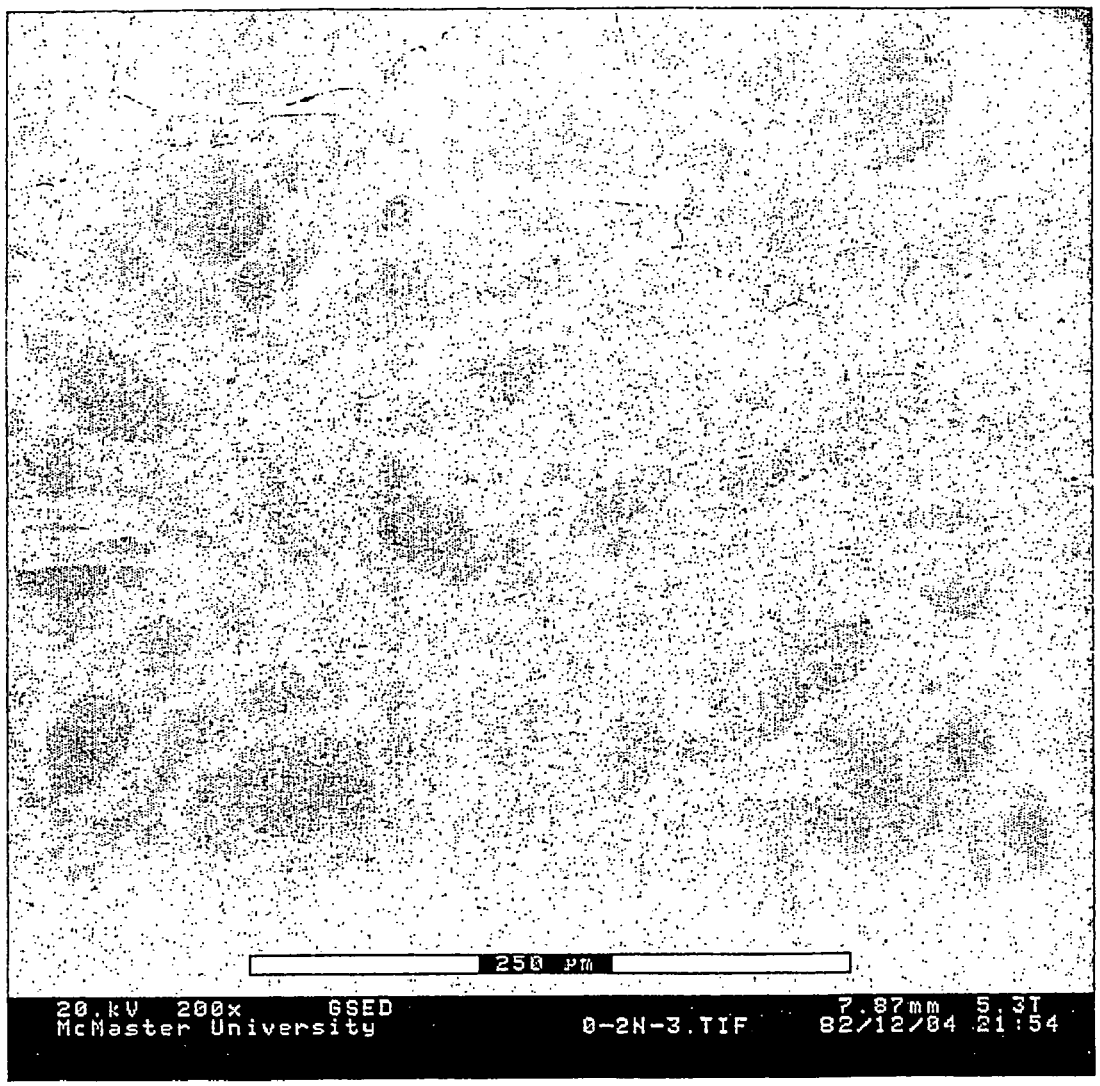
FIG. 14 is an ESEM image of a wet macroporous gel that is the product of Example 25.

A sample of the wet gel was examined using ESEM. The micrograph shown in FIG. 14 indicates that a macroporous gel was formed with the pore diameter of about 70-80 μm. The wet gel was mechanically very weak.

Example 26

This example illustrates the making macroporous gel incorporated in a non-woven fabric support.

A 10 wt-% solution of poly(allylamine hydrochloride) (PAH) was prepared as in Example 25. The polymer was partially deprotonated and EDGE added as described in Example 25 and the solution was applied to a sample of the non-woven polypropylene membrane support TR2611A placed between two polyethylene sheets. The resulting sandwich was run between two rubber rollers to press the polymer solution into the pores of the substrate, spread it evenly, and remove the excess solution. The solution-filled support sample was kept at room temperature for 3 hours for crosslinking process to take place resulting in the formation of gel. After that time, the composite material was removed from the sandwich and placed in a water bath for 12 hours to leach out unreacted chemicals.

Figure 15:
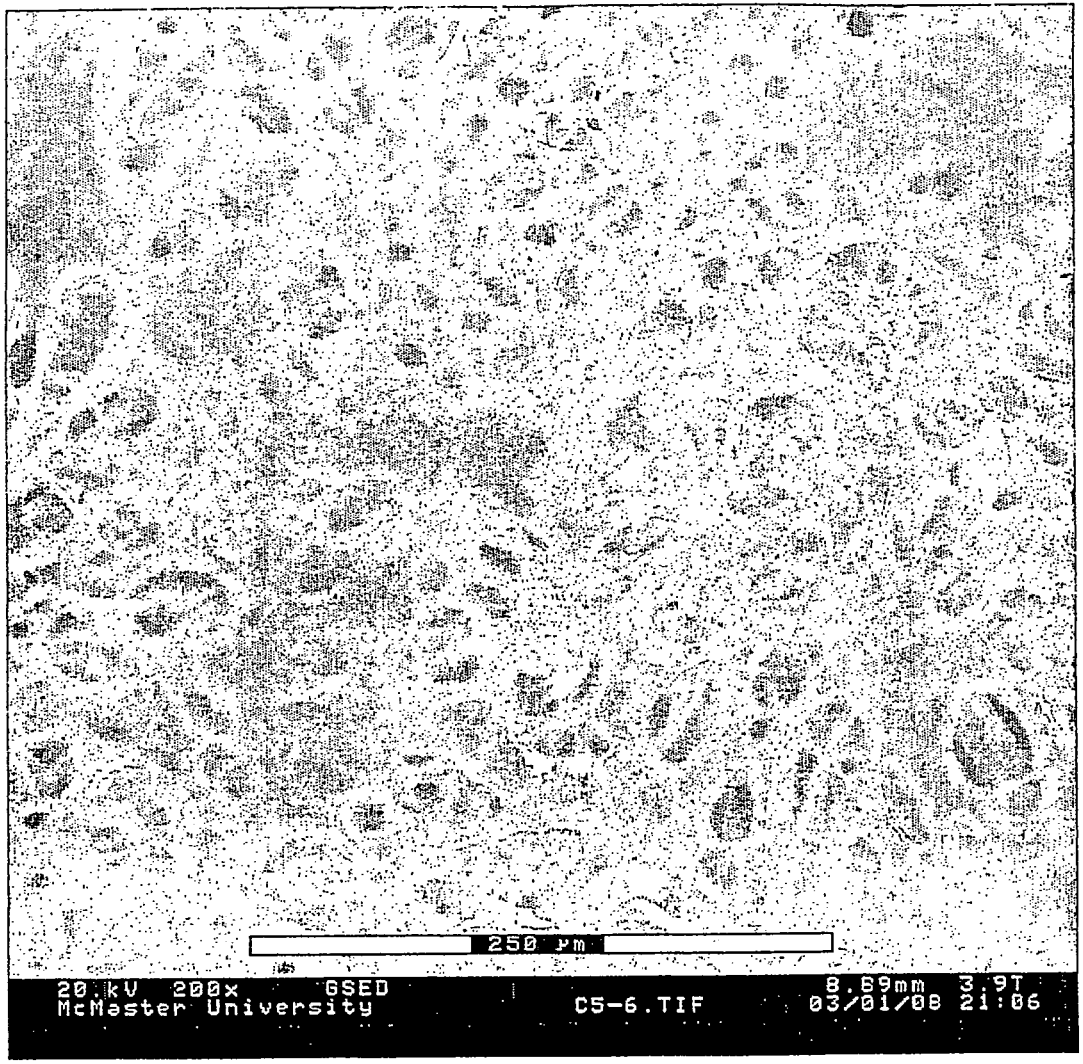
FIG. 15 is an ESEM image of a wet microporous gel in a fibrous non-woven support member that is the product of Example 26.

A wet sample of the resulting composite membrane was examined using ESEM. The micrograph shown in FIG. 15 indicates the composite membrane having macroporous gel in the fibrous non-woven support member. The average pore size of the gel was about 25-30 μm. The membrane thickness was 800 μm and the water flux measured at 100 kPa was 592 kg/m² h. The composite material showed rather low BSA binding capacity of about 10 mg/ml.

Example 27

This example provides a comparison of the protein adsorption by a composite membrane of this invention with the commercial Mustang® Coin Q produced by Pall Corporation.

Figure 16:
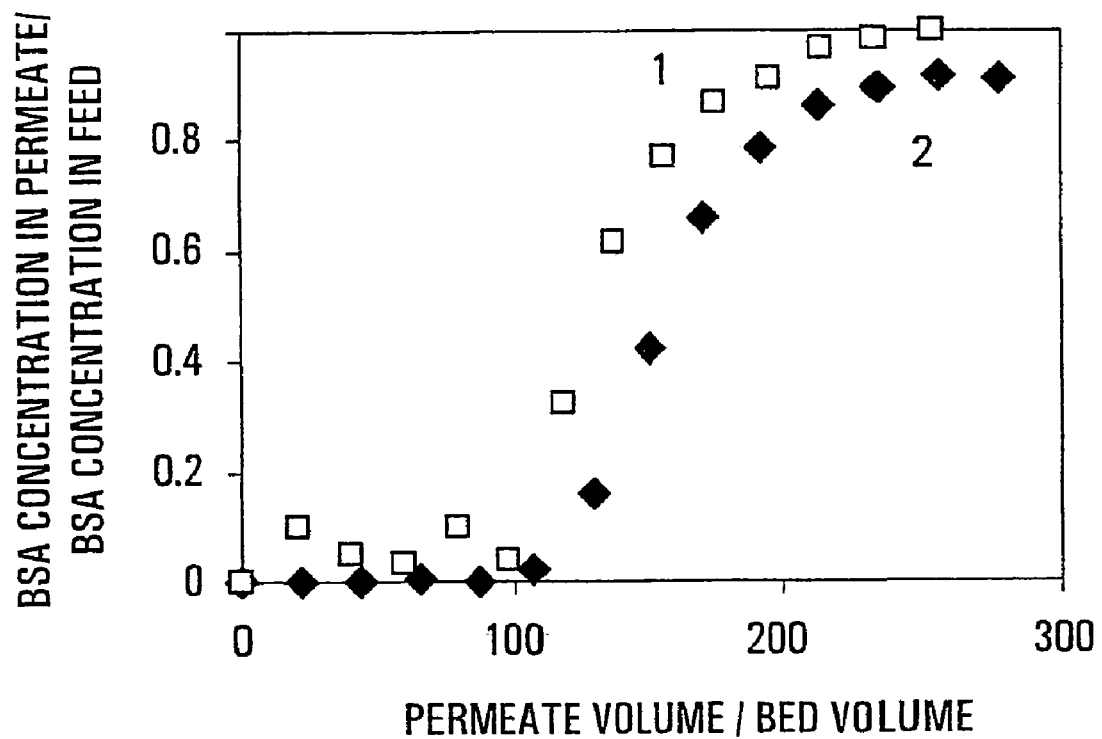
FIG. 16 shows graphically results of using a multi-membrane stack of composite material of Example 22 in a protein (BSA) adsorption test.

A composite material prepared in example 22 was tested in a multi-membrane stack of 7 membrane layers of a total thickness of 1.75 mm, according to the testing protocol described in example 22. A Mustang® Coin Q was also tested under similar conditions. The membrane stack was prepared by placing seven (7) layers of the membrane sample in the wet state on top of each other. The assembled membrane stack was lightly compressed pressed to remove excess of water. The membrane stack was then heated in an oven at 60-70° C. for at least 30 min. The thickness of the resulting membrane stack in the dry state was 1.8-1.9 mm. This process produced a stack in which the multiple membrane layers adhered to each other. The results shown in FIG. 16 indicate that both systems give similar performances.

Example 28

This example provides the hydrodynamic (Darcy) permeability of reference composite materials containing porous support member and homogeneous gels filling the pores of the support. The homogeneous gels were obtained by using thermodynamically good solvents and their homogeneity was assessed based on transparency of simultaneously formed unsupported gels of the same composition. Clear and transparent gels were assumed to be homogeneous, contrary to macroporous gels that were always found opaque.

(A) Glycidyl Methacrylate Based Homogeneous Gel-Filled Composites

The composite materials containing homogeneous gels of glycidyl methacrylate-co-ethylene glycol-dimethacrylate, GMA-co-EDMA, were prepared using 1,4-dioxane as a solvent and 4.7 wt-% of EDMA (crosslinker) in monomer mixture, and different total monomer concentrations. Poly(propylene) support PP1545-4 and the general procedure for preparing the composite materials of this invention were used. DMPA was used as photoinitiator and the irradiation was carried out at 350 nm for 120 minutes. The hydrodynamic permeability of the membranes was measured and an empirical equation was derived for the relationship between the hydrodynamic permeability, k, and the mass gain of the composite membranes containing poly(GMA-co-EDMA) homogeneous gels in the PP1545-4 support. The equation is as follows:

$$k = 3.62 \times 10^3 \times G^{-9.09}$$

The differences between the measured values of permeability and that calculated from the above equation were found to be less than ±3%. This empirical relationship was subsequently used to calculate permeability of reference composite materials at different mass gains.

(B) Poly(diallyldimethylammonium chloride) Based Homogeneous Gel-Filled Composites The composite materials containing homogeneous gels of diallyldimethylammonium chloride-co-methylenebisacrylamide, DADMAC-co-BIS, were prepared using water as a solvent and 1.0 wt-% of BIS crosslinker in monomer mixture, and different total monomer concentrations. Poly(propylene) support PP1545-4 was coated with Triton X-114 surfactant by immersing the support samples in 2 t-% solution of the surfactant in methanol/water (60/40) mixture for 16 hours followed by drying in air. The general procedure for preparing the composite materials of this invention was used to make homogeneous gel-filled membranes. Irgacure® 2959 was used as photoinitiator and the irradiation was carried out at 350 nm for 30-40 minutes. The hydrodynamic permeability of the series of membranes was measured and an empirical equation was derived for the relationship between the Darcy permeability, k, and the mass gain, G:

$$k = 2.09 \times 10^{-12} \times G^{-4.01}$$

(C) Acrylamide Based Homogeneous Gel-Filled Composites

The hydrodynamic permeability of homogeneous poly (acrylamide)-co-methylenebisacrylamide, AAM-co-BIS, was estimated from the empirical relationship between the gel permeability and the gel polymer volume fraction provided by Kapur et al. in Ind. Eng. Chem. Res., vol. 35 (1996) pp. 3179-3185. According to this equation, the hydrodynamic permeability of a poly(acrylamide) gel, $k_{gel} = 4.35 \times 10^{-22} \times \phi^{-3.34}$, where $\phi$ is the polymer volume fraction in the gel. In the same article, Kapur et al. provide a relationship between the hydrodynamic permeability of a gel and a porous membrane filled with the same gel. According to this relationship, the permeability of the membrane, $k_{membrane}=(\delta/\tau) \times k_{gel}$, where $\epsilon$ is the porosity of the support and $\tau$ is the tortuosity of the support pores. The pore tortuosity can be estimated as a ratio of the Kozeny constant, K, for a given porosity, i.e., K=5, and the Kozeny constant for a straight cylindrical capillary equal to 2. Thus, for the poly(propylene) support PP1545-4 with porosity of 0.85, the ratio $(\epsilon/\tau)=0.85/2.5=0.34$.

The polymer volume fraction, $\phi$, can be converted to mass gain using the partial specific volume, $v_2$, for poly(acrylamide) and the density, $\rho$, of poly(propylene). The values of these parameters can be found in Polymer Handbook, edited by Brandrup et al., Chapter VII, Wiley and Sons, New York, 1999. Thus, the mass gain of a composite material containing poly(propylene) support of porosity $\epsilon$ filled with a gel whose polymer occupies the fraction $\phi$ of the pores is given by $$\text{Mass Gain (\%)} = \frac{\phi/v_2}{(1-\varepsilon)\rho} \times 100\%$$

The above equation was combined with that of Kapur et al. to give an empirical relationship allowing one to calculate hydrodynamic-permeability of reference composite materials, k, at different mass gains, G. The combined equation is as follows:

$$k=180\times10^{-12} \times G^{-3.34}$$

The equation is valid for $\rho=0.91$ g/cm$^3$; $\epsilon=0.85$; $v_2=0.7$ cm$^3$/g; $(\epsilon/\tau)=0.34$.

(D) Poly(AMPS) Based Homogeneous Gel-Filled Composites

The composite materials containing homogeneous gels of 2-acrylamido-2-propane-1-sulfonic acid-co-methylenebisacrylamide, AMPS-co-BIS, were prepared using water as a solvent and 10.0 wt-% of BIS crosslinker in monomer mixture, and different total monomer concentrations. Poly(propylene) support PP1545-4 was coated with Triton X-114 surfactant by immersing the support samples in 2 t-% solution of the surfactant in methanol/water (60/40) mixture for 16 hours followed by drying in air. The general procedure for preparing the composite materials of this invention was used to make homogeneous gel-filled membranes. Irgacure® 2959 was used as photoinitiator and the irradiation was carried out at 350 nm for 60 minutes. The hydrodynamic permeability of the series of membranes was measured and an empirical equation was derived for the relationship between the Darcy permeability, k, and the mass gain, G:

$$k=2.23\times10^{-16} \times G^{-1.38}$$

(E) Poly(APTAC) Based Homogeneous Gel-Filled Composites

The composite materials containing homogeneous gels of (3-acrylamidopropane)trimethylammonium chloride-co-methylenebisacrylamide, APTAC-co-BIS, were prepared using water as a solvent and 10.0 wt-% of PIS crosslinker in monomer mixture, and different total monomer concentrations. Poly(propylene) support PP1545-4 was coated with Triton X-114 surfactant by immersing the support samples in 2 t-% solution of the surfactant in methanol/water (60/40) mixture for 16 hours followed by drying in air. The general procedure for preparing the composite materials of this invention was used to make homogeneous gel-filled membranes. Irgacure® 2959 was used as photoinitiator and the irradiation was carried out at 350 nm for 60 minutes. The hydrodynamic permeability of the series of membranes was measured and an empirical equation was derived for the relationship between the Darcy permeability, k, and the mass gain, G:

$$k=9.51\times10^{-16} \times G^{-1.73}$$

(F) Poly(ethyleneimine) Based Homogeneous Gel-Filled Composites

The composite materials containing homogeneous gels of branched poly(ethyleneimine) crosslinked with ethylene glycol diglycidyl ether (EDGE) were prepared using methanol solutions of BPEI of different concentrations. The degree of crosslinking used was 10 mol-%. Poly(propylene) support PP1545-4 was used together with the general procedure of fabrication of composite materials by in situ crosslinking of crosslinkable polymers described in Example 10. A series of membranes with different mass gains was prepared by changing the concentration of PEI in the solution. The Darcy permeability of the membranes was measured and an empirical equation describing the relationship between the permeability, k, and the mass gain, G, was derived. The equation is as follows:

$$k=4.38\times10^{-14} \times G^{-2.49}$$

Example 29

This example provides comparison between Darcy permeability of composite materials of this invention containing supported macroporous gels and the permeability of the reference composite materials containing homogeneous gels filling the porous support member used in this invention.

The comparison is shown in Table 9 below.

TABLE 9

Permeability Ratio Values for Composite Materials

| | Composite Materials containing Macroporous Gels of this Invention | | Darcy Permeability of Reference | |
|---|---|---|---|---|
| Example No. | Mass Gain % | Darcy Permeability $k_{macroporous}$ m$^2$ | Composite Material $k_{homogeneous}$ m$^2$ | Permeability Ratio $k_{macroporous}/k_{homogeneous}$ |
| 2 | 107 | 9.53 × 10$^{-16}$ | 2.93 × 10$^{-19}$ | 3.2 × 10$^3$ |
| 5 | 74 | 1.58 × 10$^{-15}$ | 2.49 × 10$^{-18}$ | 6.3 × 10$^2$ |
| 6 | 92* | 1.98 × 10$^{-18*}$ | 1.85 × 10$^{-18*}$ | 1.1 × 10$^{0*}$ |
| | 100 | 3.53 × 10$^{-16}$ | 1.65 × 10$^{-18}$ | 2.2 × 10$^2$ |
| | 100* | 5.19 × 10$^{-18*}$ | 1.65 × 10$^{-18*}$ | 3.2 × 10$^{0*}$ |
| 7 | 103 | 4.4 × 10$^{-15}$ | 1.58 × 10$^{-18}$ | 2.8 × 10$^3$ |
| 8 | 42 | 9.87 × 10$^{-16}$ | 8.81 × 10$^{-19}$ | 1.1 × 10$^3$ |
| 9 | 80 | 1.09 × 10$^{-16}$ | 6.78 × 10$^{-20}$ | 1.6 × 10$^3$ |
| 10 | 95 | 1.89 × 10$^{-15}$ | 5.40 × 10$^{-19}$ | 3.5 × 10$^3$ |
| 11 | 144 | 2.77 × 10$^{-15}$ | 8.39 × 10$^{-19}$ | 3.3 × 10$^3$ |
| | 158 | 9.15 × 10$^{-16}$ | 3.77 × 10$^{-17}$ | 2.4 × 10$^1$ |
| | 237 | 1.66 × 10$^{-17}$ | 9.20 × 10$^{-19}$ | 1.8 × 10$^1$ |
| | 265 | 2.48 × 10$^{-15}$ | 3.34 × 10$^{-19}$ | 7.5 × 10$^3$ |
| | 277 | 6.96 × 10$^{-16}$ | 2.24 × 10$^{-19}$ | 3.1 × 10$^3$ |
| 12 | 103 | 1.59 × 10$^{-18*}$ | 3.38 × 10$^{-19*}$ | 4.7 × 10$^{0*}$ |
| | 108 | 2.52 × 10$^{-18*}$ | 2.93 × 10$^{-19*}$ | 8.6 × 10$^{0*}$ |
| | 110 | 2.11 × 10$^{-18*}$ | 2.70 × 10$^{-19*}$ | 7.8 × 10$^{0*}$ |
| | 112 | 9.32 × 10$^{-18}$ | 2.61 × 10$^{-19}$ | 3.6 × 10$^1$ |
| | 130 | 5.34 × 10$^{-16}$ | 1.56 × 10$^{-19}$ | 3.4 × 10$^3$ |

*denotes homogeneous or micro-heterogeneous gels in composite materials (Comparative)

TABLE 9-continued

|    |     |                        |                        |                     |
|----|-----|------------------------|------------------------|---------------------|
|    | 273 | $8.57 \times 10^{-17}$ | $1.31 \times 10^{-20}$ | $6.5 \times 10^{3}$ |
|    | 307 | $3.88 \times 10^{-17}$ | $8.87 \times 10^{-21}$ | $4.4 \times 10^{3}$ |
| 15 | 113 | $2.26 \times 10^{-16}$ | $1.39 \times 10^{-18}$ | $1.6 \times 10^{2}$ |
| 16 | 51  | $3.73 \times 10^{-15}$ | $4.16 \times 10^{-18}$ | $9.0 \times 10^{2}$ |
| 17 | 34  | $7.52 \times 10^{-15}$ | $7.18 \times 10^{-18}$ | $1.0 \times 10^{3}$ |
| 18 | 108 | $6.47 \times 10^{-16}$ | $1.47 \times 10^{-18}$ | $4.4 \times 10^{2}$ |
| 19 | 46  | $4.52 \times 10^{-15}$ | $4.85 \times 10^{-18}$ | $9.3 \times 10^{2}$ |

*denotes homogeneous or micro-heterogeneous gels in composite materials.

Examples 30-37

These Examples illustrate a method of preparing a responsive composite material of the present invention using photoinitiated free radical polymerization of acrylic acid (AA) (ionic monomer), acrylamide (AA), and trimethylolpropane triacrylate (TRIM) as a crosslinker. The molar ratio of acrylic acid to acrylamide was 1:1 and 1,4-dioxane was used as a solvent in all experiments. Monomer solution compositions and polymerization conditions are given in Table 10. After polymerization, the responsive composite material was washed with de-ionized water for about 16 hrs.

TABLE 10

Monomer solution compositions and polymerization conditions

| Example no. | Sample ID | Support Member | Total Concentration of Monomer Mixture (wt-%) | Degree of Crosslinking (mol-%) | Irradiation Time (min) | Mass Gain (%) |
|---|---|---|---|---|---|---|
| 30 | AM675 | TR2611A | 19.9 | 5.0 | 20 | 115.6 |
| 31 | AM678 | TR2611A | 13.3 | 5.0 | 90 | 81.7 |
| 32 | AM680 | TR2611A | 12.8 | 5.2 | 20 | 82.3 |
| 33 | AM681 | TR2611A | 12.6 | 10.8 | 15 | 88.8 |
| 34 | AM682 | TR2611A | 23.8 | 10.9 | 15 | 167.3 |
| 35 | AM684 | TR2611A | 31.0 | 10.8 | 10 | 217.3 |
| 36 | AM683 | TR2611A | 38.8 | 10.8 | 15 | 294.6 |
| 37 | AM694 | PP 1545-4 | 24.0 | 10.2 | 10 | 218.0 |

Figure 17:
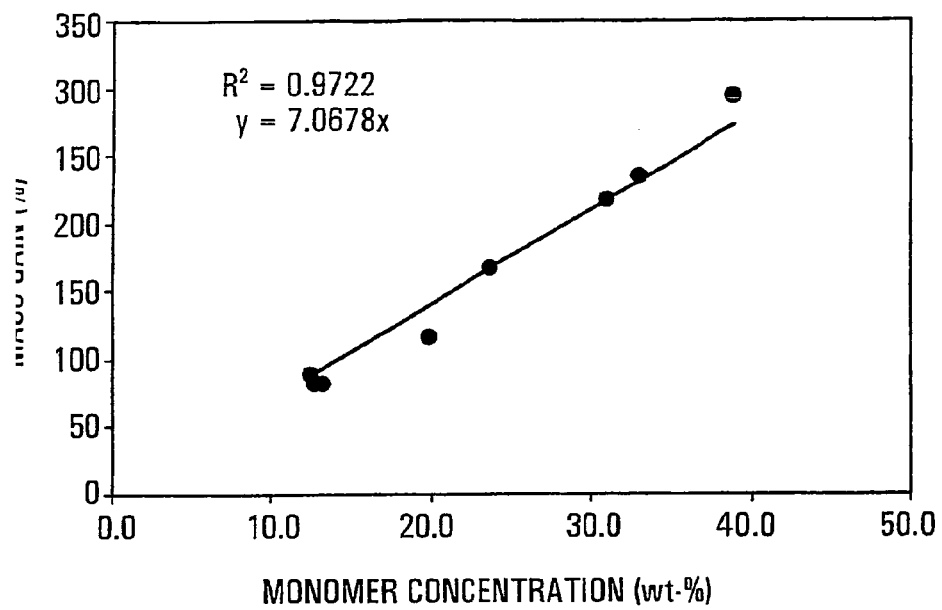
FIG. 17 graphically displays the effect of monomer concentration on the mass gain of composite materials.

The amount of gel formed in the support member depends on the pore volume available to fill, the total concentration of the monomer mixture, and the degree of conversion in the polymerization. In FIG. 17, the mass gain obtained with support TR2611A is plotted as a function of total monomer concentration. The data can be approximated to fall within a straight line ($R^2=0.97$), indicating a similar degree of conversion for each sample. The experimental values are very close to their theoretical counterparts estimated from the pore volume in the support and the monomer concentration. This suggests that the degree of conversion is close to 100% and that an irradiation time of 10 minutes is sufficient under the light conditions applied. As expected, the mass gain obtained with the PP 1545-4 support was higher than that obtained with the TR2611A support due to the larger porosity of the former (85 vol-t versus 79.5 vol-%).

Example 38

Figure 18:
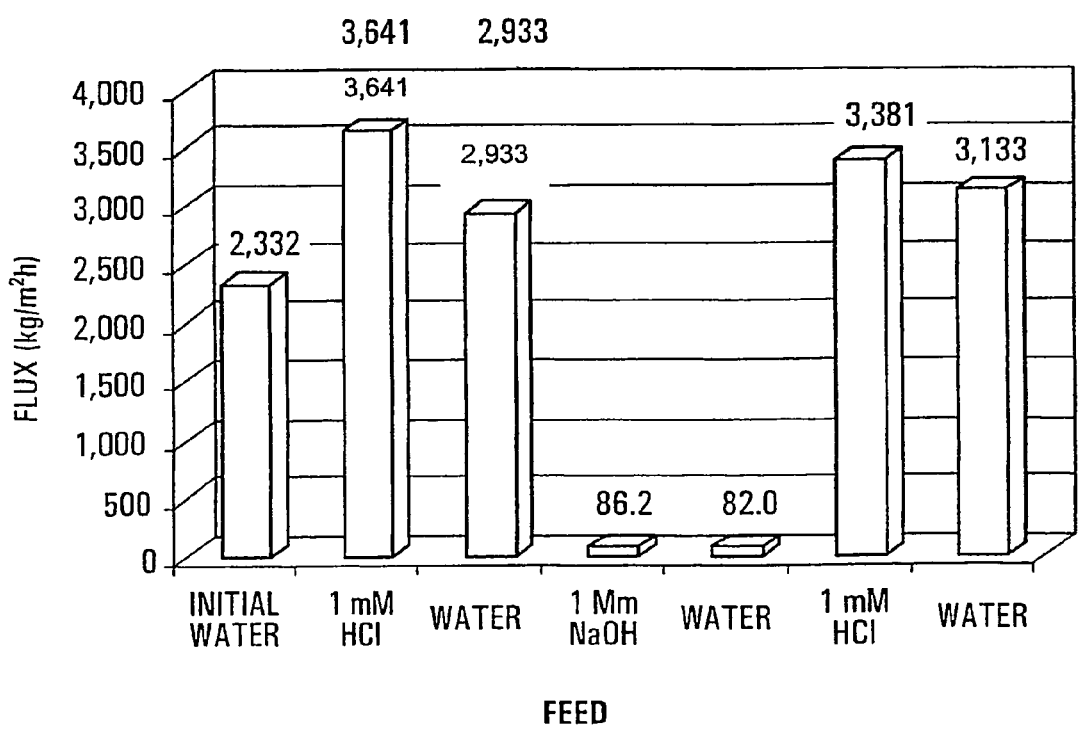
FIG. 18 graphically displays the effect of ionic interactions on the flux through a composite material at a pressure of 100 kPa.

This example illustrates the responsiveness of the responsive composite materials according to Example 30 to ionic interactions. For this purpose, the composite materials were tested with solutions of different pH and/or salt concentrations by measuring the flux at 100 kPa. A typical change in flux taking place with the change of pH from about 3 (1 mM HCl) to about 12 (1 mM NaOH), obtained with membrane AM675 is shown in FIG. 18. It can be seen from the Figure that the flux measured with 1 mM HCl is nearly 100 times larger than the flux measured with 1 mM NaOH. The reason for this behavior of the membranes lies in changes in the degree of ionization of the acid component of the macroporous gel. At high pH (1 mM NaOH) the carboxyl groups of the acid component become ionized and the electrostatic repulsive force causes the polymer chains to uncoil and stretch until balanced by counteracting forces of the polymer network elasticity and confinement imposed by the support member of the membrane. The swelling polymer chains reduce the pore volume and the pore radius in the gel. At low pH (1 mM HCl) the carboxyl groups are converted into neutral carboxylic acid groups, the electrostatic forces disappear, and the gel shrinks (collapses) enlarging the pores in the gel. The presence of the support member prevents the gel from collapsing as a whole, i.e., from the process that would occur in the unsupported bulk gel, and closing the pores. Thus, the presence of the support reverses the direction in which hydraulic properties of the gel change. When pure water flux is measured, the values obtained depend on the distance from equilibrium ionization at the water pH (~5.5). The initial water flux can be assumed to be measured at equilibrium. Immediately after the acid or base, the gel is far from equilibrium with water and the pure water flux reflects this state by being close to the flux in the ionized form (after NaOH) or neutral form (after HCl).

The ratio of the flux measured with 1 mM HCl to that measured with 1 mM NaOH has been taken as a measure of membrane response (MR). The results obtained with membranes described in Example 30-37 are shown in Table 11.

TABLE 11

Results for Examples 30-37

| | \multicolumn{8}{c|}{Membrane ID} |
|---|---|---|---|---|---|---|---|---|
| | AM675 | AM678 | AM680 | AM681 | AM682 | AM684 | AM683 | AM694 |
| Total Monomer Conc. Wt-% | 19.9 | 13.3 | 12.8 | 12.6 | 23.8 | 31.0 | 38.8 | 24.0 |
| Degree of Crosslinking Mol-% | 5.0 | 5.0 | 5.2 | 10.8 | 10.9 | 10.8 | 10.8 | 10.2 |
| Membrane Response (MR) | 89.6 | 372.2 | 352.0 | 29.4 | 10.3 | 5.6 | 4.8 | 19.5 |

The results in Table 11 show that the response of the composite membranes of this invention to ionic interaction can also be controlled by the total concentration of monomer mixture and the degree of crosslinking. As the monomer concentration increases, the membrane sensitivity to the environmental changes decreases. Similar effect is found when the degree of crosslinking is increased.

Example 39

This example illustrates the ability of membranes based on responsive composite materials of this invention to fractionate proteins. The separation of therapeutic proteins Human Serum Albumin (HSA) and Human Immunoglobulin G (HIgG) was chosen as a case study. Human plasma is the starting material for the production of a number of therapeutic proteins, which are referred to as plasma proteins. The most abundant amongst these are HSA and HIgG, both of which are manufactured in bulk quantities. These proteins are generally fractionated by precipitation based processes which give high product throughput but poor resolution in terms of separation. Membrane based processes such as ultrafiltrations have the potential for giving both high throughput and high resolution.

Two composite membranes of this invention containing responsive macroporous gel, duplicates of membrane AM695 (see Tables 10 and 11), were tested for their suitability in separation of these plasma proteins. In the experiments discussed here, the change in membrane pore size with change in salt concentration was utilized to effect protein-protein separation in the manner desirable, i.e. sequential release from the membrane module. Other environmental conditions such as pH could well be used to achieve a similar objective.

Figure 19A:
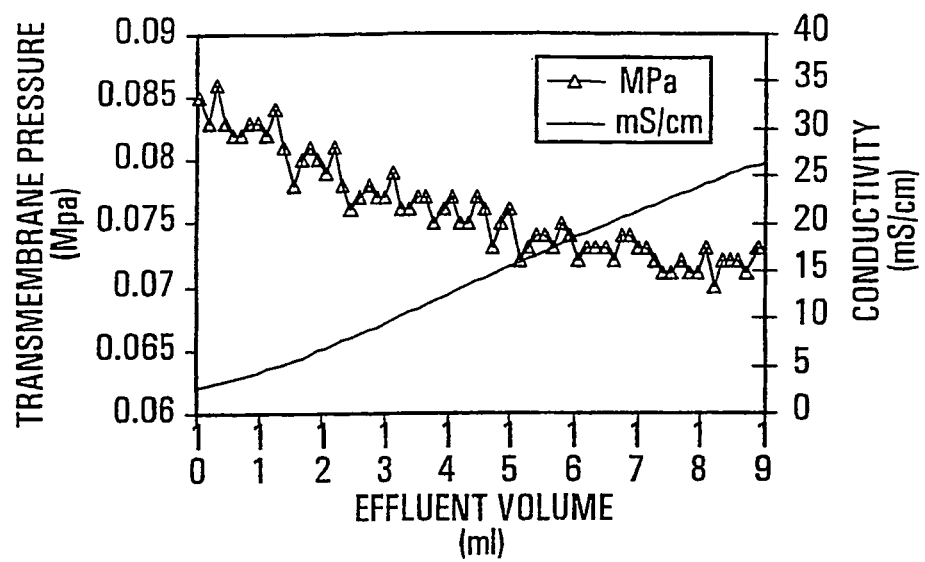
FIG. 19 graphically displays changes in trans-membrane pressure and permeate conductivity as a function of salt concentration in the permeate (A and B) and the changes of trans-membrane pressure as a function of permeate conductivity (salt concentration) (C).
Figure 19B:
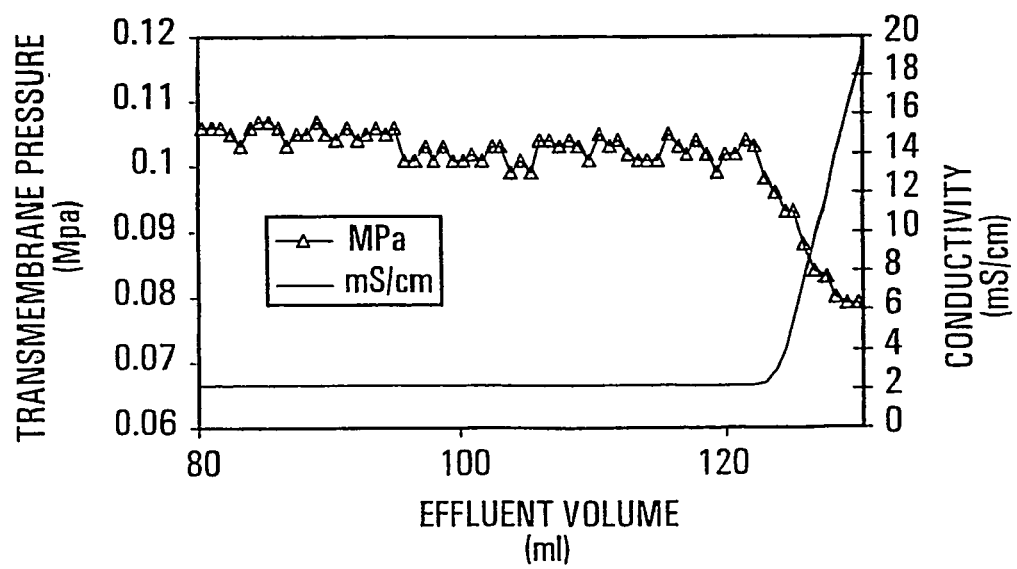
Figure 19C:
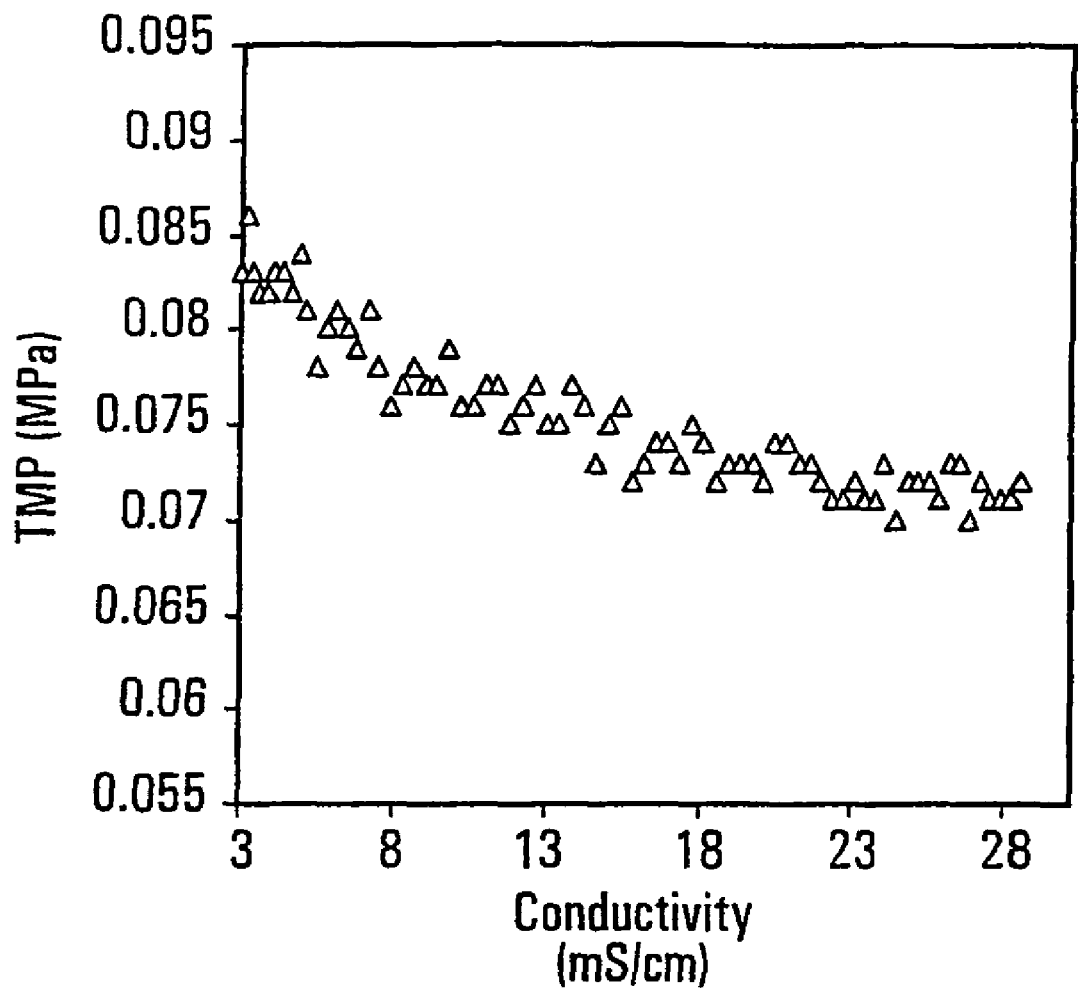

A binary carrier phase system was used in the ultrafiltration experiments. The starting carrier phase in all the experiments was one with a low salt concentration (typically 5-10 mM NaCl). In all the experiments the carried phase was switched to one with a high salt concentration (typically 1 M NaCl). The change in salt concentration within the membrane module could be tracked by observing the conductivity of the permeate stream. The change in transmembrane pressure gave an idea about the change in membrane hydraulic permeability with change in salt concentration. FIG. 19 shows the changes of transmembrane pressure and conductivity as a function of the permeate salt concentration (FIGS. 19A and B) and the changes of transmembrane pressure as a function of permeate conductivity (FIG. 19C). In this experiment the salt concentration was being increased continuously in a linear fashion. The transmembrane pressure observed is related to the permeate salt concentration and reflects changes in pore-diameter.

Experiments were carried out using human serum albumin and human immunoglobulin mixtures. The ultrafiltration was started at a low salt concentration (i.e. 10 mM). At this condition, human serum albumin was transmitted while human immunoglobulin G was almost totally retained. The salt concentration was then increased and this increased the pore diameter (as evident from drop in pressure in constant permeate flux ultrafiltration). This in turn led to the transmission of human immunoglobulin G through the membrane. Hence by altering the environmental condition it was possible to sequentially transmit proteins having different sizes through the same membrane. If the initial mixture had also contained a protein significantly larger than human immunoglobulin, it would have been possible to fractionate the three proteins (i.e. human serum albumin, human immunoglobulin and the significantly bigger protein) by appropriately controlling the change in salt concentration. Two of the three fractions obtained here would be in the permeate while the third fraction would be in the retentate.

Figure 20:
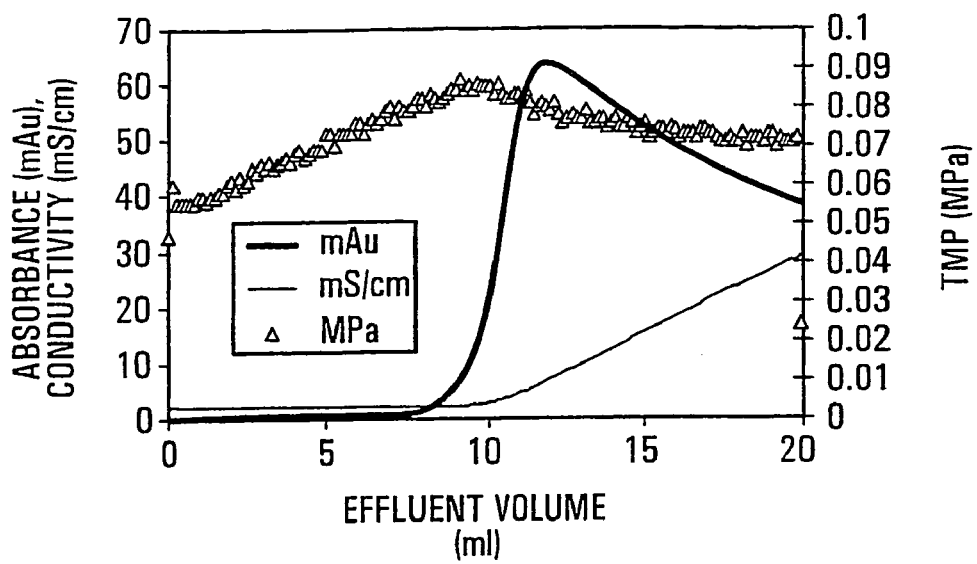
FIG. 20 shows the relationship between trans-membrane pressure, conductivity and absorbance for the HIgG ultrafiltration carried out in Example 39.
Figure 21:
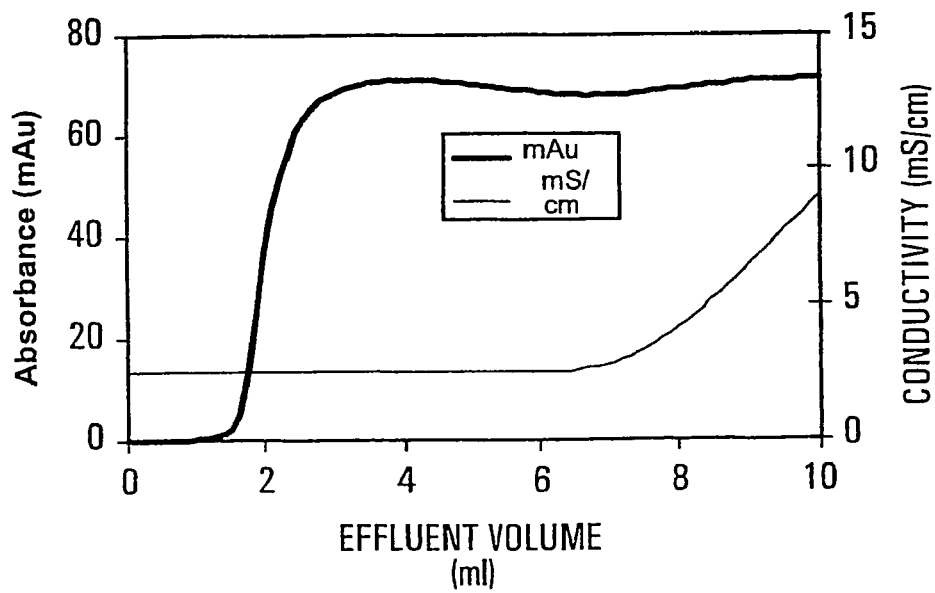
FIG. 21 shows the relationship between conductivity and absorbance for the HSA ultrafiltration carried out in Example 39.
Figure 22:
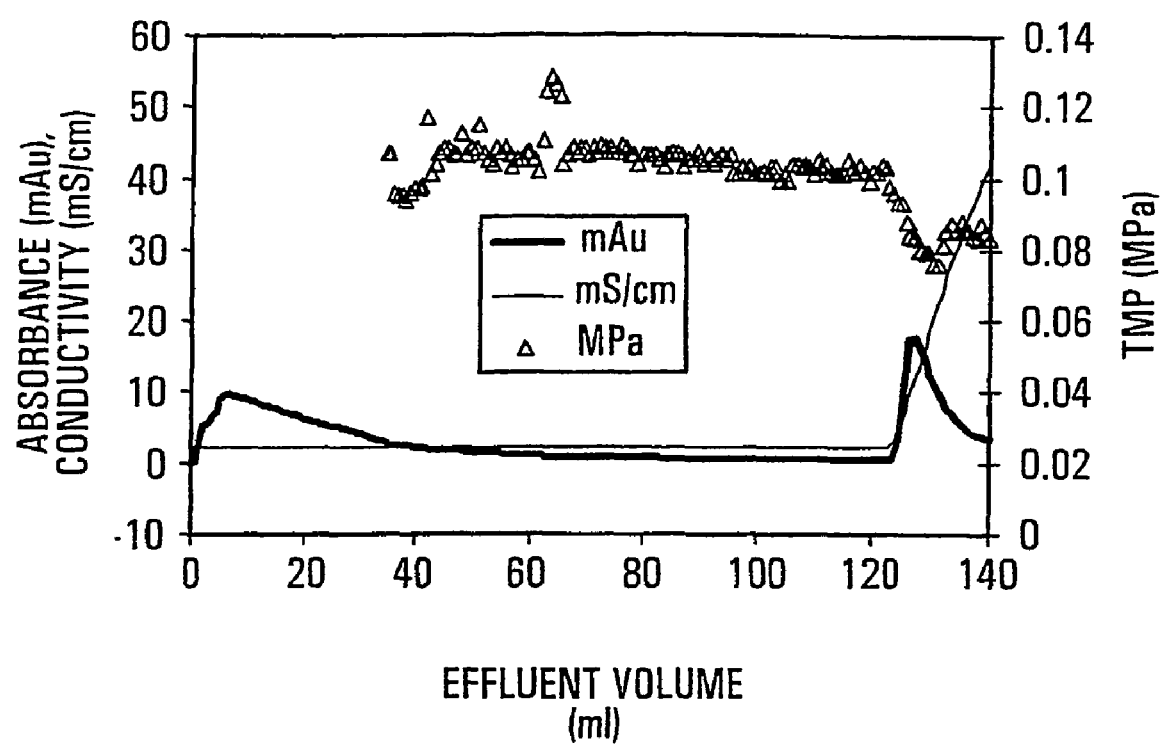
FIG. 22 shows the relationship between trans-membrane pressure, conductivity and absorbance for the HSA/HIgG ultrafiltration carried out in Example 39.

The results obtained with duplicates of membrane AM694 are shown in FIGS. 20, 21, and 22. FIG. 20 shows the results obtained with HIgG ultrafiltration. As evident from the figure, very little, if any HIgG was transmitted at the low salt concentration. However, when the salt concentration was increased, the HIgG was released from the membrane module. The drop in TMP with increase in salt concentration was due to the increase in pore diameter.

The results presented in FIG. 21 were obtained with HSA ultrafiltration. As evident from the figure HSA was freely transmitted through the membrane even at low salt concentration. When the salt concentration was increased, the transmission of HSA was found to increase a bit.

FIG. 22 shows the results obtained with HSA/HIgG ultrafiltration. At low salt concentration, HSA alone was transmitted. Ultrafiltration was continued until HSA was nearly completely removed from the membrane module. The HIgG was then released by increasing the salt concentration.

Example 40

This example illustrates a method for making a positively charged composite material of the invention having a high protein binding capacity.

A 15 wt-% solution was prepared by dissolving (3-acrylamidopropyl)-trimethylammonium chloride (APTAC), N-(hydroxymethyl)acrylamide and N,N'-methylenebisacrylamide as crosslinker in a molar ratio of 1:0.32:0.1, respectively, in a solvent mixture containing 10 wt-% water, 60 wt-% di(propylene glycol)methyl ether and 30 wt-% dimethylformamide (DMF). The photo-initiator Irgacure® 2959 was added in the amount of 1% with respect to the mass of the monomers.

A sample of the fibrous non-woven polypropylene substrate TR2611A was placed on a polyethylene sheet and filled with the monomer solution. The substrate was subsequently covered with another polyethylene sheet and the resulting sandwich was run between two rubber rollers to press the monomer solution into the pores and to remove any excess solution. The substrate was irradiated for 5 minutes at 350 nm. The composite material was then removed from between the polyethylene sheets, washed with water and TRIS-buffer solution and stored in water for 24 hrs.

Several samples were prepared according to the above process, and the samples were then dried and weighed. The average mass gain of the composite material was 55.7% of the original weight of the starting support member.

The protein (BSA) adsorption characteristic of a multi-membrane stack of the above composite material was examined using the general procedure for a mono-layer of the composite material, as described earlier. The membrane stack tested contained 4 membrane layers, giving a total thickness 1.05 mm. The protein solution used was a 25 mM TRIS buffer solution with a protein concentration of 0.4 g/L, and the flow rate of the protein solution was 5.0 ml/min at 150 kPa. The breakthrough capacity for BSA was 281 mg/ml. In a subsequent desorption step, approximately 85% of the BSA was recovered.

Example 41

This examples illustrates the properties of a typical composite material containing macroporous poly(2-hydroxyethylemethacrylate) gel crosslinked with TRIM and containing an EVAL stabilising polymer caged by the HEMA-TRIM network.

The support member used was a poly(propylene) non-woven fabric (TR2611A) and a monomer solution containing 10.0 wt-% of HEMA, 10.1 wt-% of TRIM, 2.8 wt-% of EVAL in a solvent mixture containing 60 wt-% of 2-propanol and 40 wt-% of water. A photoinitiator was added to the solution in an amount equal to 1 wt-% of monomers. The solution was applied to the support member according to the general procedure described above. The irradiation was carried out for 30 min. The resulting composite material was thoroughly washed with several fresh portions of deionized water and the sample was tested for water permeability. A duplicate sample was dried at 70-80° C., weighed, and its mass and dimensions were taken. The sample was subsequently rewetted for 15 min. After that time the sample mass and dimensions were measured and the composite material was tested for water permeability. The mass gain due to gel incorporation was found to be 163±6 wt-%. The properties of the composite material prior and after drying are shown in Table 12.

TABLE 12

Effect of Stabilising Polymer

| Parameter | Value before Drying (Initial) | Value after Drying and Rewetting |
|---|---|---|
| Disk Diameter (mm) | 78 ± 1 | 78 ± 1 |
| Disk Thickness (μm) | 333 ± 6 | 335 ± 4 |

TABLE 12-continued

Effect of Stabilising Polymer

| Parameter | Value before Drying (Initial) | Value after Drying and Rewetting |
|---|---|---|
| Hydrodynamic Permeability ($m^2$) | $2.46 \times 10^{-14}$ | $2.47 \times 10^{-14}$ |
| Hydrodynamic Pore Radius (nm) | 409 ± 2 | 407 ± 6 |

The data presented in the above table indicates that both the dimensions and the hydrodynamic permeability remained the same before and after drying, within the experimental error.

Figure 23A:
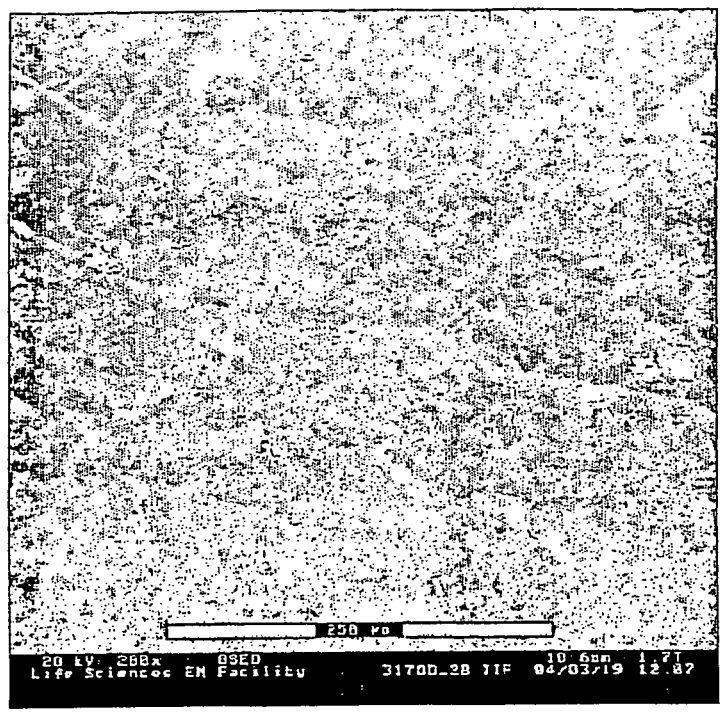
FIGS. 23A and 23B show microscope images of a 2-hydroxyethylmethacrylate (HEMA)-based stable composite material prepared in accordance with Example 41.
Figure 23B:
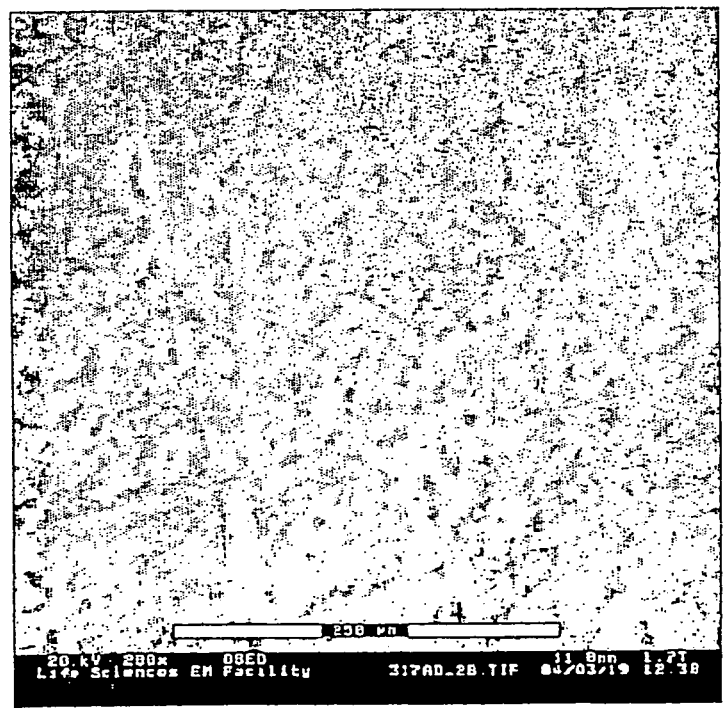

Microscopic pictures of a composite material prepared according to this example, prior to and after drying, are shown in FIGS. 23A and 23B. The micrographs of FIGS. 23A and B show no difference in the general appearance of the HEMA-TRIM composite material surface.

Example 42

This example shows that stable composite materials with different pore radii can be made with the same gel chemistry.

A monomer solution containing 5.0 wt-% of HEMA, 5.0 wt-% of TRIM, and 3.1 wt-% of EVAL in a solvent mixture containing 60 wt-% of 2-propanol and 40 wt-% of water was prepared, and a photoinitiator was added to the solution in an amount equal to 1 wt-% of monomers. The solution was applied to a porous support member and irradiated for 30 min at a wavelength of 350 nm. The resulting composite material was thoroughly washed with deionized water, its dimensions were measured, and the composite material was subsequently tested for hydrodynamic permeability. After drying at 70-80° C. for 1 hour, the composite material was weighed and its dimensions were measured. The rewetted composite material was tested for hydrodynamic permeability. The results are presented in Table 13.

TABLE 13

Effect of Stabilising Polymer

| Parameter | Initial Value | Post-Drying Value |
|---|---|---|
| Hydrodynamic Permeability ($m^2$) | $5.39 \times 10^{-14}$ | $5.39 \times 10^{-14}$ |
| Disk Diameter (mm) | 80 ± 1 | 79 ± 1 |
| Sample Thickness (μm) | 370 ± 28 | 364 ± 42 |
| Hydrodynamic Pore Radius (nm) | 566 ± 5 | 565 ± 12 |

The data shows that by reducing the monomer concentration a composite material with a larger pore radius could be made. The pore radius increased from 409 nm in the composite material of Example 41 to 566 nm in a composite material of this example. The composite material dimensions and performance remain stable within the measurement error.

Example 43

This example illustrates that different gel chemistries can be used to produce stable composite materials.

Two monomer solutions, one containing 9.9 wt-% of NVP, 10.2 wt-% of TRIM, and 2.1 wt-% of EVAL and another containing 10.0 wt-% of acrylic acid, 10.0 wt-% of TRIM, and 2.2 wt-% of EVAL in 2-propanol/water (3/2 by wt-%)

were prepared. The photoinitiator was added to the solutions in an amount equal to 1 wt-% of monomers. The solutions were applied to a TR2611A porous support member. The samples were irradiated for 30 min at a 350 nm wavelength. The resulting composite materials were thoroughly washed with deionized water, their dimensions were measured, and the composite materials were subsequently tested for hydrodynamic permeability. After drying at 70-80° C. for 1 hour, the composite materials were weighed and their dimensions were measured. Rewetted composite materials were tested for hydrodynamic permeability. The results are presented in Table 14.

TABLE 14

Comparison of Different Macroporous Gels Comprising Similar Stabilising polymers

| Parameter | NVP Gel | | AA Gel | |
|---|---|---|---|---|
| | Initial Value | Post-Drying Value | Initial Value | Post-Drying Value |
| Hydrodynamic Permeability ($m^2$) | $4.92 \times 10^{-15}$ | $5.11 \times 10^{-15}$ | $5.78 \times 10^{-15}$ | $5.51 \times 10^{-15}$ |
| Disk Diameter (mm) | 78 ± 1 | 78 ± 1 | 78 ± 1 | 77 ± 1 |
| Sample Thickness (µm) | 377 ± 2 | 374 ± 4 | 369 ± 8 | 354 ± 12 |
| Hydrodynamic Pore Radius (nm) | 187 ± 2 | 192 ± 4 | 196 ± 6 | 191 ± 10 |

The data shows that the composite materials containing poly(N-vinylpyrrolidone) and poly(acrylic acid) gels with entrapped EVAL as a stabilising polymer are stable when dried and rewetted. The changes in composite material dimensions and performance are within experimental errors.

Figure 24A:
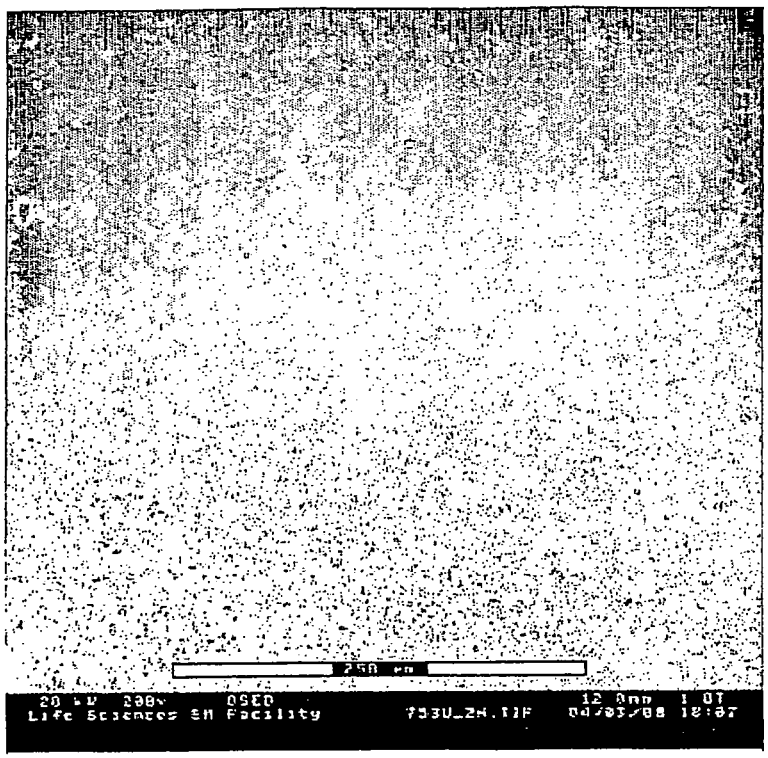
FIGS. 24A and 24B show microscope images of a dried N-vinylpyrrolidone (NVP)-based composite material prepared in accordance with Example 43.
Figure 24B:
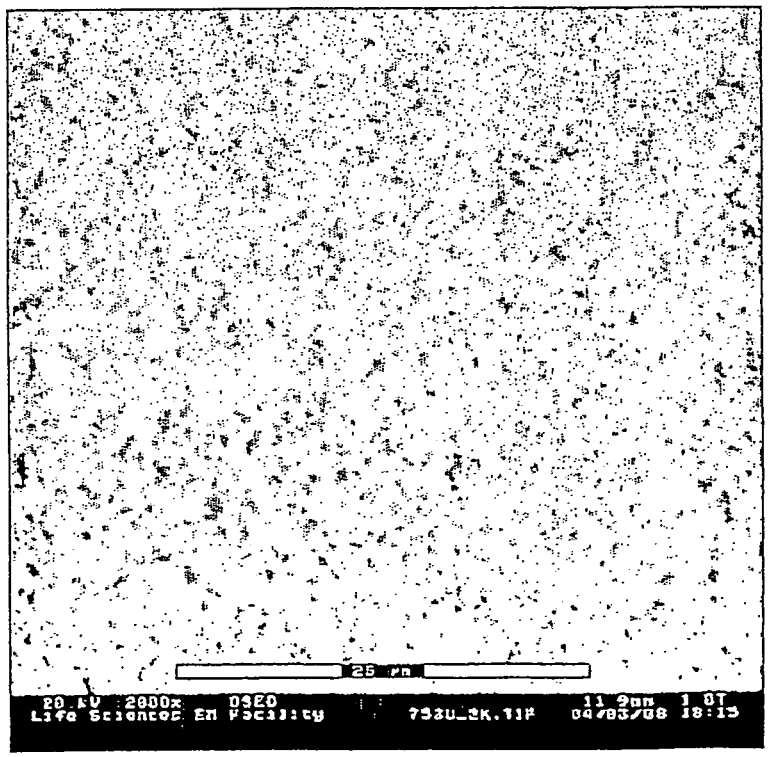

In FIGS. 24A and B, a surface of the dry NVP-TRIM composite material is shown at two magnifications. The Figures show a very uniform porous gel with pores visually smaller than that shown in FIG. 23. This observation is in a good agreement with the measurements of hydrodynamic permeability and hydrodynamic radius for each of these composite materials.

Example 44

This example shows that different stabilising polymers can be used to provide stable composite materials.

A solution containing 10.0 wt-% of HEMA, 9.9 wt-% of TRIM, 2.8 wt-% of cellulose acetate (having a degree of acetylation of 39.7 wt-% and a molecular weight of 50000 Da), and a photoinitiator (1 wt-% of HEMA and TRIM monomers) in acetone was applied to a TR2611A support member. The support member was then irradiated for 30 minutes, followed by a thorough wash with water. The dimension and permeability of the initial and the dried composite material are presented in Table 15.

TABLE 15

Results with Cellulose Acetate as the Stabilising Polymer

| Parameter | Initial Value | Post-Drying Value |
|---|---|---|
| Hydrodynamic Permeability ($m^2$) | $8.29 \times 10^{-14}$ | $8.13 \times 10^{-14}$ |
| Disk Diameter (mm) | 78 ± 1 | 77 ± 1 |
| Sample Thickness (µm) | 325 ± 26 | 321 ± 15 |
| Hydrodynamic Pore Radius (nm) | 824 ± 52 | 816 ± 52 |

As with other composite materials presented above, the changes in dimensions and performance introduced by drying are within an experimental error range.

Example 45

This example illustrates that the absence of a stabilising polymer in the macroporous gel can lead to the formation of a homogeneous or micro heterogeneous gel in the pores of the support member that undergoes a dramatic change of permeability upon drying.

A solution containing 10.0 wt-% of HEMA, 10.0 wt-% of TRIM, and a photoinitiator (1 wt-% of HEMA and TRIM monomers) in a 2-propanol/water (3/2 ratio by weight) mixture was applied to a TR2611A support member. The sample was irradiated at a 350 nm wavelength for 30 min followed by a thorough wash with water. The dimensions and permeability of the initial and the oven-dried composite material are presented in Table 16.

TABLE 16

Drying Effect on a Composite Material not Comprising a Stabilising Polymer

| Parameter | Initial Value | Post-Drying Value |
|---|---|---|
| Hydrodynamic Permeability ($m^2$) | $2.88 \times 10^{-17}$ | $9.64 \times 10^{-15}$ |
| Disk Diameter (mm) | 78 ± 1 | 73 ± 1 |
| Sample Thickness (µm) | 301 ± 4 | 298 ± 15 |
| Hydrodynamic Pore Radius (nm) | 13 ± 1 | 238 ± 9 |

As the permeability data indicates, the gel formed in the absence of the stabilising polymer is homogeneous or micro heterogeneous due to the high degree of crosslinking. The permeability is two to three orders of magnitude lower than that of the composite materials presented in the previous examples. Drying of the macroporous gel causes large shrinkage of the sample and over two orders of magnitude increase in permeability.

Figure 25A:
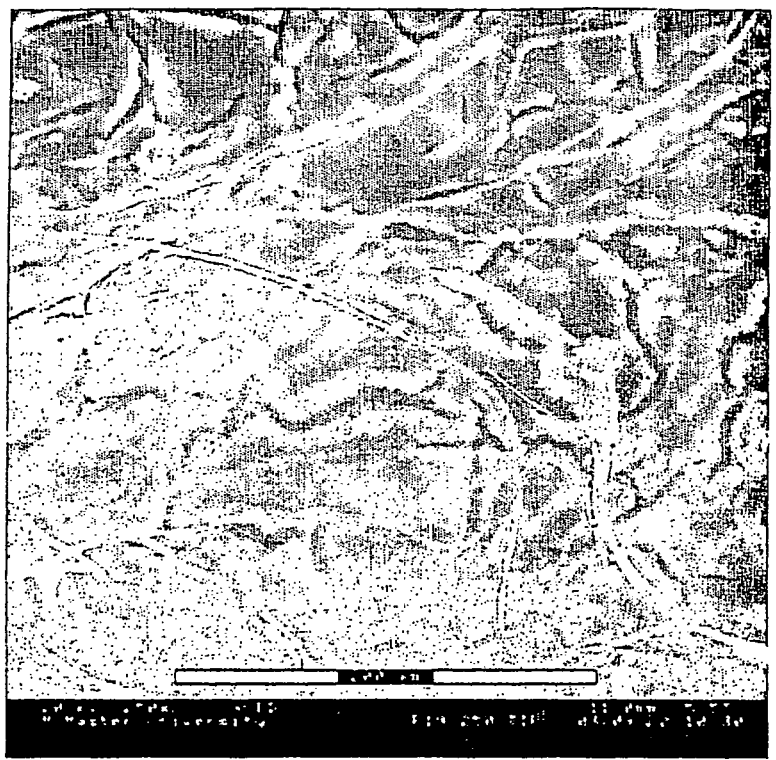
FIGS. 25A and 25B show microscope images of a HEMA-based composite material prepared in accordance with Example 45, which HEMA-based composite material does not contains a stabilising polymer.
Figure 25B:
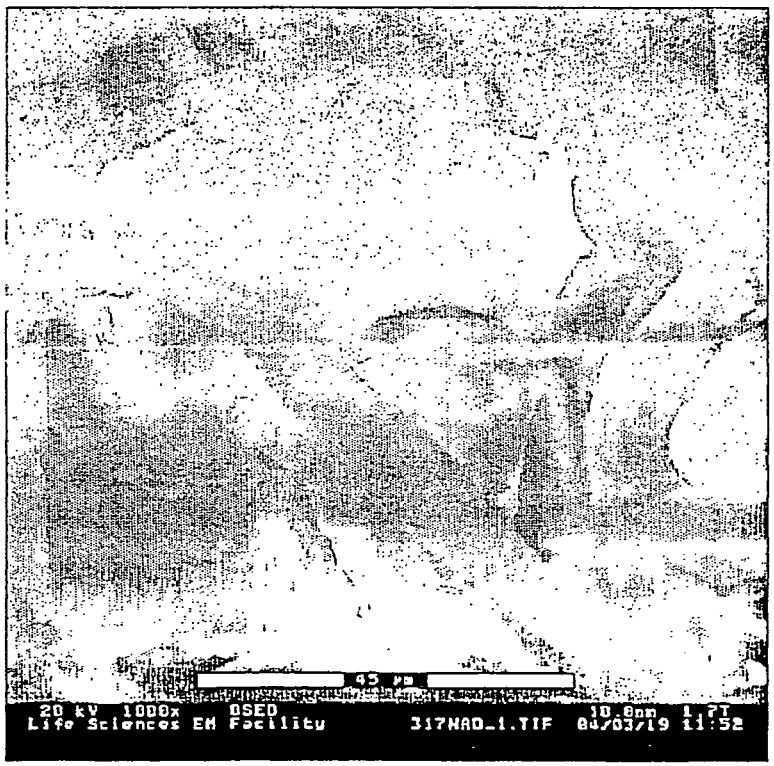

As shown in FIGS. 25A and B, HEMA composite materials prepared without a stabilising polymer and subsequently dried differ from those composite materials of Example 41. Large cracks in the macroporous gel are visible in FIG. 25A, and the higher magnification (FIG. 25B) shows that there doesn't appear to be any pores in the gel.

Example 46

This example shows that using water-soluble polymers instead of non-soluble stabilising polymers leads to porous but unstable composite materials.

A solution containing 4.2 wt-% of HEMA, 4.2 wt-% of TRIM, 11.1 wt-% of PEG MW=8,000, and a photoinitiator (1 wt-% of HEMA and TRIM monomers) in a solvent mixture containing 65 wt-% of dipropylene glycol monomethyl ether (DPM) and 35 wt-% of water was used to prepare a composite material comprising a macroporous HEMA gel. The solution was applied to a TR2611A support member and irradiated at a 350 nm wavelength for 30 min. The resulting support member was thoroughly washed with water and tested for permeability before and after drying in an oven at 70-80° C. for 1 hour. The composite material dimensions and performance are presented in Table 17.

TABLE 17

Effect of the Presence of a Water-Soluble Polymer
Instead of a Water-Insoluble Stabilising Polymer

| Parameter | Initial Value | Post-Drying Value |
|---|---|---|
| Hydrodynamic Permeability ($m^2$) | $4.79 \times 10^{-15}$ | $6.72 \times 10^{-14}$ |
| Disk Diameter (mm) | 78 ± 1 | 76 ± 1 |
| Sample Thickness (μm) | 318 ± 20 | 312 ± 14 |
| Hydrodynamic Pore Radius (nm) | 154 ± 15 | 649 ± 14 |

As shown by the initial value of the hydrodynamic pore radius, PEG functioned as a porogen, giving a composite material with a pore radius one order of magnitude higher than a similar composite material produced without PEG (Example 45). However, the PEG polymer is very soluble in water and it was washed out from the composite material during the washing step. The loss of PEG was confirmed by the mass gain calculation, which gave a value that was close to the theoretical value calculated based only on the monomer concentration of the solution. Drying induced a change of over one order of magnitude in permeability and the ensuing change in hydrodynamic pore radius.

Figure 26:
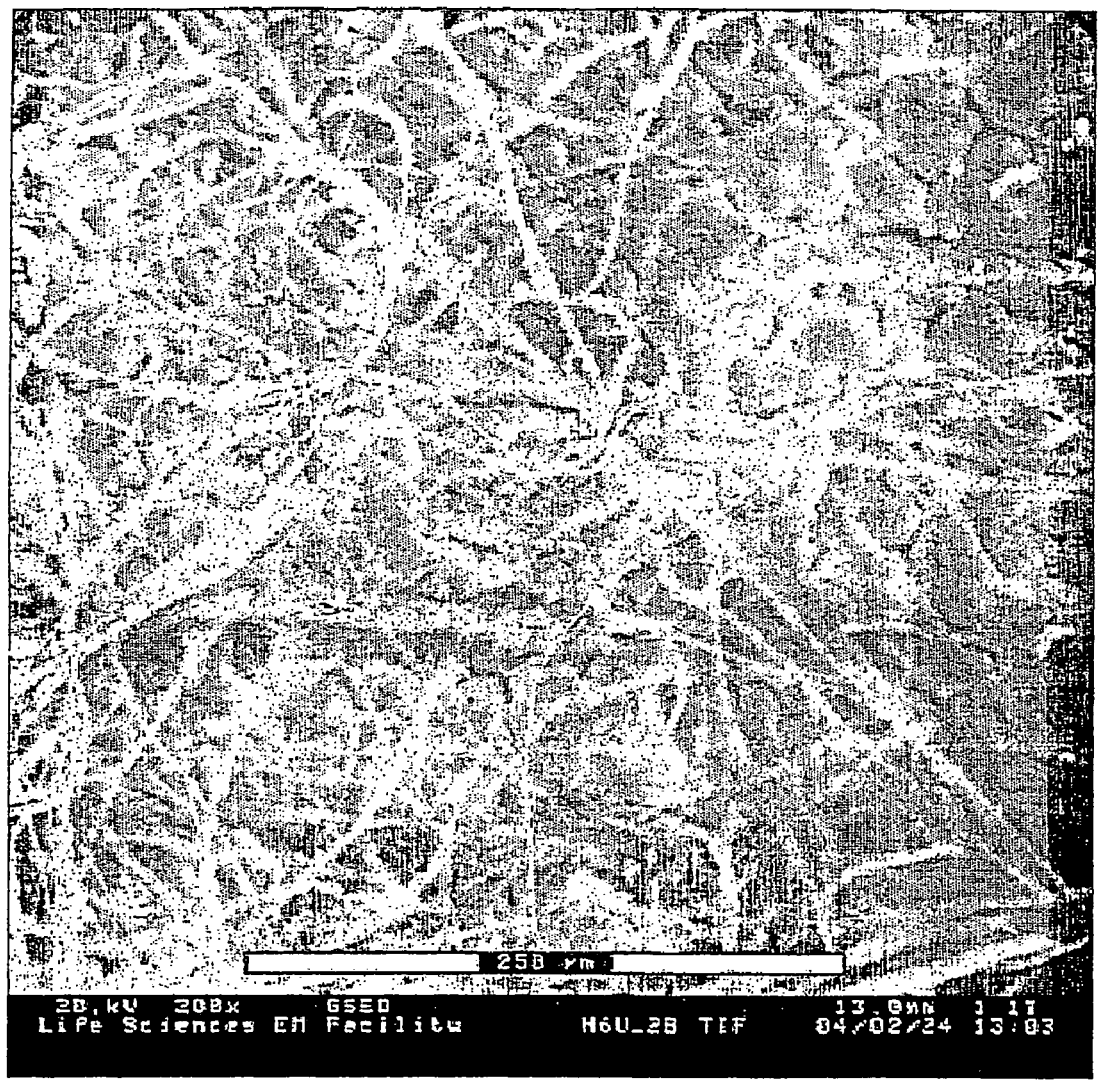
FIG. 26 shows microscope images of a HEMA-based composite material prepared in accordance with Example 46, wherein poly(ethylene glycol)(PEG) is used as a porogen.

FIG. 26 shows the surface of a dry HEMA-TRIM composite material as prepared above, with PEG as a porogen. Cracks in the gel are visible, and provide a reason for the increase in the observed gel hydrodynamic permeability values.

Example 47

This example illustrates the stability of composite materials after standing in water for an extended period.

Samples prepared according to Example 41 and Example 44 were dried and subsequently placed in deionized water for 7 days. After this time, the dimensions of the composite materials were measured and their permeability tested. The composite materials were subsequently dried in oven and weighed. The results are presented in Table 18.

TABLE 18

Stability of Composite Materials After Extended Contact with Water

| Parameter | Composite Material of Example 41 | | Composite Material of Example 44 | |
|---|---|---|---|---|
| | Dried Sample | After 7 Days in Water | Dried Sample | After 7 Days in Water |
| Hydrodynamic Permeability ($m^2$) | $2.43 \times 10^{-14}$ | $2.32 \times 10^{-14}$ | $8.13 \times 10^{-14}$ | $7.87 \times 10^{-14}$ |
| Disk Diameter (mm) | 78 ± 1 | 78 ± 1 | 77 ± 1 | 77 ± 1 |
| Sample Thickness (μm) | 362 ± 12 | 363 ± 16 | 321 ± 15 | 320 ± 15 |
| Mass of Dry Disk (g) | 0.5470 | 0.5472 | 0.4924 | 0.4907 |

The data in Table 18 shows that there is no loss of mass, and no washing-out of the stabilising polymer following the drying and subsequent rewetting of the composite materials. The mass gain of the composite materials was found to be slightly larger than predicted from the support pore volume, the monomer solution concentration and the stabilising polymer. The higher than predicted mass gain was likely a result of the presence of small amounts gel layers left on the support surfaces during manual application of the monomer solution. The small drop in permeability (~5%) observed on prolonged soaking reflects the constrained swelling of the macroporous gel.

Example 48

This example illustrates that stabilising polymers can be used to prepare stable composite materials that are responsive to environmental changes.

The flux at 100 kPa of the composite material prepared in Example 43 (containing acrylic acid) was measured using solutions of different pH. The solutions used had a pH of about 3 (1 mM HCl) and a pH of about 12 (1 mM HaOH), respectively. The ratio of the flux measured with 1 mM HCl to the one measured with 1 mM NaOH has been taken as a measure of membrane response (MR). A membrane response MR=264 was measured for this composite material.

Example 49

This example illustrates the calculation results used to estimate the polymer-solvent affinity measured by the distance $d_o$.

TABLE 19

Polymer-Solvent Affinities

| | Solvent | Polymer | | |
|---|---|---|---|---|
| Cohesion Parameter | $H_2O^a$ | $EVAL^b$ (32 mol-% ethylene) | $CA^c$ (39.7 wt-% of acetyl content) | Polysulfone $(PS)^d$ |
| Dispersive, $\delta_d$ | 15.6 | 17.9 | 18.6 | 19.0 |
| Dipolar, $\delta_p$ | 16.0 | 21.9 | 12.7 | 0.0 |
| Hydrogen bonding, $\delta_h$ | 42.3 | 32.0 | 11.0 | 7.0 |

TABLE 19-continued

Polymer-Solvent Affinities

| Cohesion Parameter | Solvent $H_2O^a$ | Polymer | | |
|---|---|---|---|---|
| | | $EVAL^b$ (32 mol-% ethylene) | $CA^c$ (39.7 wt-% of acetyl content) | Polysulfone $(PS)^d$ |
| Three-dimensional, $\delta_t$ | 47.8 | 42.7 | 25.1 | 20.3 |
| Distance, $d_o$ | | 13.6 | 32.0 | 39.4 |

[a] data from Grulke, E. A. In *Polymer Handbook*, 4th ed.; Brandrup, J., Immergut E. H., Grulke, E. A., Eds.; Wiley-Interscience: New York, 1999; Chapter VII, p 697.
[b] calculated from group contribution data
[c] data from Barton A. F. M. In *CRC Handbook of Solubility Parameters and Other Cohesion Parameters*, 2nd ed.; CRC Press: Boca Raton, FL, 1991, Chapter 14.
[d] data from Grulke, E. A. In *Polymer Handbook*, 4th ed.; Brandrup, J., Immergut E. H., Grulke, E. A., Eds.; Wiley-Interscience: New York, 1999; Chapter VII, p 711.

According to the data in Table 19, all three polymers are insoluble in water, with EVAL having the highest affinity to water and polysulfone the lowest one.

All references mentioned herein are incorporated herein by reference to the same extent as if each reference were stated to be specifically incorporated herein by reference.

It must be noted that as used in this specification and the appended claims, the singular forms "a", "an", and "the" include plural reference unless the context clearly dictates otherwise. Unless defined otherwise all technical and scientific terms used herein have the same meaning as commonly understood to one of ordinary skill in the art to which this invention belongs.

To those skilled in the art, it is to be understood that many changes, modifications and variations could be made without departing from the spirit and scope of the present invention as claimed hereinafter.

The invention claimed is:

1. A composite material comprising:
   a support member that has a plurality of pores extending therethrough, and
   a non-self supporting macroporous crosslinked gel that is located in, and fills, the pores of the support member, wherein the macroporous crosslinked gel has macropores of average size between about 10 and about 3000 nm;
   wherein, in the macroporous crosslinked gel is entrapped a stabilising polymer selected from the group consisting of a cellulose derivative, a polyester, a polyamide, a polyacrylate, poly(ethylene-co-vinyl alcohol), polyhydroxystyrene (poly (4-vinylphenol), aromatic poly(ether sulfone), a partially charged polymer, and a copolymer of neutral and charged monomers.

2. A composite material according to claim 1, wherein the stabilising polymer has an affinity parameter $d_0(H_2O)$ of from about 12 to about 40.

3. A composite material according to claim 1, wherein the stabilising polymer has an affinity parameter $d_0(H_2O)$ of from about 12 to about 25.

4. A composite material according to claim 1, wherein the stabilising polymer is non-crosslinked.

5. A composite material according to claim 1, wherein the stabilising polymer has a molecular weight of from 5,000 to 500,000.

6. A composite material according to claim 1, wherein the stabilising polymer is present in an amount of from 5% to 50% by weight, based on the combined weight of macroporous gel and stabilising polymer.

7. A composite material according to claim 1, wherein the stabilising polymer is present in an amount of from 10% to 25% by weight, based on the combined weight of macroporous gel and stabilising polymer.

8. A composite material according to claim 1, wherein the stabilising polymer is soluble in a solvent used to prepare the macroporous gel.

9. A composite material according to claim 1, wherein the stabilizing polymer is a cellulose derivative selected from cellulose acetate, cellulose acetate butyrate, cellulose acetate propionate, 2-hydroxyethyl cellulose and ethyl cellulose.

10. A composite material according to claim 1, wherein the stabilizing polymer is a polyester selected from poly(ethylene adipate), polyethylene glycol terephthalate, poly(L-lactide), poly(DL-lactide) and poly(dl-lactide-co-glycolide).

11. A composite material according to claim 1, wherein the stabilizing polymer is a polyamide selected from poly(hexamethyleneadipamide) and poly(hexamethylenesebacamide).

12. A composite material according to claim 1, wherein the stabilizing polymer is a polyacrylate selected from poly(2-hydroxyethyl methacrylate) and poly(2-hydroxypropyl methacrylate).

13. A composite material according to claim 1, wherein the stabilizing polymer is poly(ethylene-co-vinyl alcohol) having an ethylene content of 27, 32, 38, or 44 mol-%.

14. A composite material according to claim 1, wherein the stabilizing polymer is a partially charged polymer selected from sulfonated polyetherether ketone (<86% sulfonation), sulfonated poly(phenylene oxide) (<70% sulfonation), sulfonated polysulfone (<70% sulfonation), aminated polysulfone (<70% amination), aminated poly(phenylene oxide) (<70% amination) and protonated or alkylated poly(4-vinylpyridine) (<30% protonation or alkylation).

15. A composite material according to claim 1, wherein the stabilizing polymer is a copolymer of neutral and charged monomers that is a poly(ethylene-co-acrylic acid) copolymer.

16. A composite material according to claim 15, wherein the poly(ethylene-co-acrylic acid) copolymer comprises 5, 10, 15, or 20 wt-% of acrylic acid.

17. A composite material according to claim 1, wherein the stabilizing polymer is an ethylene-co-vinyl alcohol copolymer or cellulose acetate.

18. A composite material according to claim 17, wherein the cellulose acetate has a degree of acetylation of from 29 to 61%.

* * * * *